United States Patent
Hirose et al.

(10) Patent No.: US 9,062,038 B2
(45) Date of Patent: Jun. 23, 2015

(54) HETEROARYLS AND USES THEREOF

(75) Inventors: Masaaki Hirose, Kanagawa (JP);
Yongbo Hu, Winchester, MA (US);
Zhigen Hu, Newton Center, MA (US);
Hong Myung Lee, Cambridge, MA (US); Zhan Shi, Concord, MA (US);
Stepan Vyskocil, Arlington, MA (US);
Tianlin Xu, Shrewsbury, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 13/814,812

(22) PCT Filed: Aug. 10, 2011

(86) PCT No.: PCT/US2011/047241
§ 371 (c)(1),
(2), (4) Date: Jun. 20, 2013

(87) PCT Pub. No.: WO2012/021611
PCT Pub. Date: Feb. 16, 2012

(65) Prior Publication Data
US 2013/0267563 A1    Oct. 10, 2013

Related U.S. Application Data

(60) Provisional application No. 61/372,579, filed on Aug. 11, 2010.

(51) Int. Cl.
| C07D 413/04 | (2006.01) |
|---|---|
| C07D 413/14 | (2006.01) |
| C07D 471/04 | (2006.01) |
| C07D 487/04 | (2006.01) |
| C07D 495/04 | (2006.01) |
| C07D 498/04 | (2006.01) |

(52) U.S. Cl.
CPC .......... *C07D 413/04* (2013.01); *C07D 413/14* (2013.01); *C07D 471/04* (2013.01); *C07D 487/04* (2013.01); *C07D 495/04* (2013.01); *C07D 498/04* (2013.01)

(58) Field of Classification Search
CPC ........................... C07D 413/04; C07D 413/14
USPC ........................................ 514/340; 546/271.4
See application file for complete search history.

(56) References Cited

U.S. PATENT DOCUMENTS

| 3,257,203 A | 6/1966 | Sus et al. |
|---|---|---|
| 3,821,384 A | 6/1974 | Ariyan et al. |
| 3,852,293 A | 12/1974 | Ariyan et al. |
| 4,371,607 A | 2/1983 | Donges |
| 4,506,368 A * | 3/1985 | Lee ................ 372/53 |
| 5,134,142 A | 7/1992 | Matsuo et al. |
| 6,015,826 A | 1/2000 | Pechacek et al. |
| 6,555,501 B1 | 4/2003 | Bastiaans et al. |
| 6,608,087 B1 | 8/2003 | Charifson et al. |
| 6,984,652 B2 | 1/2006 | Yager et al. |
| 7,074,801 B1 | 7/2006 | Yoshida et al. |
| 7,405,235 B2 | 7/2008 | Levy et al. |
| 7,504,513 B2 | 3/2009 | Boylan et al. |
| 7,511,041 B2 | 3/2009 | Shimada et al. |
| 7,560,568 B2 | 7/2009 | Emmitte |
| 7,741,348 B2 | 6/2010 | Nan et al. |
| 8,183,240 B2 | 5/2012 | Cardin et al. |

(Continued)

FOREIGN PATENT DOCUMENTS

| CN | 1816549 A | 8/2006 |
|---|---|---|
| DE | 275870 A1 | 2/1990 |

(Continued)

OTHER PUBLICATIONS

Fu et al., Journal of Organic Chemistry (2008), 73(19), 7625-7630.*
U.S. Appl. No. 14/318,223, filed Jun. 27, 2014, Freeze et al.
U.S. Appl. No. 14/445,373, filed Jul. 29, 2014, Hilrose et al.
U.S. Appl. No. 14/445,376, filed Jul. 29, 2014, Freeze et al.
1,2,4-Oxadiazole, 5-[5-(1H-imidazol-2-y1)-2-thienyl]-3-(methoxymethyl)-(CA Index Name), CAS Registry No. 1069660-66-7, entered Nov. 2, 2008.
1,2,4-Oxadiazole-3-ethanamine, 5-[5-(1H-imidazol-2-y1)-2-thienyl]-N,N-dimethyl-(CA Index Name), CAS Registry No. 1066888-52-5, entered Oct. 27, 2008.

(Continued)

*Primary Examiner* — Niloofar Rahmani
(74) *Attorney, Agent, or Firm* — Choate, Hall & Stewart LLP; Andrea L. C. Reid

(57) ABSTRACT

This invention provides compounds of formula IA or IB: wherein HY, $R^1$, $R^2$, $G_1$, W, n, and A are as described in the specification. The compounds are inhibitors of PI3K and/or mTor and are thus useful for treating proliferative, inflammatory, or cardiovascular disorders.

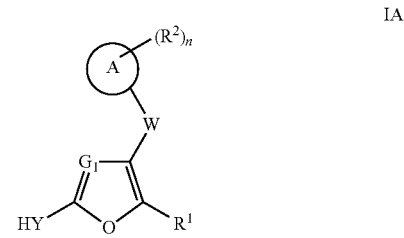

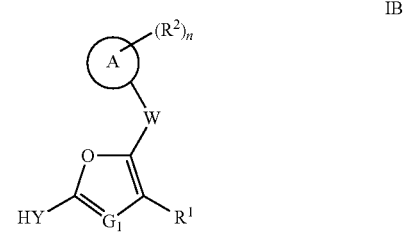

13 Claims, No Drawings

(56) References Cited

U.S. PATENT DOCUMENTS

| | | |
|---|---|---|
| 8,440,664 B2 | 5/2013 | Cardin et al. |
| 8,586,582 B2 | 11/2013 | Liang et al. |
| 8,765,746 B2 | 7/2014 | Freeze et al. |
| 8,796,268 B2 | 8/2014 | Freeze et al. |
| 8,796,271 B2 | 8/2014 | Hirose et al. |
| 2002/0022729 A1 | 2/2002 | Kawai et al. |
| 2003/0096816 A1 | 5/2003 | Cao et al. |
| 2004/0116425 A1 | 6/2004 | Li et al. |
| 2004/0198773 A1 | 10/2004 | Hart et al. |
| 2004/0248896 A1 | 12/2004 | Dean et al. |
| 2004/0266751 A1 | 12/2004 | King |
| 2005/0004122 A1 | 1/2005 | Brown et al. |
| 2005/0054697 A1 | 3/2005 | Yager et al. |
| 2005/0124678 A1 | 6/2005 | Levy et al. |
| 2006/0041006 A1 | 2/2006 | Ibrahim et al. |
| 2006/0074119 A1 | 4/2006 | Andrews et al. |
| 2006/0128732 A1 | 6/2006 | Shimada et al. |
| 2006/0199804 A1 | 9/2006 | Hummersone et al. |
| 2007/0066666 A1 | 3/2007 | Emmitte |
| 2007/0142415 A1 | 6/2007 | Vanotti et al. |
| 2007/0203210 A1 | 8/2007 | Boylan et al. |
| 2008/0021217 A1 | 1/2008 | Borchardt et al. |
| 2008/0045570 A1 | 2/2008 | Brenchley et al. |
| 2008/0132546 A1 | 6/2008 | Basarab et al. |
| 2008/0255120 A1 | 10/2008 | Lin et al. |
| 2008/0293716 A1 | 11/2008 | Drewry et al. |
| 2008/0306060 A1 | 12/2008 | Alexander et al. |
| 2008/0306121 A1 | 12/2008 | Nan et al. |
| 2009/0012031 A1 | 1/2009 | Chinnaiyan et al. |
| 2009/0030016 A1 | 1/2009 | Gandhi et al. |
| 2009/0036435 A1 | 2/2009 | Curry et al. |
| 2009/0247567 A1 | 10/2009 | Do et al. |
| 2009/0325925 A1 | 12/2009 | Renou et al. |
| 2010/0075951 A1 | 3/2010 | Cardin et al. |
| 2010/0130473 A1 | 5/2010 | Hummersone et al. |
| 2010/0256172 A1 | 10/2010 | Shi et al. |
| 2010/0267759 A1 | 10/2010 | Seefeld et al. |
| 2011/0003806 A1 | 1/2011 | Hirose et al. |
| 2011/0003807 A1 | 1/2011 | Banno et al. |
| 2011/0021531 A1 | 1/2011 | Chobanian et al. |
| 2012/0142732 A1 | 6/2012 | Cullis et al. |
| 2012/0172345 A1 | 7/2012 | Freeze et al. |
| 2012/0178723 A1 | 7/2012 | Hirose et al. |
| 2012/0214794 A1 | 8/2012 | Freeze et al. |
| 2013/0165464 A1 | 6/2013 | Chau et al. |
| 2013/0165472 A1 | 6/2013 | Chau et al. |
| 2013/0165483 A1 | 6/2013 | Chau et al. |
| 2013/0217689 A1 | 8/2013 | Cardin et al. |
| 2013/0267563 A1 | 10/2013 | Hirose et al. |

FOREIGN PATENT DOCUMENTS

| | | |
|---|---|---|
| EP | 0853083 A1 | 7/1998 |
| EP | 2313399 B1 | 5/2014 |
| GB | 874634 A | 8/1961 |
| JP | 10087490 A | 4/1998 |
| JP | 2006-508063 A | 3/2006 |
| JP | 2006-525266 A | 11/2006 |
| JP | 2007-519720 A | 7/2007 |
| JP | 2007-197324 A | 8/2007 |
| JP | 2008-531537 A | 8/2008 |
| WO | WO-97/12615 A1 | 4/1997 |
| WO | WO-98/08845 A1 | 3/1998 |
| WO | WO-98/47894 A1 | 10/1998 |
| WO | WO-00/02871 A1 | 1/2000 |
| WO | WO-00/35912 A1 | 6/2000 |
| WO | WO-00/63204 A2 | 10/2000 |
| WO | WO-02/088107 A1 | 11/2002 |
| WO | WO-03/015776 A1 | 2/2003 |
| WO | WO-03/027085 A2 | 4/2003 |
| WO | WO-03/027107 A1 | 4/2003 |
| WO | WO-03/040096 A2 | 5/2003 |
| WO | WO-2004/016592 A1 | 2/2004 |
| WO | WO-2004/016741 A2 | 2/2004 |
| WO | WO-2004/096797 A1 | 11/2004 |
| WO | WO-2006/046031 A1 | 5/2006 |
| WO | WO-2006/068933 A2 | 6/2006 |
| WO | WO-2006/069063 A1 | 6/2006 |
| WO | WO-2006/078287 A2 | 7/2006 |
| WO | WO-2006/097030 A1 | 9/2006 |
| WO | WO-2006/102194 A1 | 9/2006 |
| WO | WO-2006/114313 A1 | 11/2006 |
| WO | WO-2007/002559 A1 | 1/2007 |
| WO | WO-2007/043400 A1 | 4/2007 |
| WO | WO-2007/087488 A2 | 8/2007 |
| WO | WO-2007/096315 A1 | 8/2007 |
| WO | WO-2007/110344 A1 | 10/2007 |
| WO | WO-2007/129044 A1 | 11/2007 |
| WO | WO-2007/129161 A2 | 11/2007 |
| WO | WO-2007/138110 A2 | 12/2007 |
| WO | WO-2008/014238 A2 | 1/2008 |
| WO | WO-2008/021235 A2 | 2/2008 |
| WO | WO-2008/023159 A1 | 2/2008 |
| WO | WO-2008/024980 A2 | 2/2008 |
| WO | WO-2008/036541 A1 | 3/2008 |
| WO | WO-2008/047109 A1 | 4/2008 |
| WO | WO-2008/083070 A1 | 7/2008 |
| WO | WO-2008/090382 A1 | 7/2008 |
| WO | WO-2008/097835 A2 | 8/2008 |
| WO | WO-2008/098105 A1 | 8/2008 |
| WO | WO-2008/134679 A1 | 11/2008 |
| WO | WO-2008/139161 A1 | 11/2008 |
| WO | WO-2008/157273 A1 | 12/2008 |
| WO | WO-2009/040730 A2 | 4/2009 |
| WO | WO-2009/042607 A1 | 4/2009 |
| WO | WO-2009/049028 A1 | 4/2009 |
| WO | WO-2009/094224 A1 | 7/2009 |
| WO | WO-2009/106885 A1 | 9/2009 |
| WO | WO-2009/122148 A1 | 10/2009 |
| WO | WO-2009/154741 A1 | 12/2009 |
| WO | WO-2009/158374 A2 | 12/2009 |
| WO | WO-2010/001126 A1 | 1/2010 |
| WO | WO-2010/005841 A1 | 1/2010 |
| WO | WO-2010/017079 A1 | 2/2010 |
| WO | WO-2010/055304 A2 | 5/2010 |
| WO | WO-2010/071741 A1 | 6/2010 |
| WO | WO-2010/080873 A1 | 7/2010 |
| WO | WO-2010/090716 A1 | 8/2010 |
| WO | WO-2010/121675 A2 | 10/2010 |
| WO | WO-2010/132598 A1 | 11/2010 |
| WO | WO-2011/043371 A1 | 4/2011 |

OTHER PUBLICATIONS

1H-Pyrazole-1-carboxylic acid, 5-[2,2'-bithiophen]-5-yl-, ethyl ester (CA Index Name), CAS Registry No. 957595-63-0, entered Dec. 12, 2007.
2,7-Naphthyridine, 1,2,3,4-tetrahydro-5-[5-[5-(1H-imidazol-2-yl)-2-thienyl]-1,2,4-oxadiazol-3-yl]-6-methyl-(CA Index Name), CAS Registry No. 1069717-72-1, entered Nov. 2, 2008.
2-Thiazolamine, 4-[5-(2H-tetrazol-5-yl)-2-thienyl]-(CA Index Name), CAS Registry No. 937625-84-8, entered Jun. 17, 2007.
2-Thiophenecarboxylic acid, 3-(4-chlorophenyl)-4-cyano-5-(4-morpholinyl)-(CA Index Name), CAS Registry No. 883097-33-4, entered May 5, 2006.
2-Thiophenecarboxylic acid, 3-(4-chlorophenyl)-4-cyano-5-(4-morpholinyl)-, methyl ester (CA Index Name), CAS Registry No. 882283-38-7, entered Apr. 30, 2006.
3H-1,2,4-Triazole-3-thione, 2,4-dihydro-4-methyl-5-[4-methyl-2-(5-methyl-3-isoxazolyl)-5-thiazolyl]-(CA Index Name), CAS Registry No. 264616-86-6, entered May 12, 2000.
4-Oxazolecarboxylic acid, 5-[(ethoxymethylene)amino]-2-(4-pyridinyl)-, ethyl ester-(CA Index Name), CAS Registry No. 885901-22-4, entered May 29, 2006.
4-Thiazolecarboxamide, 2-(4-acetyl-5-methyl-1H-1,2,3-triazol-1-yl)-N,N-diethyl-5-phenyl-(CA Index Name), CAS Registry No. 709639-21-4, entered Jul. 14, 2004.
Abdelrazek et al., Heterocyclic Synthesis with Nitriles: Synthesis of Some Novel Thiophene and Thieno[2,3-d]Pyrimidine Derivatives, Phosphorus, Sulfur, and Silicons, 71:93-97 (1992).
Acetamide, N-(3,5-dichlorophenyl)-2-[[4-methyl-5[-methyl-2-(5-methyl-3-isoxazolyl)-5-thiazolyl]-4H-1,2,4-triazol-3-yl]thio]- (CA

(56) References Cited

OTHER PUBLICATIONS

Index Name), CAS Registry No. 264626-19-9, entered May 12, 2000.
Acetamide, N-(4-chlorophenyl)-2[[4-methyl-5[4-methyl-2-(5-methyl-3-isoxazolyl)-5-thiazolyl]-4H-1,2,4-triazol-3-yl]thio]-(CA Index Name), CAS Registry No. 264626-21-3, entered May 12, 2000.
Adib, M. et al., Facile One-Pot Three-Component Synthesis of Functionalized Pyridylfuran-2-amines, Helvetica Chimica Acta, 89(2):299-303 (2006).
Al-Azawe et al., Synthesis of 2,5-Disubstituted Thiazoles and Their Reactions with Grignard Reagents, Journal of the Iraqi Chemical Society, 13(1): 1-13 (1988).
Amer, A. et al., Ring Closure Reactions involving 1-Hydrazinophthalazine [1]. Reactions with 1,2,4-Tricarbonyl and 1,3-Dicarbonyl Compounds, Journal of Heterocyclic Chemistry, 20: 1231-1238 (1983).
Amer, A., et al., Factors Influencing the Pathway of Reactions of 1-Hydra-Zinophthalazine With Di-and Tricarbonyl Compounds, Heterocycles, 26(7): 1853-1862 (1987).
Annis, D. A., et al., Inhibitors of the Lipid Phosphatase SHIP2 Discovered by High Throughput Affinity Selection-Mass Spectrometry Screening of Combinatorial Libraries, Combinatorial Chemistry & High Throughput Screening, 12:760-771 (2009).
Batista et al., Synthesis and characterization of new thienylpyrrolyl-benzothiazoles as efficient and thermally stable nonlinear optical chromophores, Tetrahedron, 63(20):4258-4265 (2007).
Batista et al., Synthesis and Second-Order Nonlinear Optical Properties of New Chromophores Containing Benzimidazole, Thiophene, and Pyrrole Heterocycles, Tetrahedron,.
Benzamide, N,N'-(4,4'-di-2-thienyl[2,2'-bithiazole]-5,5'-diyl)bis-(CA Index Name) CAS Registry No. 691381-57-4, entered Jun. 10, 2004.
Benzamide, N,N'[4,4'-bis (4-fluorophenyl)[2,2'-bithiazole]-5,5'-diyl]bis[4-methyl- (CA Index Name) CAS Registry No. 691381-60-9, entered Jun. 10, 2004.
Benzamide, N-(4'-amino-Z,3'-dihydro-3',4-diphenyl-2'-thioxo[2,5'-bithiazol]-5-yl)-(CA Index Name)CAS Registry No. 879910-33-5, entered Apr. 10, 2006.
Benzamide, N[2-(5-amino-1-phenyl-1H-pyrazol-4-yl)-4-phenyl-5-thiazolyl]-4-methyl-(CA Index Name), CAS Registry No. 1017527-68-2, entered Apr. 27, 2008.
Berndt, A. et al., The p100δcrystal structure uncovers mechanisms for selectivity and potency of novel PI3K inhibitors, Nature Chemical Biology, 6(2):117-124 (2010).
Boppana, K. et al., Knowledge based identification of MAO-B selective inhibitors using pharmacophore and structure based virtual screening models, European Journal of Medicinal Chemistry, 44:3584-3590 (2009).
Caballero, J., et al., Investigation of the Differences in Activity between Hydroxycycloalkyl N1 Substituted Pyrazole Derivatives As Inhibitors of B-Raf Kinase by Using Docking, Molecular Dynamics, QM/MM, and Fragment-Based De Novo Design: Study of Binding Mode of Diastereomer Compounds, Journal of Chemical Information and Modeling, 51: 2920-2931 (2011).
Carbamic acid, N,N'-(4,4'-di-2-thienyl[2,2'-bithiazole]-5,5'-diyl)bis-,C,C'-dimethyl ester (CA Index Name) CAS Registry No. 691381-58-5, entered Jun. 10, 2004.
Carbamic acid,4,4'-diphenyl[2,2'-bithiazole]-5,5'-diyl)bis-, dimethyl ester (9Cl)(CA Index Name), CAS Registry No. 505060-78-6, entered Apr. 25, 2003.
Cecchi, L. et al., Synthesis and Biological Activity of Some 3-(Pyrazol-1'-yl)Indazole Derivatives, II Farmaco, 39: 945-952 (1984).
Chahma, M. et al., Delocalized Nitrogen Carbanions in $S_{RN}1$ Reactions, Journal of Organic Chemistry, 60: 8015-8022 (1995).
Chattopadhyay, S. K. et al., Efficient Construction of the Carbon Skeleton of the Novel Polyoxazole-Based Cyclopeptide Ib-01211 via a Biomimetic Macrocyclisation, SYNLETT, 4:555-558 (2010).

Choi, W. et al., Synthesis and Antiproliferative Activities of 1-Substituted-3-(3-chloro-5-methoxyphenyl)-4-pyridinylpyrazole Derivatives Against Melanoma Cell Line, Bulletin of the Korean Chemical Society, 30(9):2027-2031 (2009).
Cudworth et al., Structure-Activity Relationship Development of Dihaloaryl Triazole Compounds as Insecticides and Acaricides. 1. Phenyl Thiophen-2-yl Triazoles, Journal of Agricultural and Food Chemistry, 55(18): 7517-7526 (2007).
Database CAS Registry (Columbus, Ohio), RN 893689-50-4 (Entered Jul. 17, 2006).
Database CAS Registry (Columbus, Ohio), RN 893692-42-7 (Entered Jul. 17, 2006).
Database CAS Registry (Columbus, Ohio), RN 893704-20-6 (Entered Jul. 17, 2006).
Database CAS Registry (Columbus, Ohio), RN 893705-40-3 (Entered Jul. 17, 2006).
Database CAS Registry (Columbus, Ohio), RN 898517-78-7 (Entered Aug. 3, 2006).
Database CHEMCATS, Chemical Abstracts Service, Columbus, Ohio, US, XP002545555, order No. T5337328.
Datta, A. et al., A Novel Route to Methyl 3-3(3,4-Disubstituted 5-alkylthio/amino-2-thienyl) propenoates, Synthesis, 7:556-567 (1988).
Di Fabio, R. et al., Dihydropyrrole[2,3-D]pyridine Derivatives As Novel Corticotropin-Releasing Factor-1 Antagonists: Mapping of the Receptor Binding Pocket by in Silico Docking Studies, Journal of Medicinal Chemistry, 51(22): 7273-7286 (2008).
Dzvinchuk, I.B. et al., Selective Recyclization of 2-Aroylmethyl-1H-Benzimidazole Hydrazones by Condensation with Dimethylformamide, Chemistry of Heterocyclic Compounds, 37(9): 1096-1101 (2001).
Dzvinchuk, I.B. et al., Synthesis and Tautomerism of 2-[3(5)-Aryl(methyl)pyrazol-4-yl]-1-benzimidazoles, Chemistry of Heterocyclic Compounds, 42(9): 1190-1196 (2006).
Emmitte et al., Discovery of Thiophene Inhibitors of Polo-like Kinase, Bioorganic & Medicinal Chemistry Letters, 19(3): 1018-1021 (2009).
Fletcher, A. N. et al., Laser Dye Stability, Part 12. The Pyridinium Salts, Applied Physics, B43:155-160 (1987).
Fridman et al., Spectroscopy, Photophysical and Photochemical Properties of Bisimidazole, Derivatives, Journal of Photochemistry and Photobiology, A: Chemistry, 188(1): 25-33 (2007).
Ge, M. et al., A General Method for the Preparation of 3-Acyl-4-cyano-5-amino-pyrazoles, Tetrahedron Letters, 47: 5797-5799 (2006).
Golub, T.R. et al., Molecular classification of cancer: class discovery and class prediction by gene expression monitoring, Science, 286(5439):531-7 (1999).
Green et al., Parallel Synthesis of 2-aryl-4-aminobenzimidazoles and their Evaluation as Gonadotropin Releasing Hormone Antagonists, Journal of Combinatorial Chemistry, 11(1): 117-125 (2009).
Hernandez, D. et al., Synthesis and Antitumor Activity of Mechercharmycin A Analogues, Journal of Medicinal Chemistry, 51: 5722-5730 (2008).
Hernandez, D. et al., Synthesis of Natural Product Derivatives Containing 2,4-Concatenated Oxazoles, European Journal of Organic Chemistry, (19): 3389-3396 (2008).
Heyde, C. et al., A Simple Route to N,N-dialkyl Derivatives of 2-Amino-5-thiophenecarboxylates, Eur. J. Org. Chem.: 3273-3278 (2000).
Hirai, K. et al., Heterocyclic Cation Systems. 14. Synthesis of Thieno[3,2-e][1,4]diazepine, Thiazolo[4,5-e][1,4]diazepine, and s-Triazolo[3,4-c]thiazolo[4,5-e][1,4]diazepine Derivatives, Journal of Organic Chemistry, 45:253-260 (1980).
Hirai, K. et al., Novel Synthesis of Thiophene Derivatives from 1,3-Oxathiol-2-ylideneimmonium Salt, Chemical & Pharmaceutical Bulletin, 19(10): 2194-2197 (1971).
Imidazo[1,2-a]pyridine, 6-[3-[5-(2H-tetrazol-5-yl)-2-thienyl]-1H-pyrazol-4-yl]-3-(2-thiazolyl)-(CA Index Name) CAS Registry No. 732241-18-8, entered Aug. 25, 2004.
International Search Report for PCT/US09/00513, 3 pages (Jun. 10, 2009).

(56) References Cited

OTHER PUBLICATIONS

International Search Report for PCT/US09/03607, 4 pages (Sep. 23, 2009).
International Search Report for PCT/US10/00234, 3 pages (Jun. 1, 2010).
International Search Report for PCT/US11/47245, 2 pages (Dec. 22, 2011).
International Search Report for PCT/US11/47407, 2 pages (Dec. 22, 2011).
International Search Report for PCT/US11/56135, 4 pages (May 31, 2012).
International Search Report for PCT/US2011/047241, 3 pages (Jan. 6, 2012).
Laszlo et al., Pyrroles and Other Heterocycles as Inhibitors of P38 Kinase, Bioorganic and Medical Chemistry Letters, 8: 2689-2694 (1998).
Lethu et al., Discovery of a New Class of Protein Farnesyltransferase Inhibitors in the Arylthiophene Series, J. Med. Chem., 52: 6205-6208 (2009).
Liang, J. et al., Crystal Structure of PI3K [sic] SH3 Domain at 2.0 A Resolution, Journal of Molecular Biology, 257:632-643 (1996).
Lima, L. et al., Bioisosterism: A Useful Strategy for Molecular Modification and Drug Design, Current Medicinal Chemistry, 12: 23-49 (2005).
Liu et al., Highly Selective and Potent Thiophenes as PI3K Inhibitors with Oral Antitumor Activity, Med. Chem. Lett., 2:809-813 (2011).
Lucchesini, A Simple Way to Sequentially Connected Polycycles Containing Terminal Pyrrole Rings: Synthesis of Possible Precursors of Materials for Nonlinear Optics, Tetrahedron, 48(45): 9951-9966 (1992).
Mamedov et al., Synthesis and Some Properties of the Methyl Ester and N,N-diethylamide of 2-Azido-5-Phyenyl-4-Thiazolecarboxylic Acid, Chemistry of Heterocyclic Compounds, 29(5): 607-611 (1993).
Matschke et al., Quinomethides Versus Unsymmetric Hybrids: Two Variations of NonRadicaloid SEM-States in Four-Electron Redox Systems of bis-4H-imidazoles, Structural Chemistry, 19(3):399-405 (2008).
Menear, K. A. et al., Identification and optimisation of novel and selective small molecular weight kinase inhibitors of mTOR, Bioorganic & Medicinal Chemistry Letters, 19:5898-5901 (2009).
Moorthy et al., In Silico-Based Structural Analysis of Arylthiophene Derivatives for Ftase Inhibitory Activity, hERG, and Other Toxic Effects, Journal of Biomolecular Screening, 16(9):1037-1046 (2011).
Morpholine, 4-(5-(4,5-diphenyl-1H-imidazol-2-yl)-2-thienyl]-, Ryan Scientific Screening Library, Publication date: Jan. 25, 2008, CAS Registry No. 851954-74-0.
Nagasaki et al., Casreact 139:52925 (2003).
Nagasaki et al., Useful Synthesis of Various Thiazole and Polythiazolyl Derivatives from Thiocarboxamide and-Bromacyl Compound, Heterocycles, 60(2): 321-335 (2003).
Pinto, I.L. et al., The Synthesis of 5-Alkoxy and 5-Amino Substituted Thiophenes, Tetrahedron Letters, 41(10): 1597-1600 (2000).
Pyrazolo[1,5-a]pyrimidin-7(4H)-one,3-ethyl-5-[5-(1H-imidazol-2-yl)-2-thienyl]- (CA Index Name), CAS Registry No. 1087437-07-7, entered Dec. 21, 2008.
Raap, R. Some Syntheses with Dimethyl Monothionemalonate, Canadian Journal of Chemistry, 46:13, 2255-2261 (1968).
Rehwald, M. et al., New Synthesis of 2,4-Diaminothiophenes—Use of (1,3-oxathiol-2-ylidene)Malononitrile, Heterocycles, 45(3): 493-500 (1997).
Revesz, L. et al., SAR of 2,6-Diamino-3,5-difluoropyridinyl Substituted Heterocycles as Novel p38 MAP Kinase Inhibitors, Bioorganic & Medicinal Chemistry Letters, 12(16):2109-2112 (2002).
Sheridan, The Most Common Chemical Replacements in Drug-Like Compounds, J. Chem. Inf. Comput. Sci., 42:103-108 (2002).
Thompson, M. J. et al., Development of a Diversity-Oriented Approach to Oxazole-5-amide Libraries, Journal of Organic Chemistry, 74(10):3856-3865 (2009).
Tsuge, O., and Torii, A., Compounds Related to Acridine. VIII.[1]) Reaction of 9-Vinylacridine with p-Substituted Nitrosobenzenes, Bulletin of the Chemical Society of Japan, 45: 3187-3191 (1972).
Wang, Q. et al., Copper-Mediated Amidation of Heterocyclic and Aromatic C—H Bonds, Organic Letters, 11( 22): 5178-5180 (2009).
Welker et al., Recent Syntheses of PI3K-Akt-mTOR signaling pathway inhibitors, Bioorganic & Medicinal Chemistry, 21(14): 4063-4091 (2013).
Written Opinion for PCT/US09/00513, 5 pages (Jun. 10, 2009).
Written Opinion for PCT/US09/03607, 5 pages (Sep. 23, 2009).
Written Opinion for PCT/US10/00234, 6 pages (Jun. 1, 2010).
Written Opinion for PCT/US11/47245, 5 pages (Dec. 22, 2011).
Written Opinion for PCT/US11/47407, 7 pages (Jun. 10, 2009).
Written Opinion for PCT/US11/56135, 13 pages (May 31, 2012).
Written Opinion for PCT/US2011/047241, 9 pages (Jan. 6, 2012).
Ye, L., et al., Pyrazolylthiazole as ΔF508-Cystic Fibrosis Transmembrane Conductance Regulator Correctors with Improved Hydrophilicity Compared to Bithiazoles, Journal of Medicinal Chemistry, 53:3772-3781 (2010).
Zhang, F. et al., Decarboxylative C—H Cross-Coupling of Azoles, Angew. Chem. Int. Ed., 49(15): 2768-2771 (2010).
Zhou et al., Selenium-Containing Heterocycles from Isoselenocyanates: Synthesis of 1,3-Selenazoles from N-Phenylimidoyl Isoselenocyanates, Helvetica Chimica Acta, 83: 1576-1598 (2000).

* cited by examiner

HETEROARYLS AND USES THEREOF

BACKGROUND OF THE INVENTION

Phosphatidylinositol 3-kinase (PI3K) is a family of lipid kinases that phosphorylate phosphatidylinositol at the 3' position of the inositol ring. PI3K is comprised of several classes of genes, including Class IA, IB, II and III and some of these classes contain several isoforms (reviewed in Engelman et al., Nature Review Genetics 7:606-619 (2006)). Adding to the complexity of this family is the fact that PI3Ks function as heterodimers, comprising a catalytic domain and a regulatory domain. The PI3K family is structurally related to a larger group of lipid and serine/threonine protein kinases known as the phosphatidylinositol 3-kinase like kinases (PIKKs), which also includes DNA-PK, ATM, ATR, mTOR, TRRAP and SMG1.

PI3K is activated downstream of various mitogenic signals mediated through receptor tyrosine kinases, and subsequently stimulates a variety of biological outcomes; including increased cell survival, cell cycle progression, cell growth, cell metabolism, cell migration and angiogenesis (reviewed in Cantley, Science 296:1655-57 (2002); Hennessy et al., Nature Reviews Drug Discovery 4:988-1004 (2005); Engelman et al., Nature Review Genetics 7:606-619 (2006)). Thus, PI3K hyper-activation is associated with a number of hyper-proliferative, inflammatory, or cardiovascular disorders; including cancer, inflammation, and cardiovascular disease.

There are a number of genetic aberrations that lead to constitutive PI3K signaling; including activating mutations in PI3K itself (Hennessy et al., Nature Reviews Drug Discovery 4:988-1004 (2005); reviewed in Bader et al., Nature Reviews Cancer 5:921-9 (2005)); RAS (reviewed in Downward Nature Reviews Cancer 3:11-22 (2003)) and upstream receptor tyrosine kinases (reviewed in Zwick et al., Trends in Molecular Medicine 8:17-23 (2002)) as well as inactivating mutations in the tumor suppressor PTEN (reviewed in Cully et al., Nature Reviews Cancer 6:184-92 (2006)). Mutations in each of these gene classes have proven to be oncogenic and are commonly found in a variety of cancers.

The molecules defined within this invention inhibit the activity of PI3K, and therefore may be useful for the treatment of proliferative, inflammatory, or cardiovascular disorders. Cases where PI3K pathway mutations have been linked to proliferative disorders where the molecules defined within this invention may have a therapeutic benefit include benign and malignant tumors and cancers from diverse lineage, including but not limited to those derived from colon (Samuels et al., Science 304:554 (2004); reviewed in Karakas et al., British Journal of Cancer 94: 455-59 (2006)), liver (reviewed in Karakas et al., British Journal of Cancer 94: 455-59 (2006)), intestine (reviewed in Hennessy et al., Nature Reviews Drug Discovery 4:988-1004 (2005)), stomach (Samuels et al., Science 304:554 (2004); reviewed in Karakas et al., British Journal of Cancer 94: 455-59 (2006)), esophagus (Phillips et al., International Journal of Cancer 118:2644-6 (2006)); pancreas (reviewed in Downward Nature Reviews Cancer 3:11-22 (2003)); skin (reviewed in Hennessy et al., Nature Reviews Drug Discovery 4:988-1004 (2005)), prostate (reviewed in Hennessy et al., Nature Reviews Drug Discovery 4:988-1004 (2005)), lung (Samuels et al., Science 304:554 (2004); reviewed in Karakas et al., British Journal of Cancer 94: 455-59 (2006)), breast (Samuels et al., Science 304:554 (2004); Isakoff et al., Can Res 65:10992-1000 (2005); reviewed in Karakas et al., British Journal of Cancer 94: 455-59 (2006)), endometrium (Oda et al., Can Res 65:10669-73 (2005); reviewed in Hennessy et al., Nature Reviews Drug Discovery 4:988-1004 (2005)), cervix (reviewed in Hennessy et al., Nature Reviews Drug Discovery 4:988-1004 (2005)), ovary (Shayesteh et al., Nature Genetics 21:99-102 (1999); reviewed in Karakas et al., British Journal of Cancer 94: 455-59 (2006)), testes (Moul et al., Genes Chromosomes Cancer 5:109-18 (1992); Di Vizio et al., Oncogene 24:1882-94 (2005)), hematological cells (reviewed in Karakas et al., British Journal of Cancer 94: 455-59 (2006); Hennessy et al., Nature Reviews Drug Discovery 4:988-1004 (2005)), pancreas (reviewed in Downward Nature Reviews Cancer 3:11-22 (2003)), thyroid (reviewed in Downward Nature Reviews Cancer 3:11-22 (2003); reviewed in Hennessy et al., Nature Reviews Drug Discovery 4:988-1004 (2005)); brain (Samuels et al., Science 304:554 (2004); reviewed in Karakas et al., British Journal of Cancer 94: 455-59 (2006)), bladder (Lopez-Knowles et al., Cancer Research 66:7401-7404 (2006); Hennessy et al., Nature Reviews Drug Discovery 4:988-1004 (2005)); kidney (reviewed in Downward Nature Reviews Cancer 3:11-22 (2003)) and Head and Neck (reviewed in Engelman et al., Nature Reviews Genetics 7:606-619 (2006)).

Other classes of disorders with aberrant PI3K pathway signaling where the molecules defined within this invention may have a therapeutic benefit include inflammatory and cardiovascular diseases, including but not limited to allergies/anaphylaxis (reviewed in Rommel et al., Nature Reviews Immunology 7:191-201 (2007)), acute and chronic inflammation (reviewed in Ruckle et al., Nature Reviews Drug Discovery 5:903-12 (2006); reviewed in Rommel et al., Nature Reviews Immunology 7:191-201 (2007)), rheumatoid arthritis (reviewed in Rommel et al., Nature Reviews Immunology 7:191-201 (2007)); autoimmunity disorders (reviewed in Ruckle et al., Nature Reviews Drug Discovery 5:903-12 (2006)), thrombosis (Jackson et al., Nature Medicine 11:507-14 (2005); reviewed in Ruckle et al., Nature Reviews Drug Discovery 5:903-12 (2006)), hypertension (reviewed in Ruckle et al., Nature Reviews Drug Discovery 5:903-12 (2006)), cardiac hypertrophy (reviewed in Proud et al., Cardiovascular Research 63:403-13 (2004)), and heart failure (reviewed in Mocanu et al., British Journal of Pharmacology 150:833-8 (2007)).

Vacuolar Protein Sorting 34 (VPS34) is the sole Class III PI3K family member. VPS34 functions in the formation and trafficking of multiple intracellular vesicles, including vacuoles, endosomes, multivessicular bodies, lysosomes and autophagosomes (reviewed in Backer Biochem J 2008; Yan and Backer Biochem J 2007). VPS34 carries out these activities by phosphorylating PtdIns forming PtdIns3P, resulting in the recruitment and localization of a variety of FYVE and PX domain containing effector proteins that facilitate vesicular formation, elongation and movement. At a cellular level, inhibition of VPS34 results in defects in protein sorting and autophagy. Broadly defined, autophagy is a regulated process whereby cells catabolize subcellular components targeted for degradation by enclosing them in double-membrane vesicles which then fuse with lysosomes. Autophagy has been best characterized as occurring during times of nutrient deprivation, but also plays a role in normal cellular and tissue homeostasis and functions, including the development of multiple tissue types, the immune response, clearance of neuronal aggregates and tumor suppression. In addition to functioning in vesicle formation and movement, VPS34 may also participate in several signal transduction pathways (reviewed in Backer Biochem J 2008). Given that VPS34 plays an important role in many critical cellular processes including autophagy, inhibitors of VPS34 may have therapeutic application in a number of diseases, including but not limited to cancer, muscular disorders, neurodegeneration, inflammatory disease, infectious disease and other age related illnesses (reviewed in Shintani and Klionshy Science 2004; Kondo et al Nat Rev Cancer 2005; Delgato et al Immunol Rev 2009).

Clearly, it would be beneficial to provide novel PI3K inhibitors that possess good therapeutic properties, especially for the treatment of proliferative, inflammatory, or cardiovascular disorders.

1. General Description of Compounds of the Invention:

This invention provides compounds that are inhibitors of PI3K, and accordingly are useful for the treatment of proliferative, inflammatory, or cardiovascular disorders. The compounds of this invention are represented by formula IA or IB:

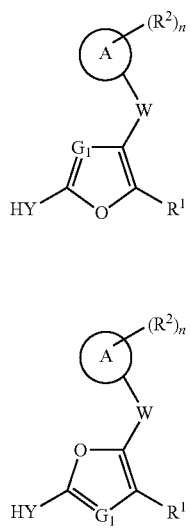

or a pharmaceutically acceptable salt thereof, wherein:
R$^1$ is CY, —C(O)N(R$^3$)$_2$, —C(O)OR$^3$, —C(O)(NH)OH, —C(=NH)NHOH, —C(O)NR$^3$N(R$^3$)$_2$, —C(=N—NH$_2$)NH$_2$, —C(=N)N(R$^3$)$_2$, wherein:
CY is an optionally substituted group selected from:

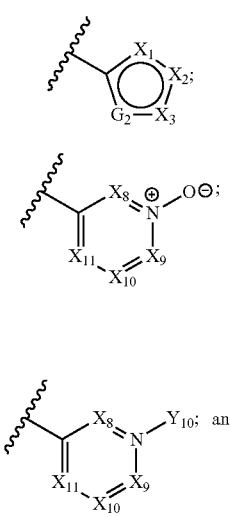

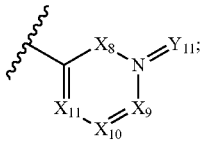

wherein:
G$_2$ is N=, =N, or —N(R$^{3'}$), wherein:
each occurrence of R$^3$ and R$^{3'}$ is independently hydrogen or an optionally substituted C$_{1-6}$ aliphatic, wherein:
X$_1$, X$_2$, and X$_3$, are each independently N, NR$^{3'}$, O, S, or CR$^4$, provided that only one of X$_1$, X$_2$, or X$_3$ may be O, S, or NR$^{3'}$;
X$_8$, X$_9$, X$_{10}$, and X$_{11}$ are each independently N, or CR$^4$, provided no more than two occurrences of X$_8$, X$_9$, X$_{10}$, and X$_{11}$ are N;
each occurrence of R$^4$ is independently hydrogen, —CN, halogen, —Z$_3$—R$^6$, or an optionally
substituted group selected from C$_{1-6}$ aliphatic, or 3-10-membered cycloaliphatic,
wherein:
Z$_3$ is selected from an optionally substituted C$_{1-3}$ alkylene chain, —O—, —N(R$^{4a}$)—, —S—, —S(O)—, —S(O)$_2$—, —C(O)—, —CO$_2$—, —C(O)NR$^{4a}$—, —N(R$^{4a}$)C(O)—, —N(R$^{4a}$)CO$_2$—, —S(O)$_2$NR$^{4a}$—, —N(R$^{4a}$)S(O)$_2$—, —OC(O)N(R$^{4a}$)—, —N(R$^{4a}$)C(O)NR$^{4a}$—, —N(R$^{4a}$)S(O)$_2$N(R$^{4a}$)—, or —OC(O)—;
R$^{4a}$ is hydrogen or an optionally substituted C$_{1-4}$ aliphatic, and
R$^6$ is hydrogen or an optionally substituted group selected from C$_{1-6}$ aliphatic,
3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;
or wherein two adjacent occurrences of R$^{3'}$ or R$^4$, taken together with the atom to which they are bound, form an optionally substituted fused group selected from 5-6-membered aryl, or 5-6-membered heteroaryl having 1-5 heteroatoms independently selected from nitrogen, oxygen, or sulfur;
Y$_{10}$ is —OR$^{4'}$ or —N(R$^{4'}$)$_2$;
Y$_{11}$ is O or N—R$^{4t}$;
each occurrence of R$^{4'}$ is independently hydrogen or an optionally substituted C$_{1-6}$ aliphatic;
Ring A is a group selected from 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;
each occurrence of R$^2$ is independently —R$^{12a}$, -T$_2$-R$^{12d}$, or —V$_2$-T$_2$-R$^{12d}$, and:
each occurrence of R$^{12a}$ is independently halogen, —CN, —NO$_2$, —R$^{12c}$, —N(R$^{12b}$)$_2$, —OR$^{12b}$, —SR$^{12c}$, —S(O)$_2$R$^{12c}$, —C(O)R$^{12b}$, —C(O)OR$^{12b}$, —C(O)N(R$^{12b}$)$_2$, —S(O)$_2$N(R$^{12b}$)$_2$, —OC(O)N(R$^{12b}$)$_2$, N(R$^{12e}$)C(O)R$^{12b}$, —N(R$^{12e}$)SO$_2$R$^{12c}$, —N(R$^{12e}$)C(O)OR$^{12b}$, —N(R$^{12e}$)C(O)N(R$^{12b}$)$_2$, or —N(R$^{12e}$)SO$_2$N(R$^{12b}$)$_2$, or two occurrences of R$^{12b}$, taken together with a nitrogen atom to which they are bound, form an optionally substituted 4-7-membered heterocyclyl ring having 0-1 additional heteroatoms selected from nitrogen, oxygen, or sulfur;

each occurrence of $R^{12b}$ is independently hydrogen or an optionally substituted group selected from $C_1$-$C_6$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{12c}$ is independently an optionally substituted group selected from $C_1$-$C_6$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{12d}$ is independently hydrogen or an optionally substituted from 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{12e}$ is independently hydrogen or an optionally substituted $C_{1-6}$ aliphatic group;

each occurrence of $V_2$ is independently —N($R^{12e}$)—, —O—, —S—, —S(O)—, —S(O)$_2$—, —C(O)—, —C(O)O—, —C(O)N($R^{12e}$)—, —S(O)$_2$N($R^{12e}$)—, —OC(O)N($R^{12e}$)—, —N($R^{12e}$)C(O)—, —N($R^{12e}$)SO$_2$—, —N($R^{12e}$)C(O)O—, —N($R^{12e}$)C(O)N($R^{12e}$)—, —N($R^{12e}$)—, —OC(O)—, or —C(O)N($R^{12e}$)—O—; and $T_2$ is an optionally substituted $C_1$-$C_6$ alkylene chain wherein the alkylene chain optionally is interrupted by —N($R^{13}$)—, —O—, —S—, —S(O)—, —S(O)$_2$—, —C(O)—, —C(O)O—, —C(O)N($R^{13}$)—, —S(O)$_2$N($R^{13}$)—, —OC(O)N($R^{13}$)—, —N($R^{13}$)C(O)—, —N($R^{13}$)SO$_2$—, —N($R^{13}$)C(O)O—, —N($R^{13}$)C(O)N($R^{13}$)—, —N($R^{13}$)S(O)$_2$N($R^{13}$)—, —OC(O)—, or —C(O)N($R^{13}$)—O— or wherein $T_3$ or a portion thereof optionally forms part of an optionally substituted 3-7 membered cycloaliphatic or heterocyclyl ring, wherein $R^{13}$ is hydrogen or an optionally substituted $C_1$-$C_4$ aliphatic group;

n is 0 to 4;

W is selected from —C($R^7$)$_2$—, —C(=C($R^7$)$_2$)—, —C($R^7$)$_2$O—, —C($R^7$)$_2$N$R^{7a}$—, —N($R^{7b}$)—, —S—, —S(O)—, —S(O)$_2$—, —C(O)—, —C(O)N$R^{7a}$—, or —N($R^{7a}$)C(O)—, wherein:

each occurrence of $R^7$ is independently hydrogen, or an optionally substituted group selected from $C_{1-6}$ aliphatic, 6-10-membered aryl, 5-10-membered heteroaryl having 1-5 heteroatoms independently selected from nitrogen, oxygen, or sulfur, —N($R^{7b}$)$_2$, —O$R^{7a}$, —S$R^{7a}$, halo, or —CN;

each occurrence of $R^{7a}$ is independently hydrogen or optionally substituted $C_{1-6}$ aliphatic;

each occurrence of $R^{7b}$ is independently hydrogen, optionally substituted $C_{1-6}$ aliphatic, —C(O)$R^{7a}$, or —S(O)$_2$$R^{7a}$; or wherein any two occurrences of $R^7$, $R^{7a}$, or $R^{7b}$ taken together with the atom to which they are bound, form an optionally substituted group selected from a 3-6-membered cycloaliphatic ring, 6-10-membered aryl, 3-6-membered heterocyclyl having 1-5 heteroatoms independently selected from nitrogen, oxygen, or sulfur, or 5-10-membered heteroaryl having 1-5 heteroatoms independently selected from nitrogen, oxygen, or sulfur;

or wherein any two occurrences of $R^{7a}$ and $R^2$, or $R^{7b}$ and $R^2$ taken together with the nitrogen atom to which they are bound, form an optionally substituted group selected from 3-6-membered heterocyclyl having 1-5 heteroatoms independently selected from nitrogen, oxygen, or sulfur, or 5-10-membered heteroaryl having 1-5 heteroatoms independently selected from nitrogen, oxygen, or sulfur;

$G_1$ is N or —C$R^8$, wherein $R^8$ is H, —CN, halogen, -Z-$R^9$, $C_{1-6}$ aliphatic, or 3-10-membered cycloaliphatic, wherein:

Z is selected from an optionally substituted $C_{1-3}$ alkylene chain, —O—, —N($R^{8a}$)—, —S—, —S(O)—, S(O)$_2$—, —C(O)—, —CO$_2$—, —C(O)N$R^{8a}$—, —N($R^{8a}$)C(O)—, —N($R^{8a}$)CO$_2$—, —S(O)$_2$N$R^{8a}$—, —N($R^{8a}$)S(O)$_2$—, —OC(O)N($R^{8a}$)—, —N($R^{8a}$)C(O)N$R^{8a}$—, —N($R^{8a}$)S(O)$_2$N($R^{8a}$)—, or —OC(O)—;

$R^{8a}$ is hydrogen or an optionally substituted $C_{1-4}$ aliphatic, and $R^9$ is hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur; and HY is an optionally substituted group selected from:

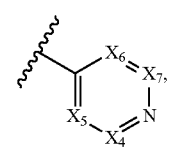

A

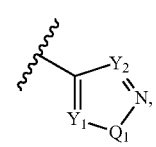

B

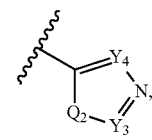

C

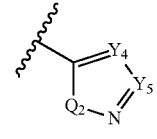

D

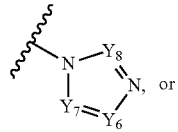

E

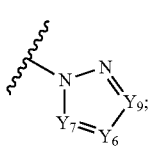

wherein each occurrence of $X_4$, $X_5$, $X_6$, and $X_7$ is independently —$CR^{10}$ or N, provided no more than two occurrences of $X_4$, $X_5$, $X_6$, and $X_7$ are N;

each occurrence of $Q_1$ and $Q_2$ is independently S, O or —$NR^5$;

each occurrence of $Y_1$, $Y_2$, $Y_3$, $Y_4$, $Y_5$, $Y_6$, $Y_7$, $Y_8$, and $Y_9$ is independently —$CR^{10}$ or N, provided no more than two occurrences of $Y_6$, $Y_7$, $Y_8$, and $Y_9$ are N;

or wherein two adjacent occurrences of $X_4$ and $X_5$, $X_6$ and $X_7$, $Y_1$ and $Q_1$, $Y_3$ and $Q_2$, or $Y_4$ and $Y_5$ taken together with the atom to which they are bound, form an optionally substituted fused group selected from 5-6-membered aryl, or 5-6-membered heteroaryl having 1-5 heteroatoms independently selected from nitrogen, oxygen, or sulfur;

wherein $R^{10}$ is —$R^{10b}$, —$V_1$—$R^{10c}$, -$T_1$-$R^{10b}$, or —$V_1$-$T_1$-$R^{10b}$ wherein:

$V_1$ is —$NR^{11}$—, —$NR^{11}$—C(O)—, —$NR^{11}$—C(S)—, —$NR^{11}$—C($NR^{11}$)—, —$NR^{11}$C(O)$OR^{10a}$—, —$NR^{11}$C(O)$NR^{11}$—, —$NR^{11}$C(O)$SR^{10a}$—, —$NR^{11}$C(S)$OR^{10a}$—, —$NR^{11}$C(S)$NR^{11}$—, —$NR^{11}$C(S)$SR^{10a}$—, —$NR^{11}$C($NR^{11}$)$OR^{10a}$—, —$NR^{11}$C($NR^{11}$)$NR^{11}$—, —$NR^{11}$S(O)$_2$—, —$NR^{11}$S(O)$_2$$NR^{11}$—, —C(O)—, —$CO_2$—, —C(O)$NR^{11}$—, —C(O)$NR^{11}$O—, —$SO_2$—, or —$SO_2NR^{11}$—;

each occurrence of $R^{10a}$ is independently hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

$T_1$ is an optionally substituted $C_1$-$C_6$ alkylene chain wherein the alkylene chain optionally is interrupted by —N($R^{11}$)—, —O—, —S—, —S(O)—, —S(O)$_2$—, —C(O)—, —C(O)O—, —C(O)N($R^{11}$)—, —S(O)$_2$N($R^{11}$)—, —OC(O)N($R^{11}$)—, —N($R^{11}$)C(O)—, —N($R^{11}$)SO$_2$—, —N($R_{11a}$)C(O)O—, —$NR^{10a}$C(O)N($R^{10a}$)—, —N($R^{10a}$)S(O)$_2$N($R^{10a}$)—, —OC(O)—, or —C(O)N($R^{11}$)—O— or wherein $T_1$ forms part of an optionally substituted 3-7 membered cycloaliphatic or heterocyclyl ring;

each occurrence of $R^{10b}$ is independently hydrogen, halogen, —CN, —$NO_2$, N($R^{11}$)$_2$, —$OR^{10a}$, —S(O)$_2R^{10a}$, —C(O)$R^{10a}$, —C(O)$OR^{10a}$, —C(O)N($R^{11}$)$_2$, —S(O)$_2$N($R^{11}$)$_2$, —OC(O)N($R^{11}$)$_2$, —N($R^{11}$)C(O)$R^{10a}$, —N($R^{11}$)SO$_2R^{10a}$, —N($R^{11}$)C(O)$OR^{10a}$, —N($R^{11}$)C(O)N($R^{11}$)$_2$, or —N($R^{11}$)SO$_2$N($R^{11}$)$_2$, or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{10c}$ is independently hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur, or $R^{10a}$ and $R^{10c}$ taken together with a nitrogen atom to which they are bound form an optionally substituted 4-7-membered heterocyclyl ring having 0-1 additional heteroatoms independently selected from nitrogen, oxygen, or sulfur;

each occurrence of $R^{11}$ is independently hydrogen, —C(O)$R^{11a}$, —$CO_2R^{11a}$, —C(O)N($R^{11a}$)$_2$, —C(O)N($R^{11a}$)—$OR^{11a}$, —S(O)$_2R^{11a}$, —S(O)$_2$N($R^{11a}$)$_2$, or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

wherein each occurrence of $R^{11a}$ is independently hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^5$ is independently hydrogen, —C(O)$R^{5a}$, —$CO_2R^{5a}$, —C(O)N($R^{5b}$)$_2$, —S(O)$_2R^{5a}$, —S(O)$_2$N($R^{5b}$)$_2$, or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

wherein each occurrence of $R^{11a}$ is independently hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

wherein each occurrence of $R^{5b}$ is independently hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur; or two occurrences of $R^{5b}$ taken together with the nitrogen atom to which they are bound, form an optionally substituted group selected from 3-6-membered heterocyclyl having 1-5 heteroatoms independently selected from nitrogen, oxygen, or sulfur, or 5-10-membered heteroaryl having 1-5 heteroatoms independently selected from nitrogen, oxygen, or sulfur;

provided that:

a. when $G_1$ is N, W is NH, and $R^1$ is $CONH_2$, then HY is other than optionally substituted 4,5,6,7-tetrahydro-4-hydrazinylidene-1-H-indolyl, 4,5,6,7-tetrahydro-4-hydrazinylidene-1-H-indazolyl, a 4,5,6,7-tetrahydro-4-oxo-1H-indazol-1-yl, or a 4,5,6,7-tetrahydro-4-oxo-1H-indol-1-yl group; and b. the compound is other than 4-Oxazolecarboxamide, 2-(1H-indazol-4-yl)-5-[[4-(1-piperazinyl)phenyl]amino]-, 4-Oxazolecarboxamide, 2-(1H-indazol-4-yl)-

5-[[4-[4-(2,2,2-trifluoroacetyl)-1-piperazinyl]phenyl]amino]-, or 4-Oxazolecarboxamide, 2-(1H-indazol-4-yl)-5-[[4-(methylsulfonyl)phenyl]amino]-, 4-Oxazolecarboxamide, 2-(1H-indazol-4-yl)-5-[[4-(1-piperazinyl)phenyl]amino]-, 4-Oxazolecarboxamide, 2-(1H-indazol-4-yl)-5-[[4-[4-(2,2,2-trifluoroacetyl)-1-piperazinyl]phenyl]amino]-, or 4-Oxazolecarboxamide, 2-(1H-indazol-4-yl)-5-[[4-(methylsulfonyl)phenyl]amino]-.

In another aspect, the compounds of this invention are represented by formula IA or IB:

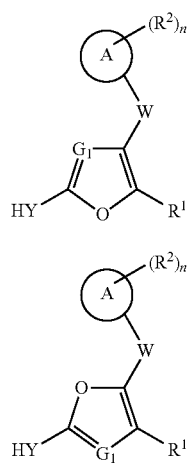

or a pharmaceutically acceptable salt thereof, wherein:
$R^1$ is CY, —C(O)N($R^3$)$_2$, —C(O)O$R^3$, —C(O)(NH)OH, —C(=NH)NHOH, —C(O)N$R^3$N($R^3$)$_2$, —C(=N—NH$_2$)NH$_2$, —C(=N)N($R^3$)$_2$, wherein:
CY is

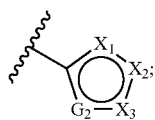

wherein:
$G_2$ is N=, =N, or —N($R^{3'}$), wherein:
each occurrence of $R^3$ and $R^{3'}$ is independently hydrogen or an optionally substituted $C_{1-6}$ aliphatic, wherein:
$X_1$, $X_2$, and $X_3$, are each independently N, N$R^{3'}$, O, S, or C$R^4$, provided that only one of $X_1$, $X_2$, or $X_3$ may be O, S, or N$R^{3'}$;
each occurrence of $R^4$ is independently hydrogen, —CN, halogen, -$Z_3$-$R^6$, or an optionally substituted group selected from $C_{1-6}$ aliphatic, or 3-10-membered cycloaliphatic, wherein:
$Z_3$ is selected from an optionally substituted $C_{1-3}$ alkylene chain, —O—, —N($R^{4a}$)—, —S—, —S(O)—, —S(O)$_2$—, —C(O)—, —C$_2$—, —C(O)N$R^{4a}$—, —N($R^{4a}$)C(O)—, —N($R^{4a}$)CO$_2$—, —S(O)$_2$N$R^{4a}$—, —N($R^{4a}$)S(O)$_2$—, —OC(O)N($R^{4a}$)—, —N($R^{4a}$)C(O)N$R^{4a}$—, —N$R^{4a}$)S(O)$_2$N($R^{4a}$)—, or —OC(O)—;
$R^{4a}$ is hydrogen or an optionally substituted $C_{1-4}$ aliphatic, and $R^6$ is hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;
or wherein two adjacent occurrences of $R^{3'}$ or $R^4$, taken together with the atom to which they are bound, form an optionally substituted fused group selected from 5-6-membered aryl, or 5-6-membered heteroaryl having 1-5 heteroatoms independently selected from nitrogen, oxygen, or sulfur;

Ring A is a group selected from 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;
each occurrence of $R^2$ is independently —$R^{12a}$, -$T_2$-$R^{12d}$, or $V_2$-$T_2$-$R^{12d}$, and:
each occurrence of $R^{12a}$ is independently halogen, —CN, —NO$_2$, —$R^{12c}$, —N($R^{12b}$)$_2$, —O$R^{12c}$, —S(O)$_2$$R^{12c}$, —C(O)$R^{12b}$, —C(O)O$R^{12b}$, —C(O)N($R^{12b}$)$_2$, —S(O)$_2$N($R^{12b}$)$_2$, —OC(O)N($R^{12b}$)$_2$, —N($R^{12e}$)C(O)$R^{12b}$, —N($R^{12e}$)SO$_2$$R^{12c}$, —N($R^{12e}$)C(O)O$R^{12b}$, —N($R^{12e}$)C(O)N($R^{12b}$)$_2$, or —N($R^{12e}$)SO$_2$N($R^{12b}$)$_2$, or two occurrences of $R^{12b}$, taken together with a nitrogen atom to which they are bound, form an optionally substituted 4-7-membered heterocyclyl ring having 0-1 additional heteroatoms selected from nitrogen, oxygen, or sulfur;
each occurrence of $R^{12b}$ is independently hydrogen or an optionally substituted group selected from $C_1$-$C_6$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;
each occurrence of $R^{12c}$ is independently an optionally substituted group selected from $C_1$-$C_6$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;
each occurrence of $R^{12d}$ is independently hydrogen or an optionally substituted from 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;
each occurrence of $R^{12e}$ is independently hydrogen or an optionally substituted $C_{1-6}$ aliphatic group;
each occurrence of $V_2$ is independently —N($R^{12e}$)—, —O—, —S—, —S(O)—, —S(O)$_2$—, —C(O)—, —C(O)O—, —C(O)N($R^{12e}$)—, —S(O)$_2$N($R^{12e}$)—, —OC(O)N($R^{12}$)—, —N($R^{12e}$)C(O)—, —N($R^{12e}$)SO$_2$—, —N($R^{12e}$)C(O)O—, —N($R^{12e}$)C(O)N($R^{12e}$)—, —N($R^{12e}$)SO$_2$N($R^{12e}$)—, —OC(O)—, or —C(O)N($R^{12e}$)—O—; and
$T_2$ is an optionally substituted $C_1$-$C_6$ alkylene chain wherein the alkylene chain optionally is interrupted by —N($R^{13}$)—, —O—, —S—, —S(O)—, —S(O)$_2$—, —C(O)—, —C(O)O—, —C(O)N($R^{13}$)—, —S(O)$_2$N($R^{13}$)—, —OC(O)N($R^{13}$)—, —N($R^{13}$)C(O)—, —N($R^{13}$)

—SO$_2$—, —N(R$^{13}$)C(O)O—, —N(R$^{13}$)C(O)N(R$^{13}$)—, —N(R$^{13}$)S(O)$_2$N(R$^{13}$)—, —OC(O)—, or —C(O)N(R$^{13}$)—O— or wherein T$_3$ or a portion thereof optionally forms part of an optionally substituted 3-7 membered cycloaliphatic or heterocyclyl ring, wherein R$^{13}$ is hydrogen or an optionally substituted C$_{1-4}$aliphatic group;

n is 0 to 4;

W is selected from —C(R$^7$)$_2$—, —C(=C(R$^7$)$_2$)—, —C(R$^7$)$_2$O—, —C(R$^7$)$_2$NR$^{7a}$—, —O—, —N(R$^{7b}$)—, —S—, —S(O)—, —S(O)$_2$—, —C(O)—, —C(O)NR$^{7a}$—, or —N(R$^{7a}$)C(O)—, wherein:

each occurrence of R$^7$ is independently hydrogen, or an optionally substituted group selected from C$_{1-6}$ aliphatic, 6-10-membered aryl, 5-10-membered heteroaryl having 1-5 heteroatoms independently selected from nitrogen, oxygen, or sulfur, —N(R$^{7b}$)$_2$, —SR$^{7a}$, halo, or —CN;

each occurrence of R$^{7a}$ is independently hydrogen or optionally substituted C$_{1-6}$ aliphatic;

each occurrence of R$^{7b}$ is independently hydrogen, optionally substituted C$_{1-6}$ aliphatic, —C(O)R$^{7a}$, or —S(O)$_2$R$^{7a}$; or wherein any two occurrences of R$^7$, R$^{7a}$, or R$^{7b}$ taken together with the atom to which they are bound, form an optionally substituted group selected from a 3-6-membered cycloaliphatic ring, 6-10-membered aryl, 3-6-membered heterocyclyl having 1-5 heteroatoms independently selected from nitrogen, oxygen, or sulfur, or 5-10-membered heteroaryl having 1-5 heteroatoms independently selected from nitrogen, oxygen, or sulfur;

or wherein any two occurrences of R$^{7a}$ and R$^2$, or R$^{7b}$ and R$^2$ taken together with the nitrogen atom to which they are bound, form an optionally substituted group selected from 3-6-membered heterocyclyl having 1-5 heteroatoms independently selected from nitrogen, oxygen, or sulfur, or 5-10-membered heteroaryl having 1-5 heteroatoms independently selected from nitrogen, oxygen, or sulfur;

G$_1$ is N or —CR$^8$, wherein R$^8$ is H, —CN, halogen, -Z-R$^9$, C$_{1-6}$ aliphatic, or 3-10-membered cycloaliphatic, wherein:

Z is selected from an optionally substituted C$_{1-3}$ alkylene chain, —O—, —N(R$^{8a}$)—, —S—, —S(O)—, S(O)$_2$—, —C(O)—, —CO$_2$—, —C(O)NR$^{8a}$—, —NR$^{8a}$C(O)—, —NR$^{8a}$CO$_2$—, —S(O)$_2$NR$^{8a}$—, NR$^{8a}$S(O)$_2$—, —OC(O)N(R$^{8a}$)—, —N(R$^{8a}$)C(O)NR$^{8a}$—, —N(R$^{8a}$)S(O)$_2$N(R$^{8a}$)—, or —OC(O)—;

R$^{8a}$ is hydrogen or an optionally substituted C$_{1-4}$ aliphatic, and

R$^9$ is hydrogen or an optionally substituted group selected from C$_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur; and HY is an optionally substituted group selected from:

A

B

C

D

E

F wherein each occurrence of X$_4$, X$_5$, X$_6$, and X$_7$ is independently —CR$^{10}$ or N, provided no more than two occurrences of X$_4$, X$_5$, X$_6$, and X$_7$ are N;

each occurrence of Q$_1$ and Q$_2$ is independently S, O or —NR$^5$;

each occurrence of Y$_1$, Y$_2$, Y$_3$, Y$_4$, Y$_5$, Y$_6$, Y$_7$, Y$_8$, and Y$_9$ is independently —CR$^{10}$ or N, provided no more than two occurrences of Y$_6$, Y$_7$, Y$_8$, and Y$_9$ are N;

or wherein two adjacent occurrences of X$_4$ and X$_5$, X$_6$ and X$_7$, Y$_1$ and Q', Y$_3$ and Q2, or Y$_4$ and Y$_5$ taken together with the atom to which they are bound, form an optionally substituted fused group selected from 5-6-membered aryl, or 5-6-membered heteroaryl having 1-5 heteroatoms independently selected from nitrogen, oxygen, or sulfur;

wherein R$^{10}$ is —R$^{10b}$, —V$_1$—R$^{10c}$, -T$_1$-R$^{10b}$, or —V$_1$-T$_1$-R$^{10b}$ wherein:

V$_1$ is —NR$^{11}$—, —NR$^{11}$—C(O)—, —NR$^{11}$—C(S)—, —NR$^{11}$—C(NR$^{11}$)—, —NR$^{11}$C(O)OR$^{10a}$—, —NR$^{11}$C(O)NR$^{11}$—, —NR$^{11}$C(O)SR$^{10a}$—, —NR$^{11}$C(S)OR$^{10a}$—, —NR$^{11}$C(S)NR$^{11}$—, —NR$^{11}$C(S)SR$^{10a}$—, —NR$^{11}$C(NR$^{11}$)OR$^{10a}$—, —NR$^{11}$C(NR$^{11}$)NR$^{11}$—, —NR$^{11}$S(O)$_2$—, —NR$^{11}$S(O)$_2$NR$^{11}$—, —C(O)—, —CO$_2$—, —C(O)NR$^{11}$, —C(O)NR$^{11}$O—, —SO$_2$—, or —SO$_2$NR$^{11}$—;

each occurrence of R$^{10a}$ is independently hydrogen or an optionally substituted group selected from C$_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

T$_1$ is an optionally substituted C$_1$-C$_6$alkylene chain wherein the alkylene chain optionally is interrupted by —N(R$^{11}$)—, —O—, —S—, —S(O)—, —S(O)$_2$—, —C(O)—, —C(O)O—, —C(O)N(R$^{11}$)—, —S(O)$_2$N(R$^{11}$)—, —OC(O)N(R$^{11}$)—, —N(R$^{11}$)C(O)—, —N(R$^{11}$)SO$_2$—, —N(R$^{11a}$)C(O) O—, —NR$^{10a}$C(O)N(R$^{10a}$)—, —N(R$^{10a}$)S(O)$_2$N(R$^{10a}$)—, —OC(O)—, or —C(O)N(R$^{11}$)—O— or wherein T$_1$ forms part of an optionally substituted 3-7 membered cycloaliphatic or heterocyclyl ring;

each occurrence of R$^{10b}$ is independently hydrogen, halogen, —CN, —NO$_2$, —N(R$^{11}$)$_2$, —OR$^{10a}$, —SR$^{10a}$, —S(O)$_2$R$^{10a}$, —C(O)$_R$$^{10a}$, —C(O)R$^{10a}$, —C(O)N(R$^{11}$)$_2$, —S(O)$_2$N(R$^{11}$)$_2$, —OC(O)N(R$^{11}$)$_2$, —N(R$^{11}$)C(O)R$^{10a}$, —N(R$^{11}$)SO$_2$R$^{10a}$, —N(R$^{11}$)C(O)OR$^{10a}$, —N(R$^{11}$)C(O)N(R$^{11}$)$_2$, or —N(R$^{11}$)SO$_2$N(R$^{11}$)$_2$, or an optionally substituted group selected from C$_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of R$^{10c}$ is independently hydrogen or an optionally substituted group selected from C$_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur, or R$^{10a}$ and R$^{10c}$ taken together with a nitrogen atom to which they are bound form an optionally substituted 4-7-membered heterocyclyl ring having 0-1 additional heteroatoms independently selected from nitrogen, oxygen, or sulfur;

each occurrence of R$^{11}$ is independently hydrogen, —C(O)R$^{11a}$, —CO$_2$R$^{11a}$, —C(O)N(R$^{11a}$)$_2$, —C(O)N(R$^{11a}$)—OR$^{11a}$, —SO$_2$R$^{11a}$, —SO$_2$N(R$^{11a}$)$_2$, or an optionally substituted group selected from C$_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

wherein each occurrence of R$^{11a}$ is independently hydrogen or an optionally substituted group selected from C$_{1-6}$aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of R$^5$ is independently hydrogen, —C(O)R$^{5a}$, —CO$_2$R$^{5a}$, —C(O)N(R$^{5b}$)$_2$, —SO$_2$R$^{5a}$, —SO$_2$N(R$^{5b}$)$_2$, or an optionally substituted group selected from C$_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

wherein each occurrence of R$^{5a}$ is independently hydrogen or an optionally substituted group selected from C$_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

wherein each occurrence of R$^{5b}$ is independently hydrogen or an optionally substituted group selected from C$_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur; or two occurrences of R$^{5b}$ taken together with the nitrogen atom to which they are bound, form an optionally substituted group selected from 3-6-membered heterocyclyl having 1-5 heteroatoms independently selected from nitrogen, oxygen, or sulfur, or 5-10-membered heteroaryl having 1-5 heteroatoms independently selected from nitrogen, oxygen, or sulfur;

provided that:
a. when G$_1$ is N, W is NH, and R$^1$ is CONH$_2$, then HY is other than optionally substituted 4,5,6,7-tetrahydro-4-hydrazinylidene-1-H-indolyl, 4,5,6,7-tetrahydro-4-hydrazinylidene-1-H-indazolyl, a 4,5,6,7-tetrahydro-4-oxo-1H-indazol-1-yl, or a 4,5,6,7-tetrahydro-4-oxo-1H-indol-1-yl group; and
b. the compound is other than 4-Oxazolecarboxamide, 2-(1H-indazol-4-yl)-5-[[4-(1-piperazinyl)phenyl]amino]-, 4-Oxazolecarboxamide, 2-(1H-indazol-4-yl)-5-[[4-[4-(2,2,2-trifluoroacetyl)-1-piperazinyl]phenyl]amino]-, or 4-Oxazolecarboxamide, 2-(1H-indazol-4-yl)-5-[[4-(methylsulfonyl)phenyl]amino]-, 4-Oxazolecarboxamide, 2-(1H-indazol-4-yl)-5-[[4-(1-piperazinyl)phenyl]amino]-, 4-Oxazolecarboxamide, 2-(1H-indazol-4-yl)-5-[[4-[4-(2,2,2-trifluoroacetyl)-1-piperazinyl]phenyl]amino]-, or 4-Oxazolecarboxamide, 2-(1H-indazol-4-yl)-5-[[4-(methylsulfonyl)phenyl]amino]-

In another aspect, the compounds of this invention are represented by formula IA or IB:

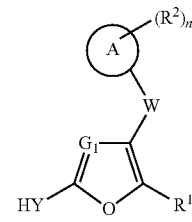

IA

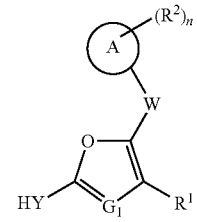

IB or a pharmaceutically acceptable salt thereof, wherein:
R$^1$ is —C(O)N(R$^3$)$_2$, —C(O)OR$^3$, —C(O)(NH)OH, —C(=NH)NHOH, —C(O)NR$^3$N(R$^3$)$_2$, —C(=N—NH$_2$)NH$_2$, —C(=N)N(R$^3$)$_2$;

each occurrence of R$^3$ is independently hydrogen or an optionally substituted C$_{1-6}$ aliphatic;

Ring A is a group selected from 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^2$ is independently —$R^{12a}$, -$T_2$-$R^{12d}$, or —$V_2$-$T_2$-$R^{12d}$, and:

each occurrence of $R^{12a}$ is independently halogen, —CN, —$NO_2$, —$R^{12c}$, —$N(R^{12b})_2$, —$OR^{12b}$, —$SR^{12c}$, —$S(O)_2R^{12c}$, —$C(O)R^{12b}$, —$C(O)OR^{12b}$, —$C(O)N(R^{12})_2$, —$S(O)_2N(R^{12b})_2$, —$OC(O)NR^{12b})_2$, —$N(R^{12e})C(O)R^{12b}$, —$N(R^{12c})SO_2R^{12c}$, —$N(R^{12e})C(O)OR^{12b}$, —$N(R^{12e})C(O)N(R^{12b})_2$, or —$N(R^{12e})SO_2N(R^{12b})_2$, or two occurrences of $R^{12b}$, taken together with a nitrogen atom to which they are bound, form an optionally substituted 4-7-membered heterocyclyl ring having 0-1 additional heteroatoms selected from nitrogen, oxygen, or sulfur;

each occurrence of $R^{12b}$ is independently hydrogen or an optionally substituted group selected from $C_1$-$C_6$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{12c}$ is independently an optionally substituted group selected from $C_1$-$C_6$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{12d}$ is independently hydrogen or an optionally substituted from 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{12e}$ is independently hydrogen or an optionally substituted $C_{1-6}$ aliphatic group;

each occurrence of $V_2$ is independently —$N(R^{12e})$—, —O—, —S—, —S(O)—, —$S(O)_2$—, —C(O)—, —C(O)O—, —$C(O)N(R^{12e})$—, —$S(O)_2N(R^{12e})$—, —$OC(O)N(R^{12e})$—, —$N(R^{12e})C(O)$—, —$N(R^{12e})SO_2$—, —$N(R^{12e})C(O)O$—, —$N(R^{12e})C(O)N(R^{12e})$, —$N(R^{12e})SO_2N(R^{12e})$—, —OC(O)—, or —$C(O)N(R^{12e})$—O—; and $T_2$ is an optionally substituted $C_1$-$C_6$ alkylene chain wherein the alkylene chain optionally is interrupted by —$N(R^{13})$—, —O—, —S—, —S(O)—, —$S(O)_2$—, —C(O)—, —C(O)O—, —$C(O)N(R^{13})$—, —$S(O)_2N(R^{13})$—, —$OC(O)N(R^{13})$—, —$N(R^{13})C(O)$—, —$N(R^{13})SO_2$—, —$N(R^{13})C(O)O$—, —$N(R^{13})C(O)N(R^{13})$—, —$N(R^{13})S(O)_2N(R^{13})$—, —OC(O)—, or —$C(O)N(R^{13})$—O— or wherein $T_3$ or a portion thereof optionally forms part of an optionally substituted 3-7 membered cycloaliphatic or heterocyclyl ring, wherein $R^{13}$ is hydrogen or an optionally substituted $C_{1-4}$ aliphatic group;

n is 0 to 4;

W is selected from —$C(R^7)_2$—, —$C(=C(R^7)_2)$—, —$C(R^7)_2O$—, —$C(R^7)_2NR^{7a}$—, —O—, —$N(R^{7b})$—, —S—, —S(O)—, —$S(O)_2$—, —C(O)—, —$C(O)NR^{7a}$—, or —$N(R^{7a})C(O)$—, wherein:

each occurrence of $R^7$ is independently hydrogen, or an optionally substituted group selected from $C_{1-6}$ aliphatic, 6-10-membered aryl, 5-10-membered heteroaryl having 1-5 heteroatoms independently selected from nitrogen, oxygen, or sulfur, —$N(R^{7b})_2$, —$OR^{7a}$, —$SR^{7a}$, halo, or —CN;

each occurrence of $R^{7a}$ is independently hydrogen or optionally substituted $C_{1-6}$ aliphatic;

each occurrence of $R^{7b}$ is independently hydrogen, optionally substituted $C_{1-6}$ aliphatic, —$C(O)R^{7a}$, or —$S(O)_2R^{7a}$; or wherein any two occurrences of $R^7$, $R^{7a}$, or $R^{7b}$ taken together with the atom to which they are bound, form an optionally substituted group selected from a 3-6-membered cycloaliphatic ring, 6-10-membered aryl, 3-6-membered heterocyclyl having 1-5 heteroatoms independently selected from nitrogen, oxygen, or sulfur, or 5-10-membered heteroaryl having 1-5 heteroatoms independently selected from nitrogen, oxygen, or sulfur;

or wherein any two occurrences $R^{7a}$ and $R^2$, or $R^{7b}$ and $R^2$ taken together with the nitrogen atom to which they are bound, form an optionally substituted group selected from 3-6-membered heterocyclyl having 1-5 heteroatoms independently selected from nitrogen, oxygen, or sulfur, or 5-10-membered heteroaryl having 1-5 heteroatoms independently selected from nitrogen, oxygen, or sulfur;

$G_1$ is N or —$CR^8$, wherein $R^8$ is H, —CN, halogen, -Z-$R^9$, $C_{1-6}$ aliphatic, or 3-10-membered cycloaliphatic, wherein:

Z is selected from an optionally substituted $C_{1-3}$ alkylene chain, —O—, —$N(R^{8a})$—, —S—, —S(O)—, $S(O)_2$—, —C(O)—, —$CO_2$—, —$C(O)NR^{8a}$—, —$N(R^{8a})C(O)$—, —$N(R^{8a})CO_2$—, —$S(O)_2NR^{8a}$—, —$N(R^{8a})S(O)_2$—, —$OC(O)N(R^{8a})$—, —$N(R^{8a})C(O)NR^{8a}$—, —$N(R^{8a})S(O)_2N(R^{8a})$—, or —OC(O)—;

$R^{8a}$ is hydrogen or an optionally substituted $C_{1-4}$ aliphatic, and $R^9$ is hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur; and HY is

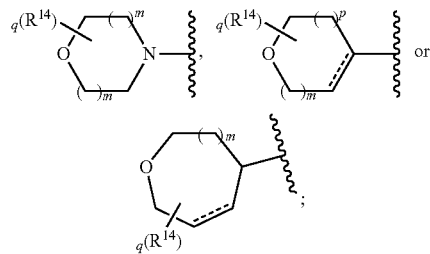

wherein each occurrence of $R^{14}$ is independently —$R^{14a}$ or -$T_1$-$R^{14d}$, wherein:

each occurrence of $R^{14a}$, as valency and stability permit, is independently fluorine, =O, =S, —CN, —$NO_2$, —$R^{14c}$, —$N(R^{14b})_2$, —$OR^{14b}$, —$SR^{14c}$, —$S(O)_2R^{14c}$, —$C(O)R^{14b}$, —$C(O)OR^{14b}$, —$C(O)N(R^{14b})_2$, —$S(O)_2N(R^{14b})_2$, —$OC(O)N(R^{14b})_2$, —$N(R^{14e})C(O)R^{14b}$, —$N(R^{14e})SO_2R^{14c}$, —$N(R^{14e})C(O)OR^{14b}$, —$N(R^{14e})C(O)N(R^{14b})_2$, or —$N(R^{14e})SO_2N(R^{14b})_2$, or two occurrences of $R^{14b}$, taken together with a nitrogen atom to which they are bound, form an optionally substituted 4-7-membered heterocyclyl ring having 0-1 additional heteroatoms selected from nitrogen, oxygen, or sulfur;

each occurrence of $R^{14b}$ is independently hydrogen or an optionally substituted group selected from $C_1$-$C_6$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{14c}$ is independently an optionally substituted group selected from $C_1$-$C_6$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{14d}$ is independently hydrogen or an optionally substituted from 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{14e}$ is independently hydrogen or an optionally substituted $C_{1-6}$ aliphatic group; and $T_1$ is an optionally substituted $C_1$-$C_6$ alkylene chain wherein the alkylene chain optionally is interrupted by —N($R^{14a}$)—, —O—, —S—, —S(O)—, —S(O)$_2$—, —C(O)—, —C(O)O—, —C(O)N($R^{14a}$)—, —S(O)$_2$N($R^{14a}$)—, —OC(O)N($R^{14a}$)—, —N($R^{14a}$)C(O)—, —N($R^{14a}$)SO$_2$—, —N($R^{14a}$)C(O)O—, —NR$^{14a}$ C(O)N($R^{14a}$)—, —N($R^{14a}$)S(O)$_2$N($R^{14a}$)—, —OC(O)—, or —C(O)N($R^{14a}$)—O— or wherein $T_1$ or a portion thereof optionally forms part of an optionally substituted 3-7 membered cycloaliphatic or heterocyclyl ring;

n is 0-6;

m is 1 or 2; and p is 0, 1, or 2.

In some embodiments for compounds described directly above, HY is

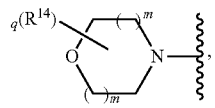

wherein both occurrences of m are 1.

In other embodiments for compounds described directly above, HY is

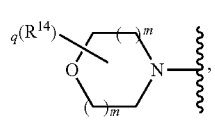

wherein both occurrences of m are 1, and $R^1$ is COOH.

In yet another aspect, the compounds of this invention are represented by formula IA or IB:

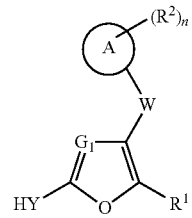

IA

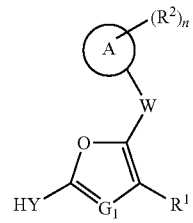

IB or a pharmaceutically acceptable salt thereof, wherein:
$R^1$ is CY, wherein:
CY is an optionally substituted group selected from:

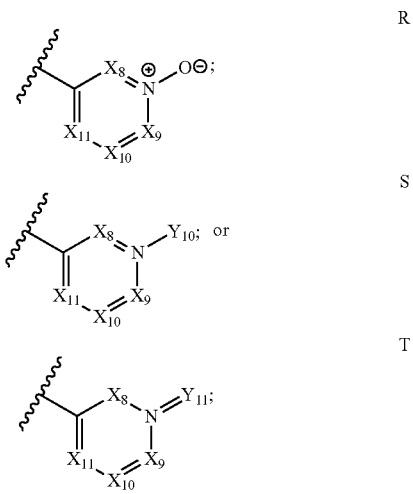

wherein:
each occurrence of $R^3$ is independently hydrogen or an optionally substituted $C_{1-6}$ aliphatic, wherein:
$X_8$, $X_9$, $X_{10}$, and $X_{11}$ are each independently N, or $CR^4$, provided no more than two occurrences of $X_8$, $X_9$, $X_{10}$, and $X_{11}$ are N;
each occurrence of $R^4$ is independently hydrogen, —CN, halogen, -$Z_3$—$R^6$, or an optionally substituted group selected from $C_{1-6}$ aliphatic, or 3-10-membered cycloaliphatic, wherein:
$Z_3$ is selected from an optionally substituted $C_{1-3}$ alkylene chain, —O—, —N($R^{4a}$)—, —S—, —S(O)—, —S(O)$_2$—, —C(O)—, —CO$_2$—, —C(O)NR$^{4a}$—, —N($R^{4a}$)C(O)—, —N($R^{4a}$)CO$_2$—, —S(O)$_2$NR$^{4a}$—, —N($R^{4a}$)S(O)$_2$—, —OC(O)N($R^{4a}$)—, —N($R^{4a}$)C(O)NR$^{4a}$—, —N($R^{4a}$)S(O)$_2$N($R^{4a}$)—, or —OC(O)—;
$R^{4a}$ is hydrogen or an optionally substituted $C_{1-4}$ aliphatic, and
$R^6$ is hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

$Y_{10}$ is —$OR^{4'}$ or —$N(R^{4'})_2$;

$Y_{11}$ is O or N—$R^{4t}$;

each occurrence of $R^{4'}$ is independently hydrogen or an optionally substituted $C_{1-6}$ aliphatic;

Ring A is a group selected from 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^2$ is independently $R^{12a}$, -$T_2$-$R^{12d}$, —$V_2$—$R^{12d}$, and:

each occurrence of $R^{12a}$ is independently halogen, —CN, —$NO_2$, —$R^{12c}$, —$N(R^{12b})_2$, —$OR^{12b}$, —$SR^{12c}$, —$S(O)_2R^{12c}$, —$C(O)R^{12b}$, —$C(O)OR^{12b}$, —$C(O)N(R^{12b})_2$, —$S(O)_2N(R^{12b})_2$, —$OC(O)N(R^{12b})_2$, —$N(R^{12e})C(O)R^{12b}$, —$N(R^{12e})SO_2R^{12c}$, —$N(R^{12e})C(O)OR^{12b}$, —$N(R^{12e})C(O)N(R^{12b})_2$, or —$N(R^{12e})SO_2N(R^{12b})_2$, or two occurrences of $R^{12b}$, taken together with a nitrogen atom to which they are bound, form an optionally substituted 4-7-membered heterocyclyl ring having 0-1 additional heteroatoms selected from nitrogen, oxygen, or sulfur;

each occurrence of $R^{12b}$ is independently hydrogen or an optionally substituted group selected from $C_1$-$C_6$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{12c}$ is independently an optionally substituted group selected from $C_1$-$C_6$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{12d}$ is independently hydrogen or an optionally substituted from 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{12e}$ is independently hydrogen or an optionally substituted $C_{1-6}$ aliphatic group;

each occurrence of $V_2$ is independently —$N(R^{12e})$—, —O—, —S—, —S(O)—, —$S(O)_2$—, —C(O)—, —C(O)O—, —$C(O)N(R^{12e})$—, —$S(O)_2N(R^{12e})$—, —$OC(O)N(R^{12e})$—, —$N(R^{12e})C(O)$—, —$N(R^{12e})SO_2$—, —$N(R^{12e})C(O)O$—, —$N(R^{12e})C(O)N(R^{12e})$—, —$N(R^{12e})SO_2N(R^{12e})$—, —OC(O)—, or —$C(O)N(R^{12e})$—O—; and $T_2$ is an optionally substituted $C_1$-$C_6$alkylene chain wherein the alkylene chain optionally is interrupted by —$N(R^{13})$—, —O—, —S—, —S(O)—, —$S(O)_2$—, —C(O)—, —C(O)O—, —$C(O)N(R^{13})$—, —$S(O)_2N(R^{13})$—, —$OC(O)N(R^{13})$—, —$N(R^{13})C(O)$—, —$N(R^{13})SO_2$—, —$N(R^{13})C(O)O$—, —$N(R^{13})C(O)N(R^{13})$—, —$N(R^{13})S(O)_2N(R^{13})$—, —OC(O)—, or —$C(O)N(R^{13})$—

O— or wherein $T_3$ or a portion thereof optionally forms part of an optionally substituted 3-7 membered cycloaliphatic or heterocyclyl ring, wherein $R^{13}$ is hydrogen or an optionally substituted $C_{1-4}$aliphatic group;

n is 0 to 4;

W is selected from —$C(R^7)_2$—, —$C(=C(R^7)_2)$—, —$C(R^7)_2O$—, —$C(R^7)_2NR^{7a}$—, —$N(R^{7b})$—, —S—, —S(O)—, —$S(O)_2$—, —C(O)—, —$C(O)NR^{7a}$—, or —$N(R^{7a})C(O)$—, wherein:

each occurrence of $R^7$ is independently hydrogen, or an optionally substituted group selected from $C_{1-6}$ aliphatic, 6-10-membered aryl, 5-10-membered heteroaryl having 1-5 heteroatoms independently selected from nitrogen, oxygen, or sulfur, —$N(R^{7b})_2$, —$OR^{7a}$, —$SR^{7a}$, halo, or —CN;

each occurrence of $R^{7a}$ is independently hydrogen or optionally substituted $C_{1-6}$ aliphatic;

each occurrence of $R^{7b}$ is independently hydrogen, optionally substituted $C_{1-6}$ aliphatic, —$C(O)R^{7a}$, or —$S(O)_2R^{7a}$; or wherein any two occurrences of $R^7$, $R^{7a}$, or $R^{7b}$ taken together with the atom to which they are bound, form an optionally substituted group selected from a 3-6-membered cycloaliphatic ring, 6-10-membered aryl, 3-6-membered heterocyclyl having 1-5 heteroatoms independently selected from nitrogen, oxygen, or sulfur, or 5-10-membered heteroaryl having 1-5 heteroatoms independently selected from nitrogen, oxygen, or sulfur;

or wherein any two occurrences of $R^{7a}$ and $R^2$, or $R^{7b}$ and $R^2$ taken together with the nitrogen atom to which they are bound, form an optionally substituted group selected from 3-6-membered heterocyclyl having 1-5 heteroatoms independently selected from nitrogen, oxygen, or sulfur, or 5-10-membered heteroaryl having 1-5 heteroatoms independently selected from nitrogen, oxygen, or sulfur;

$G_1$ is N or —$CR^8$, wherein $R^8$ is H, —CN, halogen, -Z-$R^9$, $C_{1-6}$ aliphatic, or 3-10-membered cycloaliphatic, wherein:

Z is selected from an optionally substituted $C_{1-3}$ alkylene chain, —O—, —$N(R^{8a})$—, —S—, —S(O)—, $S(O)_2$—, —C(O)—, —$CO_2$—, —$C(O)NR^{8a}$—, —$N(R^{8a})C(O)$—, —$N(R^{8a})CO_2$—, —$S(O)_2NR^{8a}$—, —$N(R^{8a})S(O)_2$—, —$OC(O)N(R^{8a})$—, —$N(R^{8a})C(O)NR^{8a}$—, —$N(R^{8a})S(O)_2N(R^{8a})$—, or —OC(O)—;

$R^{8a}$ is hydrogen or an optionally substituted $C_{1-4}$ aliphatic, and $R^9$ is hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur; and HY is

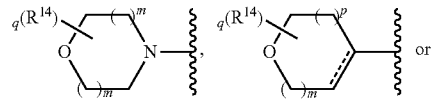

-continued

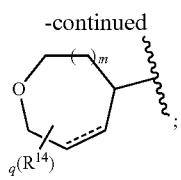

wherein each occurrence of $R^{14}$ is independently —$R^{14a}$ or -$T_1$-$R^{14d}$, wherein:

each occurrence of $R^{14a}$, as valency and stability permit, is independently fluorine, =O, =S, —CN, —$NO_2$, —$R^{14c}$, —$N(R^{14b})_2$, —$OR^{14b}$, —$SR^{14c}$, —$S(O)_2R^{14c}$, —$C(O)R^{14b}$, —$C(O)OR^{14b}$, —$C(O)N(R^{14b})_2$, —$S(O)_2N(R^{14b})_2$, —$OC(O)N(R^{14b})_2$, —$N(R^{14e})C(O)R^{14b}$, —$N(R^{14e})SO_2R^{14c}$, —$N(R^{14e})C(O)OR^{14b}$, —$N(R^{14e})C(O)N(R^{14b})_2$, or —$N(R^{14e})SO_2N(R^{14b})_2$, or two occurrences of $R^{14b}$, taken together with a nitrogen atom to which they are bound, form an optionally substituted 4-7-membered heterocyclyl ring having 0-1 additional heteroatoms selected from nitrogen, oxygen, or sulfur;

each occurrence of $R^{14b}$ is independently hydrogen or an optionally substituted group selected from $C_1$-$C_6$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{14c}$ is independently an optionally substituted group selected from $C_1$-$C_6$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{14d}$ is independently hydrogen or an optionally substituted from 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{14e}$ is independently hydrogen or an optionally substituted $C_{1-6}$ aliphatic group; and $T_1$ is an optionally substituted $C_1$-$C_6$ alkylene chain wherein the alkylene chain optionally is interrupted by —$N(R^{14a})$—, —O—, —S—, —S(O)—, —$S(O)_2$—, —C(O)—, —C(O)O—, —$C(O)N(R^{14a})$—, —$S(O)_2N(R^{14a})$—, —$OC(O)N(R^{14a})$—, —$N(R^{14a})C(O)$—, —$N(R^{14a})SO_2$—, —$N(R^{14a})C(O)O$—, —$NR^{14a}C(O)N(R^{14a})$—, —$N(R^{14a})S(O)_2N(R^{14a})$—, —OC(O)—, or —$C(O)N(R^{14a})$—O— or wherein $T_1$ or a portion thereof optionally forms part of an optionally substituted 3-7 membered cycloaliphatic or heterocyclyl ring;

n is 0-6;

m is 1 or 2;

p is 0, 1, or 2.

In some embodiments for compounds described directly above, $G_1$ is N.

In some embodiments for compounds described directly above, CY is

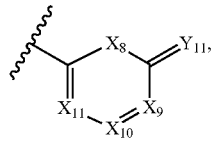

wherein $X_8$ and $X_{11}$ are N, $X_9$ and $X_{10}$ are $CR^4$, and $Y_{11}$ is O.

In some embodiments for compounds described directly above, HY is

wherein both occurrences of m are 1.

In some embodiments for compounds described directly above, HY is pyridyl optionally additionally substituted with one or more occurrences of $R^{10}$.

DETAILED DESCRIPTION OF THE INVENTION

2. Compounds and Definitions:

Compounds of this invention include those described generally for formula IA or IB above, and are further illustrated by the classes, subclasses, and species disclosed herein. It will be appreciated that preferred subsets described for each variable herein can be used for any of the structural subsets as well. As used herein, the following definitions shall apply unless otherwise indicated.

As described herein, compounds of the invention may be optionally substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, means that a hydrogen radical of the designated moiety is replaced with the radical of a specified substituent, provided that the substitution results in a stable or chemically feasible compound. The term "substitutable", when used in reference to a designated atom, means that attached to the atom is a hydrogen radical, which hydrogen atom can be replaced with the radical of a suitable substituent. Unless otherwise indicated, an "optionally substituted" group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds.

A stable compound or chemically feasible compound is one in which the chemical structure is not substantially altered when kept at a temperature from about 80° C. to about +40°, in the absence of moisture or other chemically reactive conditions, for at least a week, or a compound which maintains its integrity long enough to be useful for therapeutic or prophylactic administration to a patient.

The phrase "one or more substituents", as used herein, refers to a number of substituents that equals from one to the maximum number of substituents possible based on the number of available bonding sites, provided that the above conditions of stability and chemical feasibility are met.

As used herein, the term "independently selected" means that the same or different values may be selected for multiple instances of a given variable in a single compound.

As used herein, "a 3-7-membered saturated, partially unsaturated, or aromatic monocyclic ring having 0-3 heteroatoms independently selected from nitrogen, oxygen, or sulfur, or an 8-10-membered partially unsaturated, or aromatic bicyclic ring system having 0-5 heteroatoms independently selected from nitrogen, oxygen, or sulfur" includes cycloaliphatic, heterocyclic, aryl and heteroaryl rings.

As used herein, the term "aromatic" includes aryl and heteroaryl groups as described generally below and herein.

The term "aliphatic" or "aliphatic group", as used herein, means an optionally substituted straight-chain or branched $C_{1-12}$ hydrocarbon, or a cyclic $C_{1-12}$ hydrocarbon which is completely saturated or which contains one or more units of unsaturation, but which is not aromatic (also referred to herein as "carbocycle", "cycloaliphatic", "cycloalkyl", or "cycloalkenyl"). For example, suitable aliphatic groups include optionally substituted linear, branched or cyclic alkyl, alkenyl, alkynyl groups and hybrids thereof, such as (cycloalkyl)alkyl, (cycloalkenyl)alkyl, or (cycloalkyl)alkenyl. Unless otherwise specified, in various embodiments, aliphatic groups have 1-12, 1-10, 1-8, 1-6, 1-4, 1-3, or 1-2 carbon atoms.

The term "alkyl", used alone or as part of a larger moiety, refers to an optionally substituted straight or branched chain hydrocarbon group having 1-12, 1-10, 1-8, 1-6, 1-4, 1-3, or 1-2 carbon atoms.

The term "alkenyl", used alone or as part of a larger moiety, refers to an optionally substituted straight or branched chain hydrocarbon group having at least one double bond and having 2-12, 2-10, 2-8, 2-6, 2-4, or 2-3 carbon atoms.

The term "alkynyl", used alone or as part of a larger moiety, refers to an optionally substituted straight or branched chain hydrocarbon group having at least one triple bond and having 2-12, 2-10, 2-8, 2-6, 2-4, or 2-3 carbon atoms.

The terms "cycloaliphatic", "carbocycle", "carbocyclyl", "carbocyclo", or "carbocyclic", used alone or as part of a larger moiety, refer to an optionally substituted saturated or partially unsaturated cyclic aliphatic ring system having from 3 to about 14 ring carbon atoms. In some embodiments, the cycloaliphatic group is an optionally substituted monocyclic hydrocarbon having 3-8 or 3-6 ring carbon atoms. Cycloaliphatic groups include, without limitation, optionally substituted cyclopropyl, cyclobutyl, cyclopentyl, cyclopentenyl, cyclohexyl, cyclohexenyl, cycloheptyl, cycloheptenyl, cyclooctyl, cyclooctenyl, or cyclooctadienyl. The terms "cycloaliphatic", "carbocycle", "carbocyclyl", "carbocyclo", or "carbocyclic" also include optionally substituted bridged or fused bicyclic rings having 6-12, 6-10, or 6-8 ring carbon atoms, wherein any individual ring in the bicyclic system has 3-8 ring carbon atoms.

The term "cycloalkyl" refers to an optionally substituted saturated ring system of about 3 to about 10 ring carbon atoms. Exemplary monocyclic cycloalkyl rings include cyclopropyl, cyclobutyl, cyclopentyl, cyclohexyl, and cycloheptyl.

The term "cycloalkenyl" refers to an optionally substituted non-aromatic monocyclic or multicyclic ring system containing at least one carbon-carbon double bond and having about 3 to about 10 carbon atoms. Exemplary monocyclic cycloalkenyl rings include cyclopentyl, cyclohexenyl, and cycloheptenyl.

The terms "haloaliphatic", "haloalkyl", "haloalkenyl" and "haloalkoxy" refer to an aliphatic, alkyl, alkenyl or alkoxy group, as the case may be, which is substituted with one or more halogen atoms. As used herein, the term "halogen" or "halo" means F, Cl, Br, or I. The term "fluoroaliphatic" refers to a haloaliphatic wherein the halogen is fluoro, including perfluorinated aliphatic groups. Examples of fluoroaliphatic groups include, without limitation, fluoromethyl, difluoromethyl, trifluoromethyl, 2-fluoroethyl, 2,2,2-trifluoroethyl, 1,1,2-trifluoroethyl, 1,2,2-trifluoroethyl, and pentafluoroethyl.

The term "heteroatom" refers to one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The teems "aryl" and "ar-", used alone or as part of a larger moiety, e.g., "aralkyl", "aralkoxy", or "aryloxyalkyl", refer to an optionally substituted $C_{6-14}$ aromatic hydrocarbon moiety comprising one to three aromatic rings. Preferably, the aryl group is a $C_{6-10}$ aryl group. Aryl groups include, without limitation, optionally substituted phenyl, naphthyl, or anthracenyl. The terms "aryl" and "ar-", as used herein, also include groups in which an aryl ring is fused to one or more cycloaliphatic rings to form an optionally substituted cyclic structure such as a tetrahydronaphthyl, indenyl, or indanyl ring. The term "aryl" may be used interchangeably with the terms "aryl group", "aryl ring", and "aromatic ring".

An "aralkyl" or "arylalkyl" group comprises an aryl group covalently attached to an alkyl group, either of which independently is optionally substituted. Preferably, the aralkyl group is $C_{6-10}$ aryl$C_{1-6}$ alkyl, including, without limitation, benzyl, phenethyl, and naphthylmethyl.

The terms "heteroaryl" and "heteroar-", used alone or as part of a larger moiety, e.g., "heteroaralkyl", or "heteroaralkoxy", refer to groups having 5 to 14 ring atoms, preferably 5, 6, 9, or 10 ring atoms; having 6, 10, or 14 π electrons shared in a cyclic array; and having, in addition to carbon atoms, from one to five heteroatoms. A heteroaryl group may be mono-, bi-, tri-, or polycyclic, preferably mono-, bi-, or tricyclic, more preferably mono- or bicyclic. The term "heteroatom" refers to nitrogen, oxygen, or sulfur, and includes any oxidized form of nitrogen or sulfur, and any quaternized form of a basic nitrogen. For example, a nitrogen atom of a heteroaryl may be a basic nitrogen atom and may also be optionally oxidized to the corresponding N-oxide. When a heteroaryl is substituted by a hydroxy group, it also includes its corresponding tautomer. The terms "heteroaryl" and "heteroar-", as used herein, also include groups in which a heteroaromatic ring is fused to one or more aryl, cycloaliphatic, or heterocycloaliphatic rings. Nonlimiting examples of heteroaryl groups include thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, pteridinyl, indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle", "heterocyclyl", "heterocyclic radical", and "heterocyclic ring" are used interchangeably and refer to a stable 3- to 8-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or NR$^+$ (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, piperidinyl, decahydroquinolinyl, oxazolidinyl, piperazinyl, dioxanyl, dioxolanyl, diazepinyl, oxazepinyl, thiazepinyl, morpholinyl, and thiamorpholinyl. A heterocyclyl group may be mono-, bi-, tri-, or polycyclic, preferably mono-, bi-, or tricyclic, more preferably mono- or bicyclic. The term "heterocyclylalkyl" refers to an alkyl group substituted by a heterocyclyl, wherein the alkyl and heterocyclyl portions independently are optionally substituted. Additionally, a heterocyclic ring also includes groups in which the heterocyclic ring is fused to one or more aryl rings.

As used herein, the term "partially unsaturated" refers to a ring moiety that includes at least one double or triple bond between ring atoms. The term "partially unsaturated" is intended to encompass rings having multiple sites of unsaturation, but is not intended to include aromatic (e.g., aryl or heteroaryl) moieties, as herein defined.

The term "alkylene" refers to a bivalent alkyl group. An "alkylene chain" is a polymethylene group, i.e., —(CH$_2$)$_n$—, wherein n is a positive integer, preferably from 1 to 6, from 1 to 4, from 1 to 3, from 1 to 2, or from 2 to 3. An optionally substituted alkylene chain is a polymethylene group in which one or more methylene hydrogen atoms is optionally replaced with a substituent. Suitable substituents include those described below for a substituted aliphatic group and also include those described in the specification herein. It will be appreciated that two substituents of the alkylene group may be taken together to form a ring system. In certain embodiments, two substituents can be taken together to form a 3-7-membered ring. The substituents can on the same or different atoms.

An alkylene chain also can be optionally interrupted by a functional group. An alkylene chain is "interrupted" by a functional group when an internal methylene unit is interrupted by the functional group. Examples of suitable "interrupting functional groups" are described in the specification and claims herein.

For purposes of clarity, all bivalent groups described herein, including, e.g., the alkylene chain linkers described above, are intended to be read from left to right, with a corresponding left-to-right reading of the formula or structure in which the variable appears.

An aryl (including aralkyl, aralkoxy, aryloxyalkyl and the like) or heteroaryl (including heteroaralkyl and heteroarylalkoxy and the like) group may contain one or more substituents and thus may be "optionally substituted". In addition to the substituents defined above and herein, suitable substituents on the unsaturated carbon atom of an aryl or heteroaryl group also include and are generally selected from -halo, —NO$_2$, —CN, —R$^+$, —C(R$^+$)=C(R$^+$)$_2$, —OR$^+$, —SR$^o$, —S(O)R$^o$, —SO$_2$R$^o$, —SO$_3$R$^+$, —SO$_2$N(R$^+$)$_2$, —N(R$^+$)$_2$, —NR$^+$C(O)R$^+$, —NR$^+$C(S)R$^+$, —NR$^+$C(O)N(R$^+$)$_2$, —NR$^+$C(S)N(R$^+$)$_2$, —N(R$^+$)C(=NR$^+$)—N(R$^+$)$_2$, —N(R$^+$)C(=NR$^+$)—R$^o$, —NR$^+$CO$_2$R$^+$, —NR$^+$SO$_2$R$^o$, —NR$^+$SO$_2$N(R$^+$)$_2$, —O—C(O)R$^+$, —O—CO$_2$R$^+$, —OC(O)N(R$^+$)$_2$, —C(O)R$^+$, —C(S)R$^o$, —CO$_2$R$^+$, —C(O)—C(O)R$^+$, —C(O)N(R$^+$)$_2$, —C(S)N(R$^+$)$_2$, —C(O)N(R$^+$)—OR$^+$, —C(O)N(R$^+$)C(=NR$^+$)—N(R$^+$)$_2$, —N(R$^+$)C(=NR$^+$)—N(R$^+$)—C(O)R$^+$, —C(=NR$^+$)—N(R$^+$)$_2$, —C(=NR$^+$)—OR$^+$, —N(R$^+$)—N(R$^+$)$_2$, —C(=NR$^+$)—N(R$^+$)—OR$^+$), —C(R$^o$)=N—OR$^+$, —P(O)(R$^+$)$_2$, —P(O)(OR$^+$)$_2$, —O—P(O)—OR$^+$, and —P(O)(NR$^+$)—N(R$^+$)$_2$, wherein R$^+$, independently, is hydrogen or an optionally substituted aliphatic, aryl, heteroaryl, cycloaliphatic, or heterocyclyl group, or two independent occurrences of R$^+$ are taken together with their intervening atom(s) to form an optionally substituted 5-7-membered aryl, heteroaryl, cycloaliphatic, or heterocyclyl ring. Each R$^o$ is an optionally substituted aliphatic, aryl, heteroaryl, cycloaliphatic, or heterocyclyl group.

An aliphatic or heteroaliphatic group, or a non-aromatic carbycyclic or heterocyclic ring may contain one or more substituents and thus may be "optionally substituted". Unless otherwise defined above and herein, suitable substituents on the saturated carbon of an aliphatic or heteroaliphatic group, or of a non-aromatic carbocyclic or heterocyclic ring are selected from those listed above for the unsaturated carbon of an aryl or heteroaryl group and additionally include the following: =O, =S, =C(R*)$_2$, =N—N(R*)$_2$, =N—OR*, =N—NHC(O)R*, =N—NHCO$_2$R$^o$=N—NHSO$_2$R$^o$ or =N—R* where R$^o$ is defined above, and each R* is independently selected from hydrogen or an optionally substituted C$_{1-6}$ aliphatic group.

In addition to the substituents defined above and herein, optional substituents on the nitrogen of a non-aromatic heterocyclic ring also include and are generally selected from —R$^+$, —N(R$^+$)$_2$, —C(O)R$^+$, —C(O)OR$^+$, —C(O)C(O)R$^+$, —C(O)CH$_2$C(O)R$^+$, —S(O)$_2$R$^+$, —S(O)$_2$N(R$^+$)$_2$, —C(S)N(R$^+$)$_2$, —C(=NH)—N(R$^+$)$_2$, or —N(R$^+$)S(O)$_2$R$^+$; wherein each R$^+$ is defined above. A ring nitrogen atom of a heteroaryl or non-aromatic heterocyclic ring also may be oxidized to form the corresponding N-hydroxy or N-oxide compound. A nonlimiting example of such a heteroaryl having an oxidized ring nitrogen atom is N-oxidopyridyl.

As detailed above, in some embodiments, two independent occurrences of R$^+$ (or any other variable similarly defined in the specification and claims herein), are taken together with their intervening atom(s) to form a monocyclic or bicyclic ring selected from 3-13-membered cycloaliphatic, 3-12-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur.

Exemplary rings that are formed when two independent occurrences of R$^+$ (or any other variable similarly defined in the specification and claims herein), are taken together with their intervening atom(s) include, but are not limited to the following: a) two independent occurrences of R$^+$ (or any other variable similarly defined in the specification or claims herein) that are bound to the same atom and are taken together with that atom to form a ring, for example, N(R$^+$)$_2$, where both occurrences of R$^+$ are taken together with the nitrogen atom to form a piperidin-1-yl, piperazin-1-yl, or morpholin-4-yl group; and b) two independent occurrences of R$^+$ (or any other variable similarly defined in the specification or claims herein) that are bound to different atoms and are taken together with both of those atoms to form a ring, for example where a phenyl group is substituted with two occurrences of OR⁺

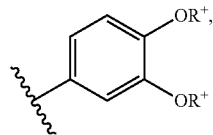

these two occurrences of R⁺ are taken together with the oxygen atoms to which they are bound to form a fused 6-membered oxygen containing ring

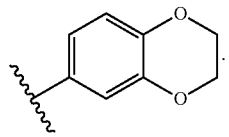 [SMILES: *c1ccc2c(c1)OCCO2]

It will be appreciated that a variety of other rings (e.g., Spiro and bridged rings) can be formed when two independent occurrences of R⁺ (or any other variable similarly defined in the specification and claims herein) are taken together with their intervening atom(s) and that the examples detailed above are not intended to be limiting.

Exemplary rings that are formed when two independent occurrences of $R^{3'}$ or $R^4$ are taken together with their intervening atom(s) include, but are not limited to the following: indolizinyl, imidazopyridyl, indolyl, isoindolyl, indazolyl, benzimidazolyl, benzthiazolyl, benzoxazolyl, 4H-furo[3,2-b]pyrrolyl, pyrazolopyrimidinyl, purinyl, and pyrrolizinyl.

Exemplary rings that are formed when two independent occurrences of $R^7$, $R^{7a}$, or $R^{7b}$ are taken together with their intervening atom(s) include, but are not limited to the following: cyclopropyl, cyclobutyl, cyclopentyl, cyclohexyl, cycloheptyl, cyclooctyl, cyclopentenyl, cyclohexenyl, cycloheptenyl, cyclooctenyl, tetrahydrofuranyl, tetrahydropyranyl, tetrahydrothienyl, pyrrolidinyl, pyrrolidonyl, piperidinyl, pyrrolinyl, oxazolidinyl, piperazinyl, dioxanyl, furanyl, thienyl, pyrrolyl, oxazolyl, thiazolyl, imidazolyl, pyranyl, pyridyl, pyrimidinyl, pyrazinyl, triazinyl, morpholinyl, and thiomorpholinyl.

Exemplary rings that are formed when two independent occurrences of $R^{7a}$ and $R^2$, or $R^{7b}$ and $R^2$ are taken together with their intervening atom(s) include, but are not limited to the following: isoindolyl, indazolyl, benzothienyl, dihydrobenzothienyl, isobenzofuranyl, benzoisoxazolyl, dihydroisobenzofuranyl, pyrazolopyrimidinyl, pyrazolopyridinyl, isoquinolyl, tetrahydroisoquinolinyl, phthalazinyl, isochromanyl, isothiochromanyl, isoindolinyl, and benzoisothiazolyl.

Exemplary rings that are formed when two independent occurrences of $X_4$ and $X_5$, or $X_6$ and $X_7$; are taken together with their intervening atom(s) include, but are not limited to the following: pyrazolopyrimidinyl, purinyl, quinolyl, tetrahydroquinolinyl, quinazolinyl, naphthyridinyl, pyridopyrimidinyl, pyrazolopyridinyl, pyrrolopyridinyl, pyrrolopyrimidinyl, imidazopyridinyl, 1H-pyrrolo[2,3-b]pyridinyl-2(3H)-one, 3,4-dihydro-1,8-naphthyridinyl-2(1H)-one, 1,8-naphthyridinyl-2(1H)-one, 1H-pyridyl[2,3-d][1,3]oxazin-2 (4H)-one, 1H-imidazo[4,5-b]pyridyl-2(3H)-one, oxazolo[4,5-b]pyridyl-2(3H)-one, 1,2-dihydropyridyl[2,3-b]pyrazin-3 (4H)-one, 2H-pyridyl[3,2-b][1,4]oxazin-3 (4H)-one, 3,4-dihydropyridyl[2,3-d]pyrimidin-2(1H)-one, imidazopyridinyl, and tetrahydroquinazolinyl.

Exemplary rings that are formed when two independent occurrences of $Y_1$ and $Q_1$, $Y_3$ and $Q_2$, or $Y_4$ and $Y_5$ are taken together with their intervening atom(s) include, but are not limited to the following: indolyl, indazolyl, 4H-furo[3,2-b]pyrrolyl, 4H-thieno[3,2-b]pyrrolyl, 5H-furo[2,3-b]pyrrolyl, 5H-thieno[2,3-b]pyrrolyl, pyrrolo[3,4-b]pyrrolyl, pyrrolo[3,2-b]pyrrolyl, pyrrolo[2,3-b]pyrrolyl, dihydropyrrolo[3,2-b]pyrrolyl, dihydropyrrolo[2,3-b]pyrrolyl, 5H-pyrrolo[3,2-d]oxazole, 5H-pyrrolo[3,2-d]thiazole, pyrrolopyrimidinyl, pyrrolopyridinyl, pyrazolopyrimidinyl and pyrazolopyridinyl.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures where there is a replacement of hydrogen by deuterium or tritium, or a replacement of a carbon by a $^{13}$C— or $^{14}$C-enriched carbon are within the scope of this invention. Such compounds are useful, as a nonlimiting example, as analytical tools or probes in biological assays.

It is to be understood that, when a disclosed compound has at least one chiral center, the present invention encompasses one enantiomer of inhibitor free from the corresponding optical isomer, racemic mixture of the inhibitor and mixtures enriched in one enantiomer relative to its corresponding optical isomer. When a mixture is enriched in one enantiomer relative to its optical isomers, the mixture contains, for example, an enantiomeric excess of at least 50%, 75%, 90%, 95% 99% or 99.5%.

The enantiomers of the present invention may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. Where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a disclosed compound has at least two chiral centers, the present invention encompasses a diastereomer free of other diastereomers, a pair of diastereomers free from other diastereomeric pairs, mixtures of diastereomers, mixtures of diasteromeric pairs, mixtures of diasteromers in which one diastereomer is enriched relative to the other diastereomer(s) and mixtures of diasteromeric pairs in which one diastereomeric pair is enriched relative to the other diastereomeric pair(s). When a mixture is enriched in one diastereomer or diastereomeric pair(s) relative to the other diastereomers or diastereomeric pair(s), the mixture is enriched with the depicted or referenced diastereomer or diastereomeric pair(s) relative to other diastereomers or diastereomeric pair(s) for the compound, for example, by a molar excess of at least 50%, 75%, 90%, 95%, 99% or 99.5%.

The diastereoisomeric pairs may be separated by methods known to those skilled in the art, for example chromatography or crystallization and the individual enantiomers within each pair may be separated as described above. Specific procedures for chromatographically separating diastereomeric pairs of precursors used in the preparation of compounds disclosed herein are provided the examples herein.

3. Description of Exemplary Compounds:

In certain embodiments, for compounds of general formula IA or IB, CY is:

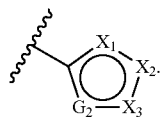

In certain embodiments, for compounds of general formula IA or IB, $X_1$ is N, $G_2$ is —N(R$^{3'}$)—, and $X_2$ and $X_3$ are CH. In certain other embodiments, $X_1$ and $X_2$ are N, $G_2$ is —N(R$^{3'}$)—, and $X_3$ is CH. In certain other embodiments, $X_3$ is N, $G_2$ is —N(R$^{3'}$)—, and $X_1$ and $X_2$ are CH. In certain other embodiments, $X_1$ is N, $X_2$ is CH, $X_3$ is N(R$^{3'}$)— and $G_2$ is =N—.

In certain embodiments, for compounds of general formula IA or IB, HY is selected from:

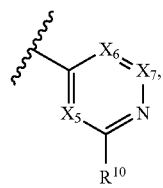

H

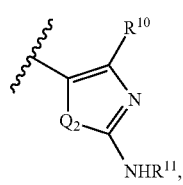

J

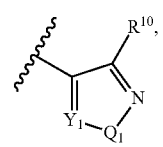

K

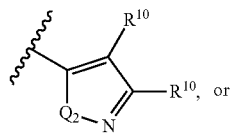

L

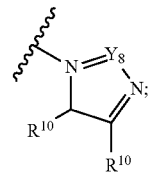

M wherein each occurrence of $X_5$, $X_6$, and $X_7$ is independently —CR$^{10}$ or N, provided no more than two occurrences of $X_5$, $X_6$, and $X_7$ are N;

each occurrence of $Q_1$ and $Q_2$ is independently S, O or NR$^5$;

each occurrence of $Y_1$ and $Y_7$ is independently —CR$^{10}$ or N;

or wherein two adjacent occurrences of $X_6$ and $X_7$, or $Y_1$ and $Q_1$, taken together with the atom to which they are bound, form an optionally substituted fused group selected from 5-6-membered aryl, or 5-6-membered heteroaryl having 1-5 heteroatoms independently selected from nitrogen, oxygen, or sulfur.

In certain embodiments, for compounds of general formula IA or IB, HY is selected from:

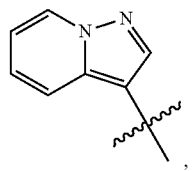

i

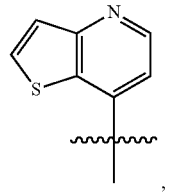

ii

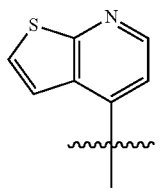

iii

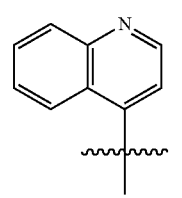

iv

31
-continued
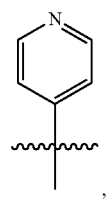 v,
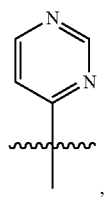 vi,
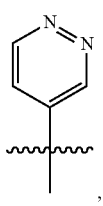 vii,
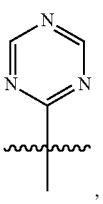 viii,
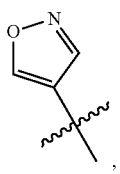 ix,
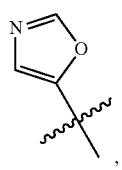 x,
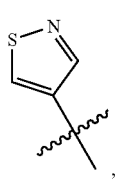 xi,
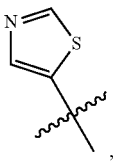 xii,
32
-continued
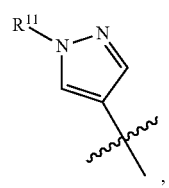 xiii,
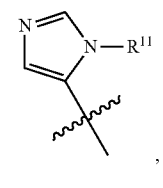 xiv,
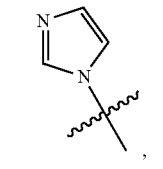 xv,
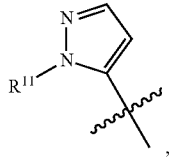 xvi,
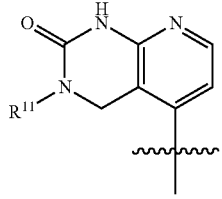 xvii,
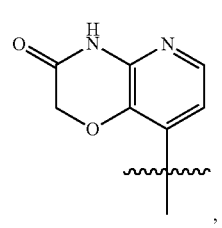 xviii,
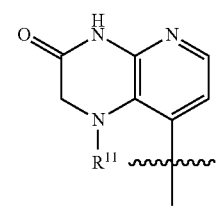 xix,
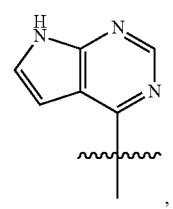 xx, -continued
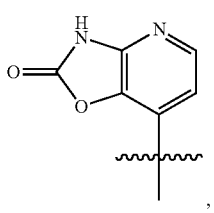, xxi
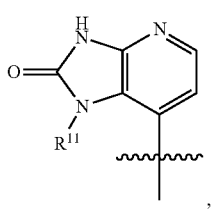, xxii
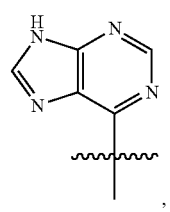, xxiii
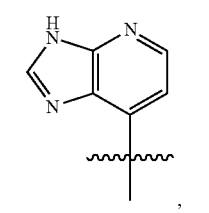, xxiv
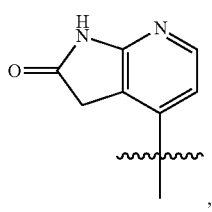, xxv
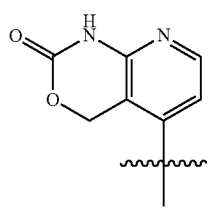, xxvi
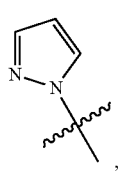,
-continued
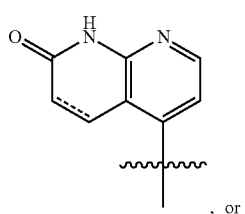, or  xxviii
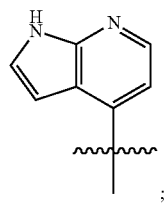;  xxix
wherein each HY group is optionally additionally substituted with one or more occurrences of $R^{10}$, and ----- in xviii represents a single bond or a double bond.
In certain embodiments, for compounds of general formula IA or IB, HY is selected from:
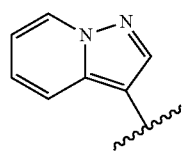, i
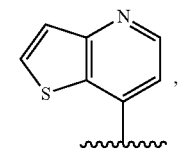, ii
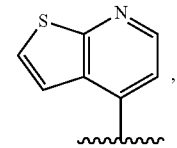, iii
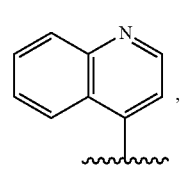, iv
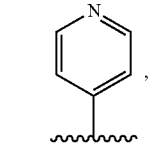, v
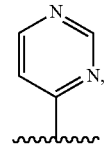, vi -continued

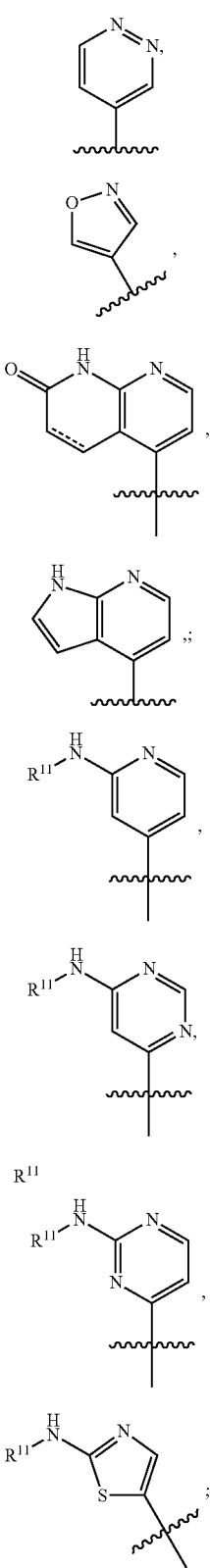

wherein each HY group is optionally additionally substituted with one or more occurrences of $R^{10}$, and ------ in xviii represents a single bond or a double bond.

In yet other embodiments, for compounds of general formula IA or IB, $G_1$ is $C(R^8)$. In other embodiments, $G_1$ is CH.

In still other embodiments, $G_1$ is N.

In certain embodiments, for compounds of general formula IA or IB, W is $—C(R^7)_2—$, wherein one occurrence of $R^7$ is hydrogen and the other occurrence of $R^7$ is hydrogen, optionally substituted $C_{1-6}$ aliphatic, $—N(R^{7b})_2$, $—OR^{7a}$, $—SR^{7a}$, halo, or —CN; and wherein each occurrence of $R^{7a}$ is independently hydrogen or optionally substituted $C_{1-6}$ aliphatic; and each occurrence of $R^{7b}$ is independently hydrogen, optionally substituted $C_{1-6}$ aliphatic, $—C(O)R^{7a}$, or $—S(O)_2R^{7a}$; or wherein two occurrences of $R^{7b}$, taken together with the nitrogen atom to which they are bound, form an optionally substituted 3-6-membered heterocyclic ring.

In certain embodiments, for compounds of general formula IA or IB, W is $—C(H)(N(R^{7b})_2)—$, $—CH_2—$, $—C(H)(OR^{7a})—$, $—NR^{7b}—$, or $—N(R^{7a})C(O)—$, wherein each occurrence of $R^{7a}$ is independently hydrogen or optionally substituted $C_{1-6}$ aliphatic; and each occurrence of $R^{7b}$ is independently hydrogen or optionally substituted $C_{1-6}$ aliphatic.

In certain embodiments, for compounds of general formula IA or IB, Ring A is 6-10-membered aryl or 5-10-membered heteroaryl having 1-5 heteroatoms independently selected from nitrogen, oxygen, or sulfur; and n is 0 to 3.

In certain embodiments, for compounds of general formula IA or IB, Ring A is a phenyl group; each occurrence of $R^2$ is independently halogen, $C_{1-3}$ alkyl, —CN, $C_{1-3}$haloalkyl, $—OC_{1-3}$ alkyl, $—OC_{1-3}$ haloalkyl, $—NHC(O)C_{1-3}$ alkyl, $—NHC(O)NHC_{1-3}$ alkyl, $—NHS(O)_2C_{1-3}$ alkyl, or $—C(O)H$; and n is 0 to 3.

In still other embodiments, Ring A is a phenyl group, $R^2$ is halogen and n is 1 to 2.

In still other embodiments, a compound having the structure of formula II is provided:

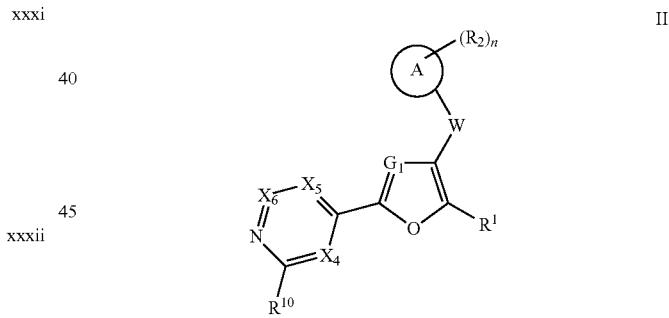

II wherein:

$X_4$, $X_5$ and $X_6$ are each independently $—CR^{10}$ or N, provided no more than two occurrences of $X_4$, $X_5$ and $X_6$ are N; or two adjacent groups selected from $R^{10}$, $X_4$, $X_5$, and $X_6$, taken together, form an optionally substituted group selected from 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur.

In some embodiments, for compounds of formula II, one of $X^4$, $X^5$, or $X^6$ is N.

In still other embodiments, for compounds of formula II, all of $X^4$, $X^5$, or $X^6$ are $CR^{10}$.

In other embodiments, for compounds of formula II, each occurrence of $R^{10}$ is independently selected from —CN, $—OR^{10a}$, $—N(R^{11})_2$, halogen, $C_{1-4}$alkyl, $—N(R^{11})COR^{10a}$, or wherein two occurrences of $R^{10}$, taken together with the atoms to which they are bound form an optionally substituted group selected from a fused 5- or 6-membered cycloaliphatic, 4-10-membered heterocyclyl, 6-10-membered aryl or 5-10-membered heteroaryl ring, wherein the heterocyclyl and heteroaryl rings have 1-3 heteroatoms independently selected from nitrogen, oxygen, or sulfur.

In some other embodiments, for compounds of formula II, CY is

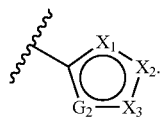

In some other embodiments, for compounds of formula II, $X_1$ is N, $G_2$ is —N($R^{3'}$)—, and $X_2$ and $X_3$ are CH.

In some other embodiments, for compounds of formula II, $X_1$ and $X_2$ are N, $G_2$ is —N($R^{3'}$)—, and $X_3$ is CH.

In some other embodiments, for compounds of formula II, $X_3$ is N, $G_2$ is —N($R^{3'}$)—, and $X_1$ and $X_2$ are CH.

In some other embodiments, for compounds of formula II, $X_1$ is N, $X_2$ is CH, $X_3$ is N($R^{3'}$)— and $G_2$ is =N—.

In some other embodiments, for compounds of formula II, Ring A is an optionally substituted 6-10-membered aryl or 5-10-membered heteroaryl having 1-5 heteroatoms independently selected from nitrogen, oxygen, or sulfur; and n is 0 to 3.

In some other embodiments, for compounds of formula II, Ring A is a phenyl group optionally substituted with 1-3 independent occurrences of halogen, $C_{1-3}$ alkyl, —CN, $C_{1-3}$haloalkyl, —O$C_{1-3}$ alkyl, O$C_{1-3}$ haloalkyl, —NHC(O)$C_{1-3}$ alkyl, —NHC(O)NH$C_{1-3}$ alkyl, NHS(O)$_2C_{1-3}$ alkyl, or —C(O)H; and n is 0 to 3.

In still other embodiments, Ring A is a phenyl group, $R^2$ is halogen and n is 1 to 2.

In some other embodiments, for compounds of formula II, W is —C($R^7$)$_2$—, wherein one occurrence of $R^7$ is hydrogen and the other occurrence of $R^7$ is selected from hydrogen, optionally substituted $C_{1-4}$ aliphatic, —N($R^{7b}$)$_2$, —O$R^{7a}$, —S$R^{7a}$, halo, or —CN; and
wherein each occurrence of $R^{7a}$ is independently hydrogen or optionally substituted $C_{1-6}$ aliphatic;
each occurrence of $R^{7b}$ is independently hydrogen, optionally substituted $C_{1-6}$ aliphatic, —C(O)$R^{7a}$, or —S(O)$_2$$R^{7a}$; or
wherein any two occurrences of $R^7$, $R^{7a}$, or $R^{7b}$ taken together with the atom to which they are bound, form an optionally substituted group selected from a 3-6-membered cycloaliphatic ring, 6-10-membered aryl, 3-6-membered heterocyclyl having 1-5 heteroatoms independently selected from nitrogen, oxygen, or sulfur, or 5-10-membered heteroaryl having 1-5 heteroatoms independently selected from nitrogen, oxygen, or sulfur; or any two occurrences of $R^{7a}$ and $R^2$, or $R^{7b}$ and $R^2$ taken together with the nitrogen atom to which they are bound, form an optionally substituted group selected from 3-6-membered heterocyclyl having 1-5 heteroatoms independently selected from nitrogen, oxygen, or sulfur, or 5-10-membered heteroaryl having 1-5 heteroatoms independently selected from nitrogen, oxygen, or sulfur.

In some other embodiments, for compounds of formula II, W is —C(H)(N($R^{7b}$)$_2$)—, —C(H)(O$R^{7a}$)—, —N$R^{7b}$—, or —N($R^{7a}$)C(O)—, wherein each occurrence of $R^{7a}$ is independently hydrogen or optionally substituted $C_{1-6}$ aliphatic; and each occurrence of $R^{7b}$ is independently hydrogen or optionally substituted $C_{1-6}$ aliphatic.

In still other embodiments, a compound having the structure of formula III is provided:

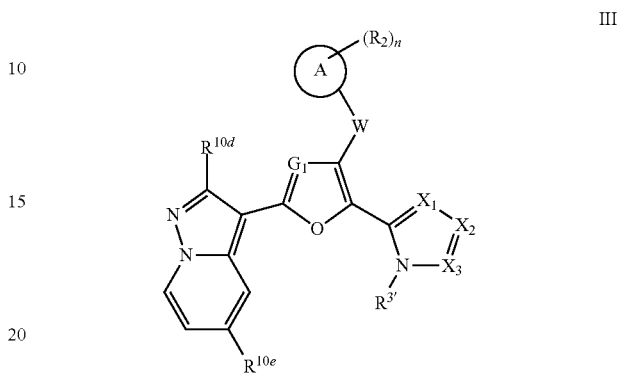

wherein $R^{10d}$ is hydrogen or optionally substituted $C_{1-4}$alkyl, and $R^{10e}$ is $R^{10}$.

In some other embodiments, for compounds of formula III, $R^{10e}$ is $T_1$-$R^{10b}$, or hydrogen.

In still other embodiments, for compounds of formula III, $R^{10e}$ is hydrogen, —CH$_2$N($R^{11}$)$_2$, or —CH$_2$N($R^{11}$)C(=N$R^{11}$)N($R^{11}$)$_2$, wherein $R^{11}$ is —C(O)$R^{11a}$, an optionally substituted group selected from $C_{1-6}$ aliphatic, 3-10-membered cycloaliphatic, 4-10-membered heterocyclyl having 1-5 heteroatoms independently selected from nitrogen, oxygen or sulfur, 6-10-membered aryl, or 5-10-membered heteroaryl having 1-5 heteroatoms independently selected from nitrogen, oxygen, or sulfur.

In some other embodiments, for compounds of formula III, $R^{11}$ is an optionally substituted $C_{1-6}$ aliphatic group, the $C_{1-6}$ aliphatic group is further defined as —(CH$_2$)$_x$$R^{11b}$ or —(CH$_2$)$_x$N($R^{11b}$)$_2$, —(CH$_2$)$_x$N($R^{11b}$)C(O)$R^{11b}$, or (CH$_2$)$_x$N($R^{11b}$)C(O)O$R^{11b}$, wherein $R^{11b}$ is hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur; and x is 1 to 3.

In some other embodiments, for compounds of formula III, $X_1$ is N, and $X_2$ and $X_3$ are CH.

In some other embodiments, for compounds of formula III, $X_1$ and $X_2$ are N, and $X_3$ is CH.

In some other embodiments, for compounds of formula III, $X_3$ is N, and $X_1$ and $X_2$ are CH.

In some other embodiments, for compounds of formula III, Ring A is an optionally substituted 6-10-membered aryl or 5-10-membered heteroaryl having 1-5 heteroatoms independently selected from nitrogen, oxygen, or sulfur; and n is 0 to 3.

In some other embodiments, for compounds of formula III, Ring A is a phenyl group optionally substituted with 1-3 independent occurrences of halogen, $C_{1-3}$ alkyl, —CN, $C_{1-3}$haloalkyl, —O$C_{1-3}$ alkyl, —O$C_{1-3}$haloalkyl, —NHC(O)$C_{1-3}$ alkyl, —NHC(O)NH$C_{1-3}$ alkyl, —NHS(O)$_2C_{1-3}$ alkyl, or —C(O)H; and n is 0 to 3.

In some other embodiments, Ring A is a phenyl group, $R^2$ is halogen and n is 1 to 2.

In some other embodiments, for compounds of formula III, W is —C(R$^7$)$_2$—, wherein one occurrence of R$^7$ is hydrogen and the other occurrence of R$^7$ is selected from hydrogen, optionally substituted C$_{1-4}$ aliphatic, —N(R$^{7b}$)$_2$, —OR$^{7a}$, —SR$^{7a}$, halo, or —CN; and wherein each occurrence of R$^{7a}$ is independently hydrogen or optionally substituted C$_{1-6}$ aliphatic;

each occurrence of R$^{7b}$ is independently hydrogen, optionally substituted C$_{1-6}$ aliphatic, —C(O)R$^{7a}$, or —S(O)$_2$R$^{7a}$; or wherein any two occurrences of R$^7$, R$^{7a}$, or R$^{7b}$ taken together with the atom to which they are bound, form an optionally substituted group selected from a 3-6-membered cycloaliphatic ring, 6-10-membered aryl, 3-6-membered heterocyclyl having 1-5 heteroatoms independently selected from nitrogen, oxygen, or sulfur, or 5-10-membered heteroaryl having 1-5 heteroatoms independently selected from nitrogen, oxygen, or sulfur; or any two occurrences of R$^{7a}$ and R$^2$, or R$^{7b}$ and R$^2$ taken together with the nitrogen atom to which they are bound, form an optionally substituted group selected from 3-6-membered heterocyclyl having 1-5 heteroatoms independently selected from nitrogen, oxygen, or sulfur, or 5-10-membered heteroaryl having 1-5 heteroatoms independently selected from nitrogen, oxygen, or sulfur.

In some other embodiments, for compounds of formula III, W is —C(H)(N(R$^{7b}$)$_2$)—, —CH$_2$—, —C(H)(OR$^{7a}$)—, —NR$^{7b}$—, or —N(R$^{7a}$)C(O)—, wherein each occurrence of lea is independently hydrogen or optionally substituted C$_{1-6}$ aliphatic; and each occurrence of R$^{7b}$ is independently hydrogen or optionally substituted C$_{1-6}$ aliphatic.

In certain embodiments, for compounds of general formula IA or IB, CY is:

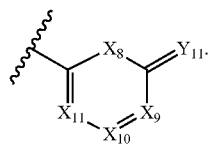

In certain embodiments, for compounds of general formula IA or IB, X$_8$ and X$_{11}$ are N, X$_9$ and X$_{10}$ are CR$^4$, and Y$_{11}$ is O.

In certain embodiments, for compounds of general formula IA or IB, HY is selected from:

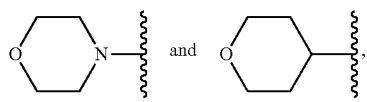

wherein each HY group is optionally additionally substituted with one or more occurrences of R$^{14}$.

In yet other embodiments, for compounds of general formula IA or IB, G$_1$ is N.

In still other embodiments, for compounds of general formula IA or IB, R$^1$ is —C(O)OH.

4. Uses, Formulation and Administration

As discussed above, the present invention provides compounds that are useful as inhibitors of PI3K enzymes, and thus the present compounds are useful for treating proliferative, inflammatory, or cardiovascular disorders such as tumor and/or cancerous cell growth mediated by PI3K. In particular, the compounds are useful in the treatment of cancers in a subject, including, but not limited to, lung and bronchus, prostate, breast, pancreas, colon and recum, thyroid, liver and intrahepatic bile duct, hepatocellular, gastric, glioma/glioblastoma, endometrial, melanoma, kidney, and renal pelvis, urinary bladder, utering corpus, uterine cervix, ovary, multiple myeloma, esophagus, acute myelogenous leukemia, chronic myelogenous leukemia, lymphocytic leukemia, myeloid leukemia, brain, oral cavity, and pharynx, small intestine, non-Hodgkin lymphoma, and villous colon adenoma.

In some embodiments, compounds of the invention are suitable for the treatment of breast cancer, bladder cancer, colon cancer, glioma, glioblastoma, lung cancer, hepatocellular cancer, gastric cancer, melanoma, thyroid cancer, endometrial cancer, renal cancer, cervical cancer, pancreatic cancer, esophageal cancer, prostate cancer, brain cancer, or ovarian cancer.

In other embodiments, compounds of the invention are suitable for the treatment of inflammatory and cardiovascular disorders including, but not limited to, allergies/anaphylaxis, acute and chronic inflammation, rheumatoid arthritis; autoimmunity disorders, thrombosis, hypertension, cardiac hypertrophy, and heart failure.

Accordingly, in another aspect of the present invention, pharmaceutical compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable prodrugs, salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of PI3K.

Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+$ $(C_{1-4}alkyl)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

In yet another aspect, a method for treating a proliferative, inflammatory, or cardiovascular disorder is provided comprising administering an effective amount of a compound, or a pharmaceutical composition to a subject in need thereof. In certain embodiments of the present invention an "effective amount" of the compound or pharmaceutical composition is that amount effective for treating a proliferative, inflammatory, or cardiovascular disorder, or is that amount effective for treating cancer. In other embodiments, an "effective amount" of a compound is an amount which inhibits binding of PI3K and thereby blocks the resulting signaling cascades that lead to the abnormal activity of growth factors, receptor tyrosine kinases, protein serine/threonine kinases, G protein coupled receptors and phospholipid kinases and phosphatases.

The compounds and compositions, according to the method of the present invention, may be administered using any amount and any route of administration effective for treating the disease. The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disease being treated and the severity of the disease; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar—agar, calcium carbonate, potato or tapioca starch, alginic acid, certain silicates, and sodium carbonate, e) solution retarding agents such as paraffin, absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage foams may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

While one or more of the inventive compounds may be used in an application of monotherapy to treat a disorder, disease or symptom, they also may be used in combination therapy, in which the use of an inventive compound or composition (therapeutic agent) is combined with the use of one or more other therapeutic agents for treating the same and/or other types of disorders, symptoms and diseases. Combination therapy includes administration of the therapeutic agents concurrently or sequentially. Alternatively, the therapeutic agents can be combined into one composition which is administered to the patient.

In one embodiment, the compounds of this invention are used in combination with other therapeutic agents, such as other inhibitors of PI3K. In some embodiments, a compound of the invention is administered in conjunction with a therapeutic agent selected from the group consisting of cytotoxic agents, radiotherapy, and immunotherapy. It is understood that other combinations may be undertaken while remaining within the scope of the invention.

Another aspect of the invention relates to inhibiting PI3K, activity in a biological sample or a patient, which method comprises administering to the patient, or contacting said biological sample with a compound of formula I or a composition comprising said compound. The term "biological sample", as used herein, generally includes in vivo, in vitro, and ex vivo materials, and also includes, without limitation, cell cultures or extracts thereof; biopsied material obtained from a mammal or extracts thereof; and blood, saliva, urine, feces, semen, tears, or other body fluids or extracts thereof.

Still another aspect of this invention is to provide a kit comprising separate containers in a single package, wherein the inventive pharmaceutical compounds, compositions and/ or salts thereof are used in combination with pharmaceutically acceptable carriers to treat disorders, symptoms and diseases where PI3K kinase plays a role.

EXPERIMENTAL PROCEDURES

I-A. Preparation of Certain Exemplary Compounds

Compounds (shown in Table 1 below) were prepared using the general methods and specific examples described directly below.

5. General Synthetic Methods and Intermediates:

The compounds of the present invention can be prepared by methods known to one of ordinary skill in the art and/or by reference to the schemes shown below and the synthetic examples that follow. Exemplary synthetic routes are set forth in Schemes 1-45 below, and in the Examples.

In methods defined below X represents halogen (Br, I or Cl), P is Hy itself or a substituent convertible to Hy by applying a generally known method, $W^R$ is W—$R^2$ itself, a substituent convertible to W—$R^2$ by applying a generally known method, $W^L$ is $R^2$ itself, or a part of W linker connected to $R^2$ and Q is $R^1$ itself or a substituent convertible to $R^1$ by applying a generally known method.

Examples of the solvent for the below-mentioned reactions include, but are not limited to halogenated hydrocarbons such as dichloromethane, chloroform, carbon tetrachloride, 1,2-dichloroethane and the like, aromatic hydrocarbons such as benzene, toluene, xylene and the like, alcohols such as methanol, ethanol, isopropanol, tert-butanol, phenol and the like, ethers such as diethyl ether, tetrahydrofuran, dioxane, DME and the like, acetone, acetonitrile, ethyl acetate, N,N-dimethylformamide, N,N-dimethylacetamide, 1-methyl-2-pyrrolidone, dimethyl sulfoxide, hexamethylphosphoramide, water or a mixed solvent thereof and the like.

One of ordinary skill in the art will recognise that numerous variations in reaction conditions including variations in solvent, reagents, catalysts, reaction temperatures and times are possible for each of the reactions described. Variation of order of synthetic steps and alternative synthetic routes are also possible.

In many cases, synthesis can be started from commercially available furane/oxazole analogs to prepare target compounds. In some cases, specially functionalized furane/oxazole analogs can be prepared by the procedures described in Schemes 1-11.

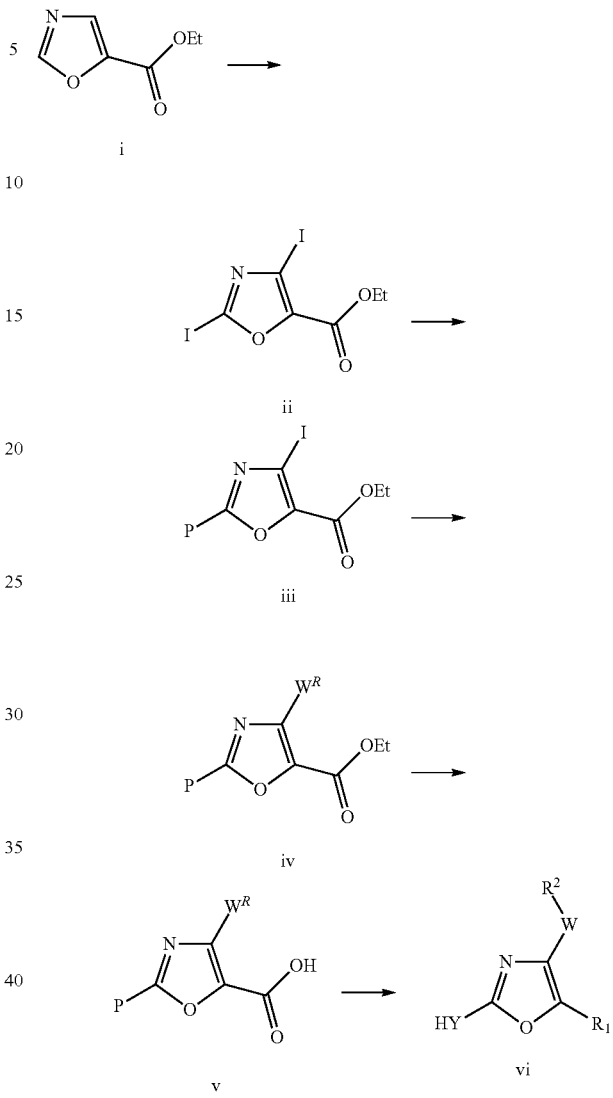

Scheme 1: General method for the synthesis of oxazoles

Scheme 1 describes a method of preparing substituted oxazoles vi. Treatment of ethyl 1,3-oxazole-5-carboxylate with lithium hexamethyldisilazane and iodine in DMPU gives ii as reported in the literature (Vedejs, E., Luchetta, L. M. J. Org. Chem. 1999, 64, 1011). Compounds iii can then be prepared from compounds ii by Method A. Method A is the coupling reaction of an aryl or heteroaryl bromide with an appropriate aryl or heteroaryl stannane under suitable conditions, for example Pd(PPh$_3$)$_4$, CuI, LiCl in an appropriate solvent, such as dioxane at elevated temperature.

Alternatively, Method A can refer to the coupling reaction of an aryl or heteroaryl bromide with an appropriate boronic acid or boronic ester under suitable conditions, for example Pd(PPh$_3$)$_4$, Cs$_2$CO$_3$, in an appropriate solvent, such as dioxane, at elevated temperature or under microwave irradiation. Transformation of compounds iii to iv can be achieved by methods described below. Compounds vi can be prepared via the intermediate acids v (obtained by hydrolysis of the ester of compounds iv under standard conditions) or by transformation of the esters iv directly to a variety of groups using standard methods.

Scheme 2: Alternate general method for the synthesis of oxazoles vi

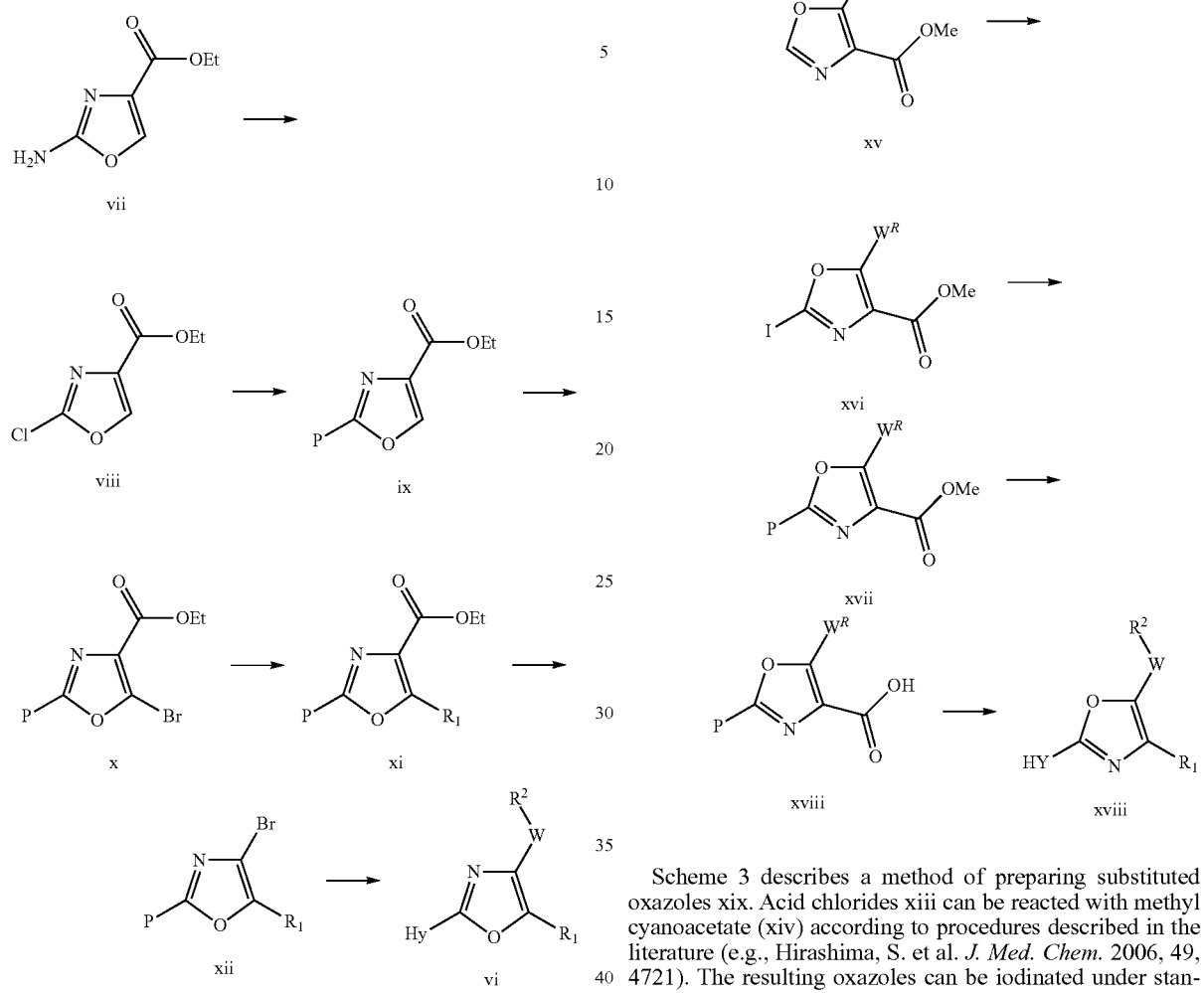

Scheme 2 describes an alternative method of preparing substituted oxazoles vi. Treatment of ethyl 2-amino-1,3-oxazole-4-carboxylate (vii) with t-butyl nitrite and copper chloride in acetonitrile gives viii as described in the literature (Hodgetts, K. J.; Kershaw, M. T. *Org. Lett.* 2002, 4, 2905). Compounds ix can be prepared by treatment of compounds viii according to Method A. Bromides x, which can be prepared from ix using standard bromination conditions, then can be convered to compounds xi using Method A. After saponification of esters xi to the corresponding carboxylic acids, bromides xii can be prepared by a standard Hunsdiecker reaction (Johnson, R. G.; Ingham, R. K. *Chem. Rev.* 1956, 56, 219). The oxazoles vi can be prepared from xii by reaction according to methods described below.

Scheme 3: General method for the synthesis of oxazoles xix

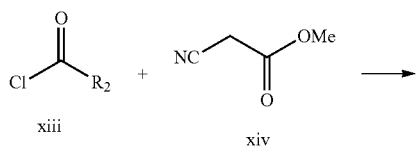

Scheme 3 describes a method of preparing substituted oxazoles xix. Acid chlorides xiii can be reacted with methyl cyanoacetate (xiv) according to procedures described in the literature (e.g., Hirashima, S. et al. *J. Med. Chem.* 2006, 49, 4721). The resulting oxazoles can be iodinated under standard conditions, for example treatment with lithium hexamethyldisilazine and iodine in a solvent such as THF to give iodides xvi. The oxazoles xvii can be prepared from xvi using Method A. Compounds xvii can be elaborated to oxazoles xix through a series of standard transformations as described for the preparation of compounds vi in Scheme 1.

Scheme 4: Alternate general method for the synthesis of oxazoles xix

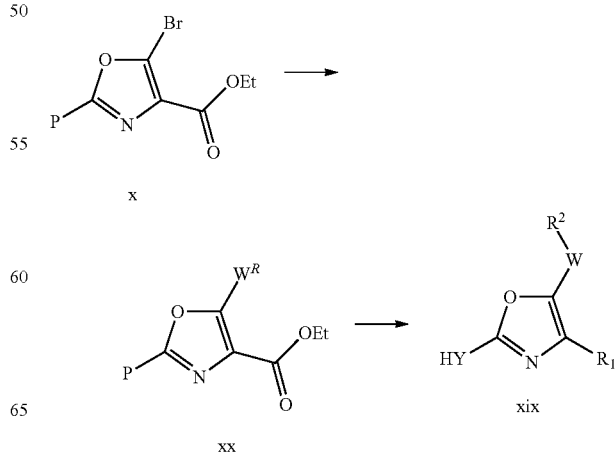

Scheme 4 describes an alternative method of preparing substituted oxazoles xix. Compounds xx can be prepared by reaction according to Method A or Method B. Compounds xx can be elaborated to oxazoles xix through a series of standard transformations as described for the preparation of compounds vi in Scheme 1.

Scheme 5: Alternate general method for the synthesis of oxazoles xix

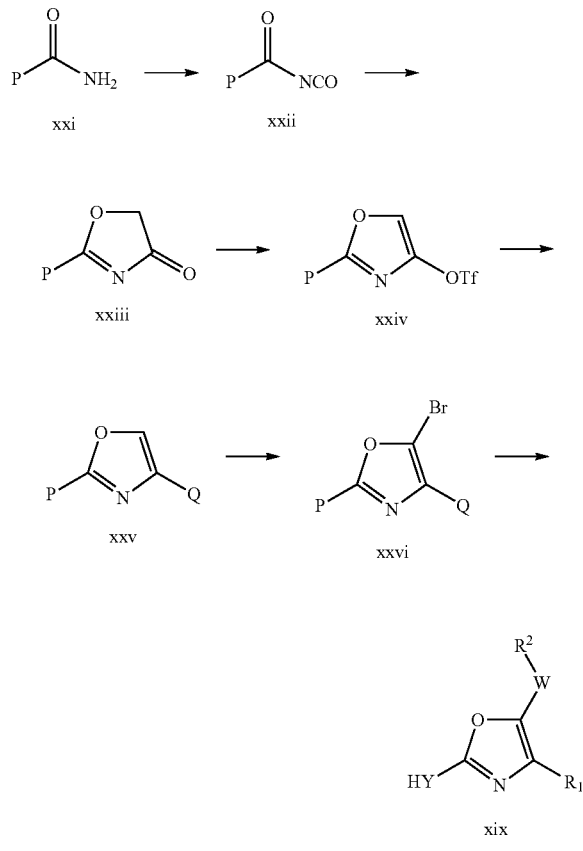

Scheme 6: General route for the synthesis of substituted cyanofuranes

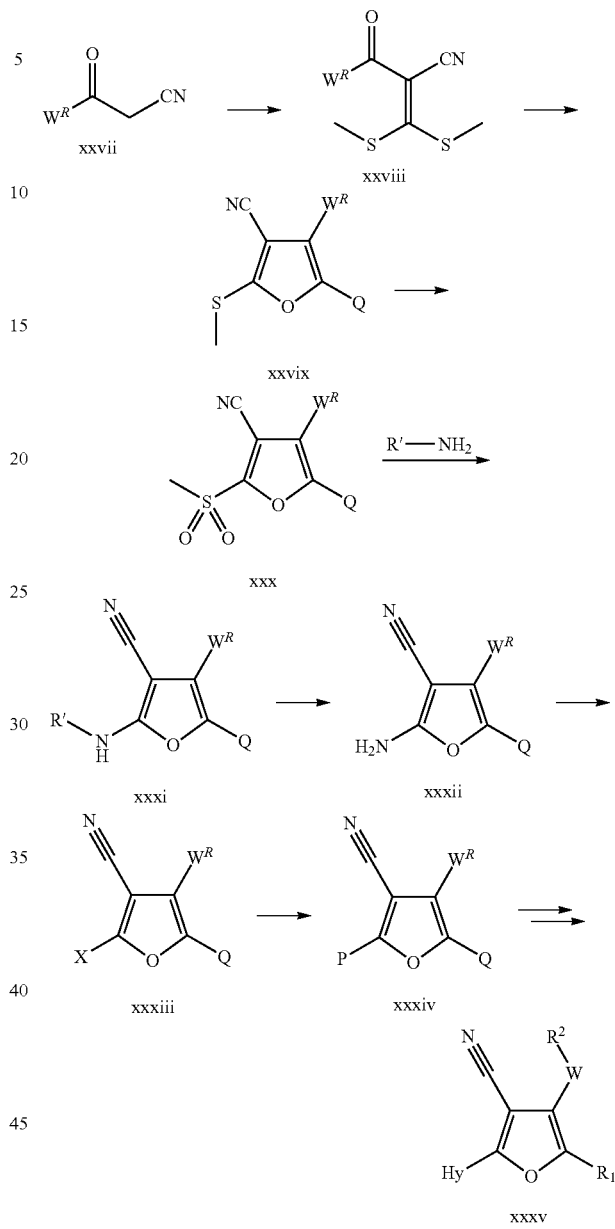

Scheme 5 describes an alternative method of preparing substituted oxazoles xix. Treatment of amides xxi with oxalyl chloride gives the acyl isocyanates xxii (McGrew, L. A. et al. *J. Org. chem.* 1964, 29, 3002). Compounds xxii can be treated with trimethylsilyldiazomethane to give compounds xxiii (Hari, Y,; Iguchi, T.; Aoyama, T. *Synthesis* 2004, 1359), which can be converted to the corresponding triflates xxiv upon treatment with triflic anhydride. Compounds xxv can be prepared by treatment of xxiv with appropriate boronic acids or esters under suitable conditions, for example PdCl2(PPh$_3$)$_2$, Na$_2$CO$_3$, in an appropriate solvent, such as dioxane, at elevated temperature or under microwave irradiation. Alternatively, compounds xxv can also be prepared by conversion of xxiv to the corresponding boronic acids or esters followed by coupling with appropriate triflates as described in the literature (Flegeau, E. F.; Popkin, M. E.; Greaney, M. F. *Org. Lett.* 2006, 8, 2495). Compounds xxv can be brominated under standard conditions to give compounds xxvi, which can then be treated according to methods described below to give compounds of formula xix.

Compounds of formula xxxv can be prepared from compounds xxvii according to procedure described in the literature (Fernandez, M.-C.; Castano, A.; Dominguez, E.; Escribano, A.; Jiang, D.; Jimenez, A.; Hong, E.; Hornback, W. J.; Nisenbaum, E. S.; Rankl, N.; Tromiczak, E.; Vaught, G.; Zarrinmayeh, H.; Zimmerman, D. M. *Bioorg. Med. Chem. Lett.*, 2006, 66, 5057-5061), as outlined in Scheme 6. Deprotonation of propionitriles xxvii followed by condensation with carbon disulfide and subsequesnt quenching with methyl iodide gives compounds of formula xxviii. These compounds can be further converted to furan ethyl carboxylates xxvix (Q=COOEt) by cyclocondensation with bromoethyl acetate. Further elaboration includes oxidation of methyl sulfide to sulfone xxx using a suitable oxidant, such as mCPBA in DCM, which can be displaced with an amine, for example dimethoxybenzylamine to afford compounds of formula xxxi. Treatment of xxxi with an acid, like TFA in DCM can give amines xxxii, that can be subjected to Sandmeyer reaction using standard conditions, for example CuBr$_2$, amyl nitrate in acetonitrile at elevated temperature to give halides xxxiii. Halides xxxiii can then be treated according to Method A to give compounds of formula xxxiv, that can be further transformed to xxxv by methods described below.

Scheme 7: General route for the synthesis of substituted furanes

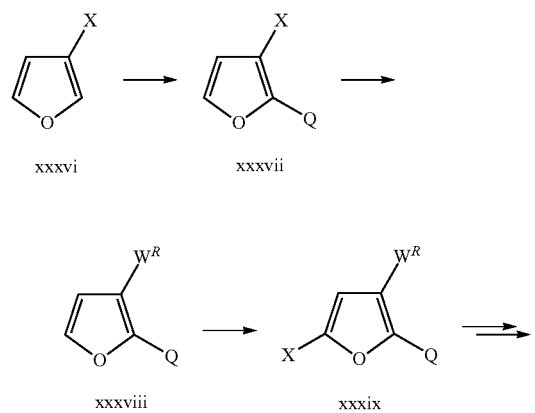

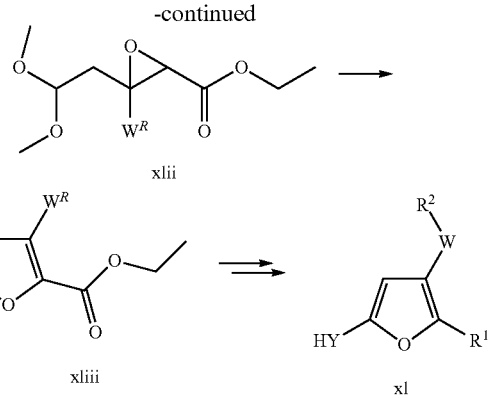

Scheme 8 above shows an alternate procedure for the preparation of substituted furanes of formula xxxviii according to procedure described in the literature (Lee et al *Bioorg. Med. Chem. Lett.* 2007, 17, 1291). Condensation of β-ketoacetals with ethylchlorocarbonate in the presence of a suitable base, such as sodium methanolate in THF provides intermediate epoxides xlii that are thermolytically treated to afford esters xliii according to Darzen cyclization. Transformation of xliii to xl can be achieved by methods described in Scheme 7 and other parts of this document.

Scheme 9: General route for the synthesis of substituted 3-aminofuranes

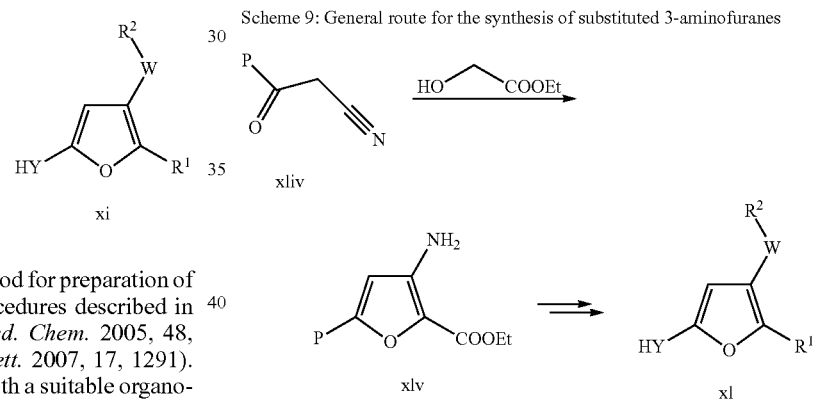

Scheme 7 above shows a general method for preparation of furanes of formula xl according to procedures described in the literature (Zhang, H.-Z et al *J. Med. Chem.* 2005, 48, 5215; Lee et al *Bioorg. Med. Chem. Lett.* 2007, 17, 1291). 3-halofuranes xxxvi are deprotonated with a suitable organometallic base, for example LDA in a suitable solvent, such as THF to generate organolithium species that are then quenched with a suitable electrofile, such as CO$_2$ to afford xxxvii (Q=COOH). Compounds xxxvii can be then transformed into compounds xxxviii using methods described below. Halogenation can be then accomplished by the treatment of xxxviii with halogen molecule, for example bromine in a suitable solvent, like diethylether to give compounds of formula xxxvix. Compounds xl can be prepared by the coupling of compounds xxxix according to Method A followed by additional transformations described below.

Compounds of formula xlv can be prepared according to the literature procedure (Lee et al *Bioorg. Med. Chem. Lett.* 2007, 17, 1291) as shown in Scheme 9. Cyanomethyl ketones xliv can be treated with ethyl glycolate under Mitsunobu conditions, such as PPh$_3$, DEAD, THF followed by treatment with a base, for example sodium hydride that leads to cyclization to 3-aminofuranes of formula xlv, that can be further elaborated to compounds xl using methods described in this document.

Scheme 10: Alternate route for the synthesis of substituted furanes

Scheme 8: Alternate route for the synthesis of substituted furanes

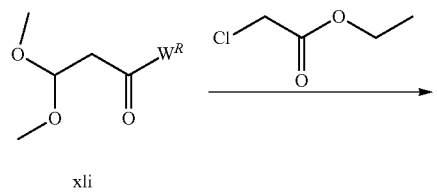

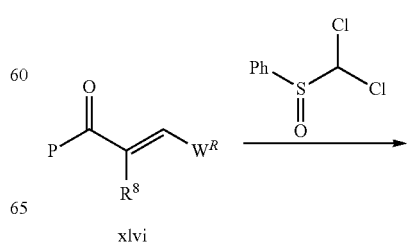

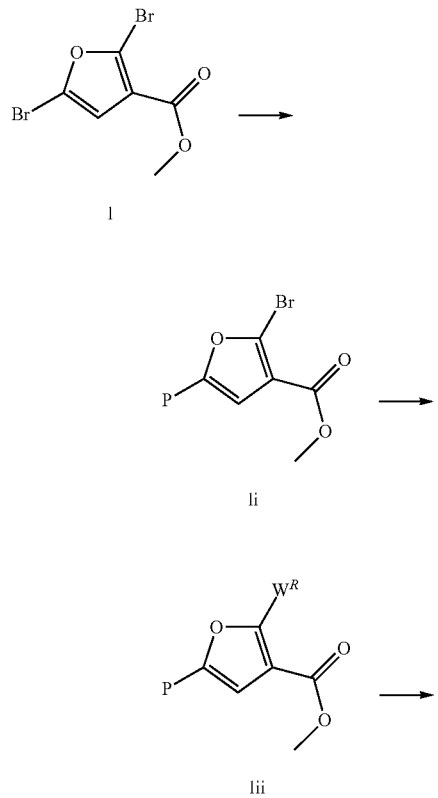

Compounds of formula iI can be prepared according to the literature procedure (Miyagawa, T.; Satoh, T. *Tetrahedron Lett.* 2007, 48, 4849) as shown in scheme 10. Alkenyl ketones xlvi can be treated with dichloromethylphenyl sulfoxide in the presence of a suitable base, like LDA, with HMPA at low temperature in a suitable solvent, for example THF to give adduct xlvii. The latter compound can be then treated with TFAA under suitable conditions, for example with NaI in acetonitrile to afford furanes of formula xlviii. Phenyl sulfide can be then oxidized to an intermediate sulfoxide, for example with mCPBA in DCM, and subsequently treated with i-PrMgCl to give 2-magnesiofuran, that can be further treated with electrofiles to afford compounds of formula iI.

Scheme 11: Alternate route for the synthesis of substituted furanes

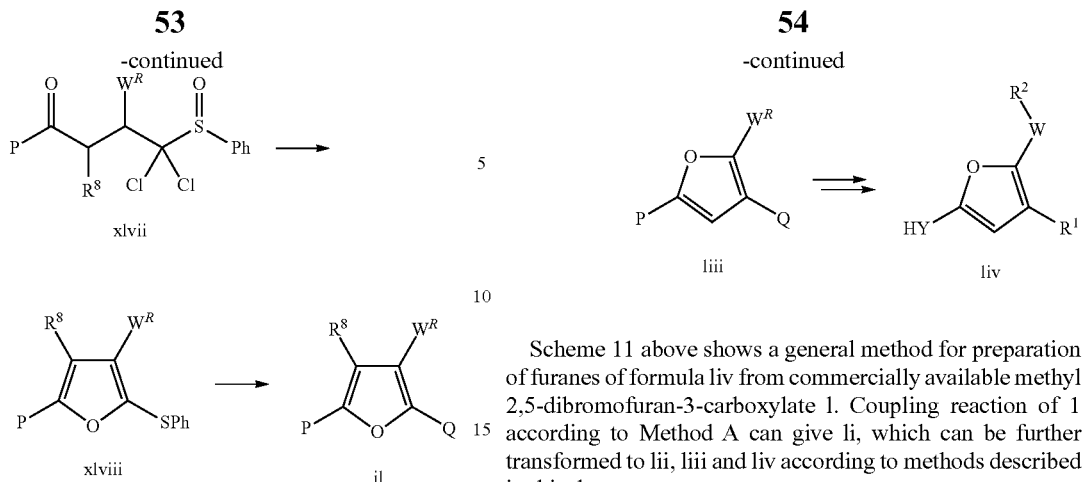

Scheme 11 above shows a general method for preparation of furanes of formula liv from commercially available methyl 2,5-dibromofuran-3-carboxylate 1. Coupling reaction of 1 according to Method A can give li, which can be further transformed to lii, liii and liv according to methods described in this document.

Schemes 12-36 describe procedures for basic functional group transformations on the thiophene/thiazole central core scaffolds.

Schemes 12-19 describe methods for the introduction of W—R$_A$ groups.

Scheme 12: General method for introducing carbon functionality to 4-halogentated furanes/oxazoles.

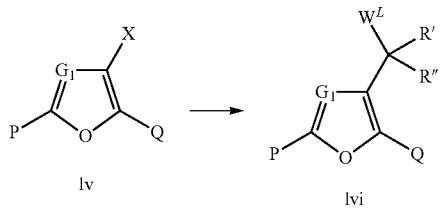

As shown in Scheme 12 above, carbon functionality can be introduced by the well known cross-coupling technique from the 4-halogenated furanes/oxazoles lv which can be prepared by the procedure described in schemes 1, 2, 4, 5, 7, 11.

For example, lvi can be obtained from lvi by reaction with an organic boronic acid reagent, or an organic zinc reagent in a presence of palladium catalyst. Suzuki couplings with alkyl, alkenyl boronic acids or esters can be performed using Pd(PPh$_3$)$_4$, or a similar palladium catalyst, a suitable base, such as sodium carbonate in an appropriate solvent, such as DME/water at elevated temperature (Method A), while Pd(tBu$_3$P)$_2$ can be used for Negishi coupling reactions, together with in a suitable solvent, such as THF at elevated temperature (Method B).

Scheme 13: General method for introducing carbon functionality to 4-halogentated furanes/oxazoles.

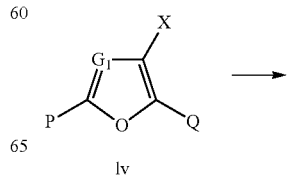

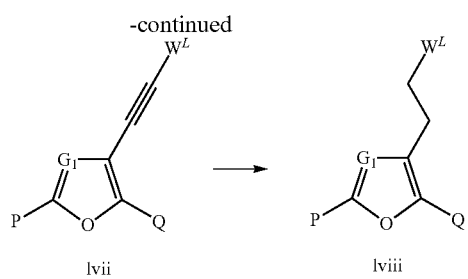

Scheme 13 above shows a general method for the synthesis carbon substituted furanes/oxazoles. Halogenated furanes/oxazoles lv can be treated with an alkyne in the presence of a suitable catalyst, for example Pd(PPh$_3$)$_4$, CuI, base, such as TEA in a suitable solvent, like DCM to afford alkynes lvii (Method C). Compounds lvii can be then reduced to alkyl substituted furanes/oxazoles using well known techniques, for example hydrogenation with Pd/C in a suitable solvent, such as ethanol.

Scheme 14: General method for introducing carbon functionality to halogentated furanes/oxazoles.

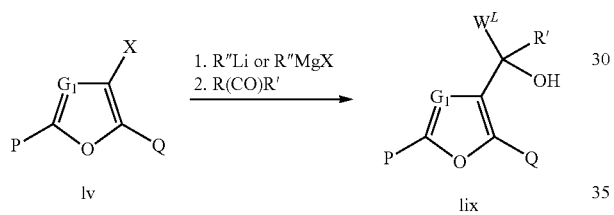

Scheme 14 above shows a general method for the synthesis carbon substituted furanes/oxazoles lix. Halogenated furanes/oxazoles lv can be treated with alkyllithium, arryllithium or alkylmagnesium reagents, such as of n-BuLi at low temperature to generate metallated intermediates that are subsequently treated with aldehydes or ketones to afford carbinols lix (Method D).

Scheme 15: General method for introducing carbon functionality to 4-halogentated furanes/oxazoles.

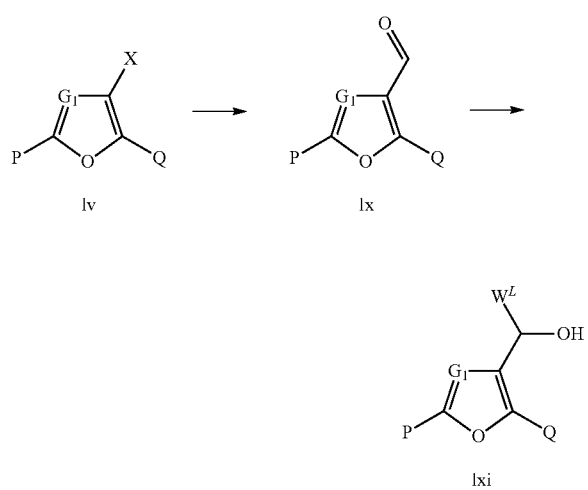

Scheme 15 above shows a general method for the synthesis carbon substituted furanes/oxazoles. Halogenated furanes/oxazoles lv can be treated with vinylorganometallic reagents, for example vinyltributylstannane under Stille conditions (Method C), or vinyltrifluoroborate under Suzuki conditions (Method A) to afford vinyl furanes/oxazoles, that can be oxidized to aldehydes lx using a suitable method, for example OsO$_4$, sodium periodate in water-dioxane mixture. Aldehydes lx can be then treated with organometallic reagents, such as Grignard or alkyl/aryllithium compounds in a suitable solvent, such as THF at low temperature to afford carbinols of formula lxi (Method D).

Scheme 16: General method for the synthesis of ethers

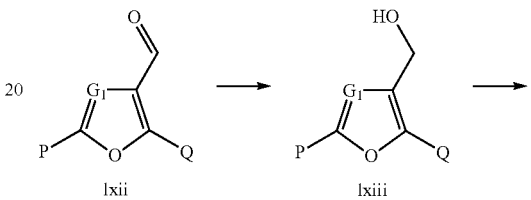

Scheme 16 above shows a general method for the synthesis of alcohols lxiii and ethers lxiv. Aldehydes prepared as described in Scheme 15 above can be treated with a suitable reducing agent, such as NaBH$_4$ in an appropriate solvent, for example THF to afford alcohols of formula lxiii. Alcohols lxiii can be then alkylated using standard conditions, for example with alkyl halides in the presence of base, such as K$_2$CO$_3$ in THF to afford ethers lxiv (Method E).

Scheme 17: General method for the synthesis of amines

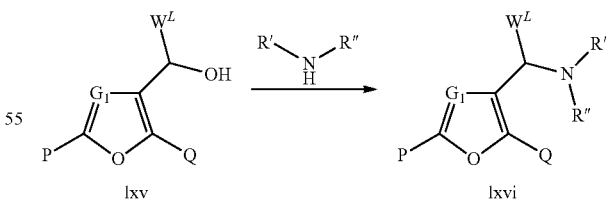

Scheme 17 above shows a general method for the synthesis of amines lxvi. As shown is Scheme 17, alcohols lxv can be activated via sulfonyl esters, for example by reaction with methanesulfonic chloride and a base, such as pyridine in a suitable solvent, for example DCM. Sulfonyl esters are then treated with amines at elevated temperature to provide target amines lxvi (Method E).

Scheme 18: General method for the synthesis of ethers

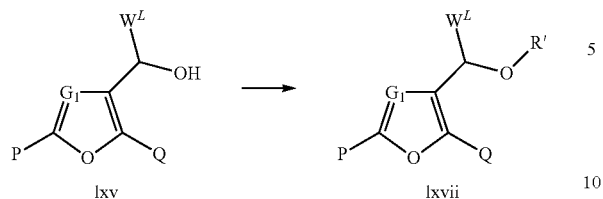

Scheme 18 above shows a general method for the synthesis of ethers lxvii when $W^L$ is an aromatic or heteroaromatic group. As shown is Scheme 18, alcohols lxv are treated with an excess of alcohol, such as methanol in the presence of an acid, like aqueous HCl with an optional cosolvent, for example dioxane at ambient temperature to afford ethers of formula lxvii.

Scheme 19: General method for Pd-catalyzed amination/amidation of halogenated furanes/oxazoles

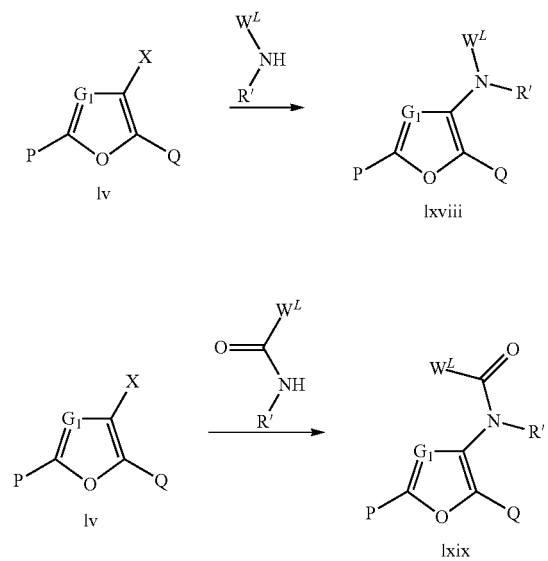

As shown in Scheme 19, amine or amide functionality can be introduced by the well known palladium catalyzed amination/amidation reaction, so called Buchwald coupling, to the 4-halogenated thiophenes/thiazoles lv.

For example, halides lv can be treated with amines using an appropriate Pd catalyst, such as $Pd_2 dba_3$/BINAP, with a suitable solvent/base combination, for example NaOtBu in toluene at elevated temperature or using microwave irradiation to afford amines of formula lxviii (Method G).

Coupling with amides also can be carried out using a suitable Pd catalyst, for example $Pd_2 dba_3$/XantPhos, with a suitable solvent/base combination, like $Cs_2CO_3$ in dioxane at elevated temperature or using microwave irradiation to give amides of formula lxix (Method H).

Schemes 20-29 describe methods for introduction and modification of $R_1$ groups.

Scheme 20: General route for the synthesis of carboxamides

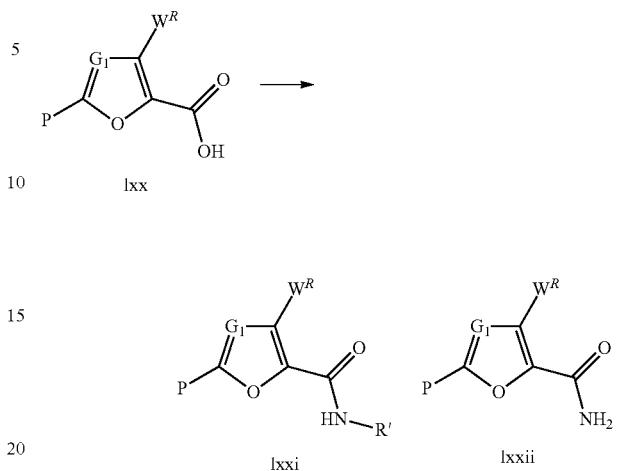

Scheme 20 above shows a general route for preparing amide compounds of formula lxxi. As shown in Scheme 20, acids lxx are treated with amines using standard coupling conditions, such as EDCI and HOBt in DCM to afford amides lxxi (Method I).

When ammonia is used as an amine source, obtained primary amide derivatives lxxii can be very useful intermediates for the construction of azoles as described below.

Scheme 21:
General route for the synthesis of halogenated furanes/oxazoles by Hunsdiecker reaction

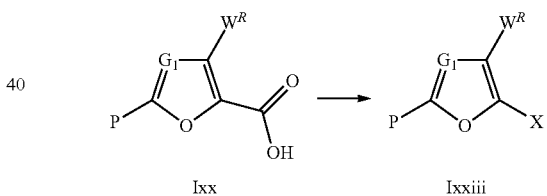

As shown Scheme 21, halogenated furanes/oxazoles lxxiii can be prepared by the Hunsdiecker reaction of carboxylic acid analogs lxx.

As shown in Scheme 21, acids lxx are treated with sliver hydroxide to form a silver salt, which is subsequently treated with halogen, for example bromine in a suitable solvent, such as $CCl_4$ at elevated temperature to form lxxiii (Method J).

Scheme 22: General route for the construction of 1,2,4-triazolyl

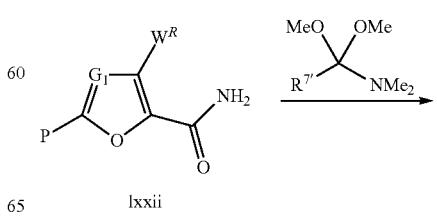

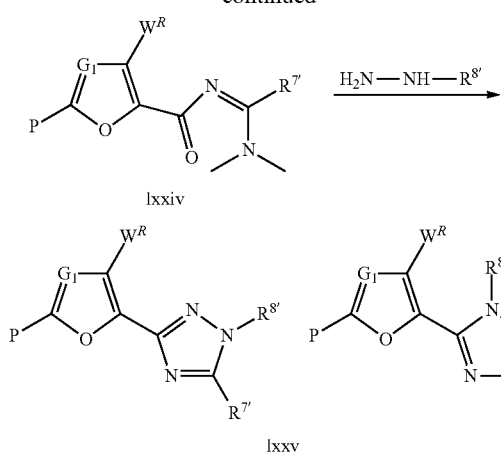

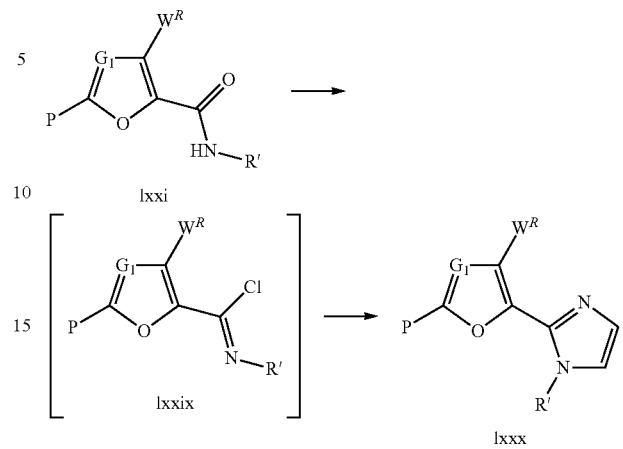

Scheme 24: Alternative route for the construction of 2-imidazolyl

As shown in Scheme 22, amides lxxii, which can be prepared by the procedure described in scheme 20, can be treated with DMFDMA or similar reagents at elevated temperature or under microwave irradiation to give intermediate amidines lxxiv that are transformed to 1,2,4-triazoles lxxv, for example using hydrazine or substituted hydrazines in acetic acid at elevated temperature or under microwave irradiation (Method K).

Scheme 24 above shows an alternative route for preparing imidazoles of formula lxxx. As shown in Scheme 24, amides lxxi are cyclized to imidazoles through a 3-step one pot process that involves treatment with phosphorus pentachloride and HCl in dioxane to afford carbimidoyl chloride intermediates lxxix that are then treated with aminoacetaldehyde dimethylacetal followed by HCl in dioxane at elevated temperature to give lxxx. When R'=allyl, benzyl or substituted benzyl, it can also serve as a protecting group.

Scheme 23: General route for the construction of 2-imidazolyl

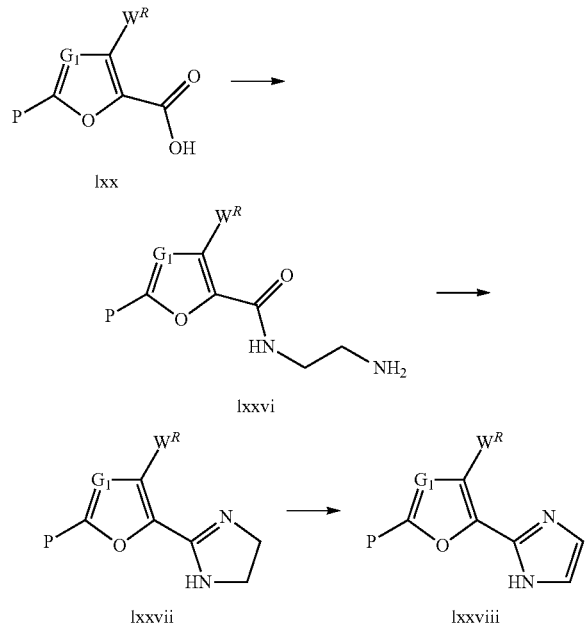

As shown in Scheme 23, acids lxx are treated with Boc protected ethylenediamine using standard coupling conditions, such as EDCI and HOBt in DCM (Method I). Protective group is removed using an appropriate acid, for example TFA in DCM to give amide lxxvi. Cyclization of lxxvi is achieved using suitable conditions, for example POCl₃ to form dihydroimidazoles lxxvii. Dihydroimidazoles lxxvii can be oxidized to imidazoles lxxviii using a suitable oxidative method, for example heating with Magtrieve.

Scheme 25: General route for the construction of substituted 4-imidazolyl.

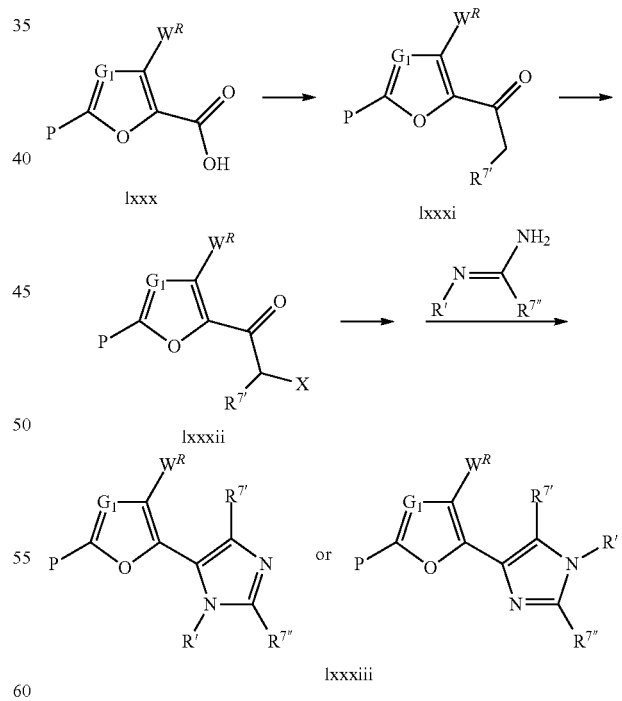

As shown in Scheme 25, acids lxxx are transformed to ketones lxxxi using a suitable synthetic sequence, for example through a coupling with N,O-dimethylhydroxylamine and subsequent treatment of the resulting Weinreb amides with alkyllithium or Grignard reagents in a suitable solvent, like THF (L).

Ketones lxxxi are then halogenated with a suitable reagent, such as bromine or NBS in an appropriate solvent, like DCM to form alpha-halogenated ketones lxxxii (X=halogen). Alternatively, treatment of ketones lxxxi with a suitable oxidative sulfonylating agent, like hydroxy(tosyloxy)iodobenzene using suitable conditions, for example heating in acetonitrile affords sulfonyl esters of formula lxxxii (X=OSO$_2$R).

Treatment of lxxxii with amidine reagents in the presence of a suitable base, like potassium carbonate in a suitable solvent, such as THF-water mixture at elevated temperature or microwave irradiation affords the final imidazoles lxxxiii. Alternatively, compounds lxxxii can be treated with large excess of amides, such as formamide using microwave irradiation to afford imidazoles lxxxiii.

Scheme 26: General route for the construction of 3-pyrazolyl.

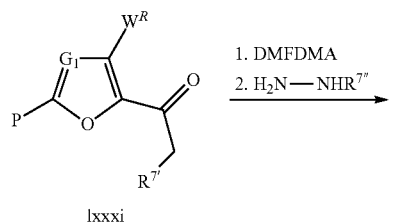

lxxxi

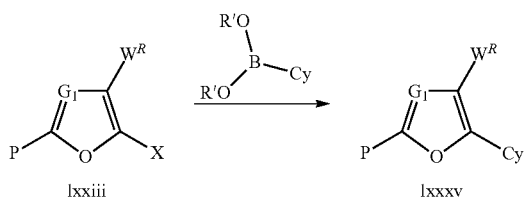

lxxxiv

As shown in Scheme 26, ketones lxxxi, which can be prepared by the procedure describing in scheme 25, are treated with DMFDMA to afford an intermediate enamines followed by reaction with substituted hydrazine, or hydrazine hydrate in a suitable solvent, for example acetic acid to give pyrazoles lxxxiv.

Scheme 27: General route for the introduction of heteroaromatic group.

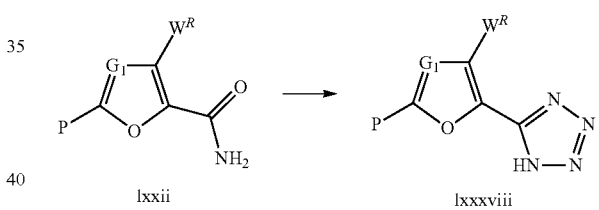

lxxiii                    lxxxv

As shown in Scheme 27, halides lxxiii which can be prepared by the procedure described in scheme 21, are treated with heteroaryl boronic acids or esters, in the presence of a suitable catalyst, for example Pd(PPh$_3$)$_4$, using a base, such as cesium carbonate in a suitable solvent, like dioxane-water mixture at elevated temperature to afford compounds of formula lxxxv (Method A).

Scheme 28: General route for the construction of 1,2,3-triazolyl.

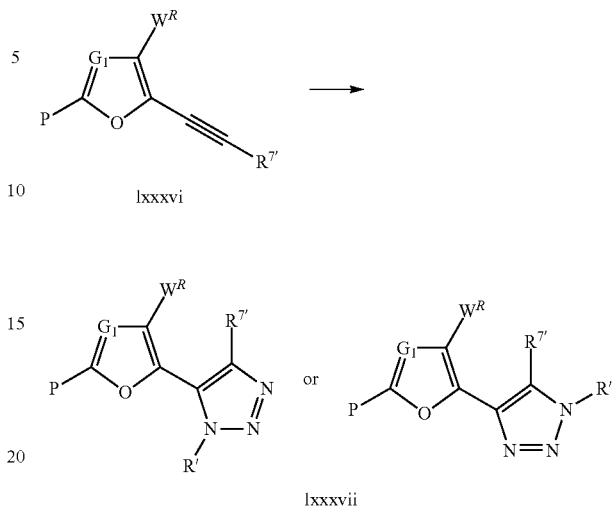

lxxxvi lxxxvii

As shown in Scheme 28, alkynes lxxxvi, which can be prepared by the known Stille- or Sonogashira-coupling reaction of halide lxxiii and appropriate alkyne derivative, are treated with azides, inorganic or organic a suitable solvent, such as dioxane at elevated temperature to afford triazoles of formula lxxxvii.

Scheme 29: General route for the construction of tetrazolyl.

lxxii                    lxxxviii

As shown in Scheme 29, amides lxxii, which can be prepared by the procedure described in scheme 20, are treated with an azide source, for example sodium azide using a suitable Lewis acid, for example silicon tetrachloride in an appropriate solvent, such as acetonitrile to give tetrazoles lxxxviii.

Scheme 30-36 describe general procedure for the functional group transformation on Hy.

Scheme 30: General method for the introduction of amino group to 2-fluoropyridyl

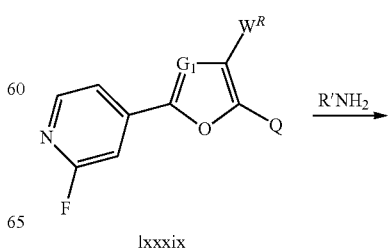

lxxxix

-continued

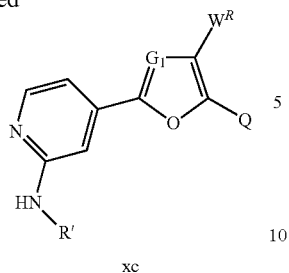

xc

Scheme 30 above shows a general route for the transformation of 2-fluoropyridyl to 2-substituted aminopyridyl to give the compounds of formula xc.
As shown in Scheme 30, compounds lxxxix can be treated with amines at elevated temperature or under microwave irradiation to give 2-aminopyridines xc.

Scheme 31: General method for the introduction of 2-acylaminopyridines by Buchwald reaction

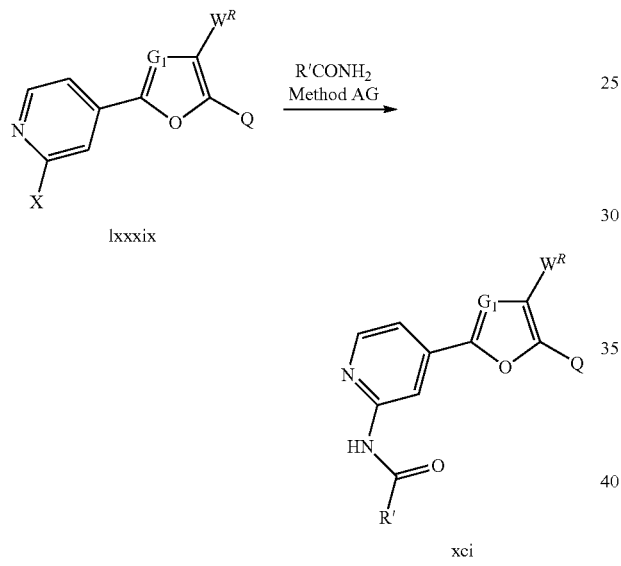

Scheme 31 above shows a general route for the transformation of 2-halopyridyl to 2-acylaminopyridyl by Buchwald reaction to give the compounds formula xci.
As shown in Scheme 31, compounds lxxxix can be treated with amides or carboxamides in the presence of a suitable catalyst, such as Pd$_2$dba$_3$, XantPhos, base like cesium carbonate in an appropriate solvent, for example dioxane at elevated temperature or under microwave irradiation to give acylaminopyridines xci (Method H).

Scheme 32: General method for the synthesis of 2-aminopyrimines

-continued

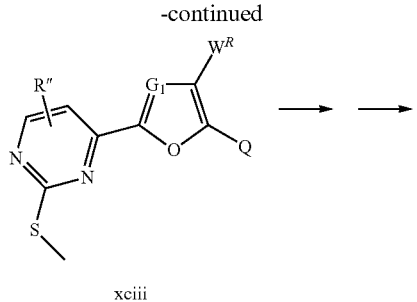

xciii

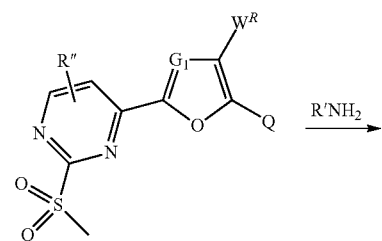

xciv

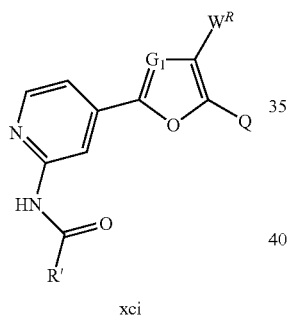

xcv

As shown in Scheme 32, compounds xcii can be coupled with stannanes under suitable conditions, for example Pd(PPh$_3$)$_4$, CuI, LiCl in dioxane at elevated temperature to give compounds xciii (Method A). Oxidation of thioethers xciii to sulfones xciv can be achieved using a suitable oxidant, for example mCPBA in DCM. Methanesulfonyl group of sulfones xciv can be displaced by treatment with amines in a suitable solvent, for example THF to afford 2-aminopyrimidines xcv.

Scheme 33: General method for the introduction of 2-halo substituent on 4-pyridyl group

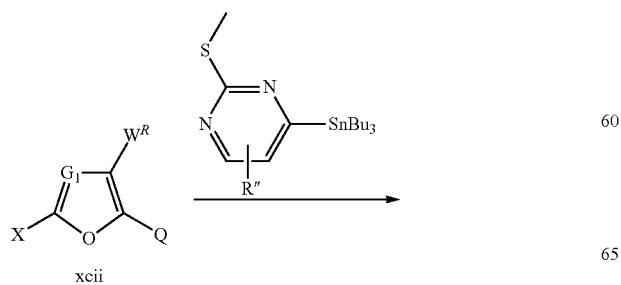

-continued

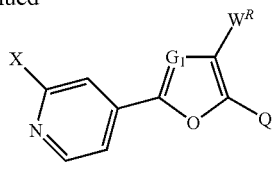

xcviii

Scheme 33 above shows a general route for the transformation of 4-pyridyl to 2-halo-4-pyridyl compounds formula xcvviii.

As shown in Scheme 33, compounds xcvi can be treated with an oxidant, for example mCPBA in a suitable solvent, such as DCM to afford intermediate N-oxides xcvii, that are halogenated in 2-position using phosphoryl halides, for example phosphoryl chloride at elevated temperature to afford compounds of formula xcviii.

Scheme 34: General method for the preparation of 2-aminooxazoles

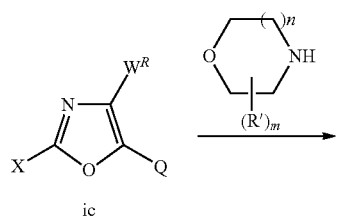

ic

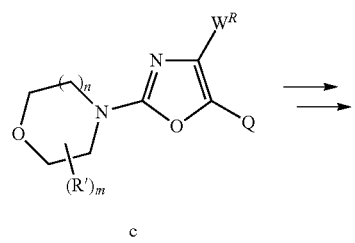

c

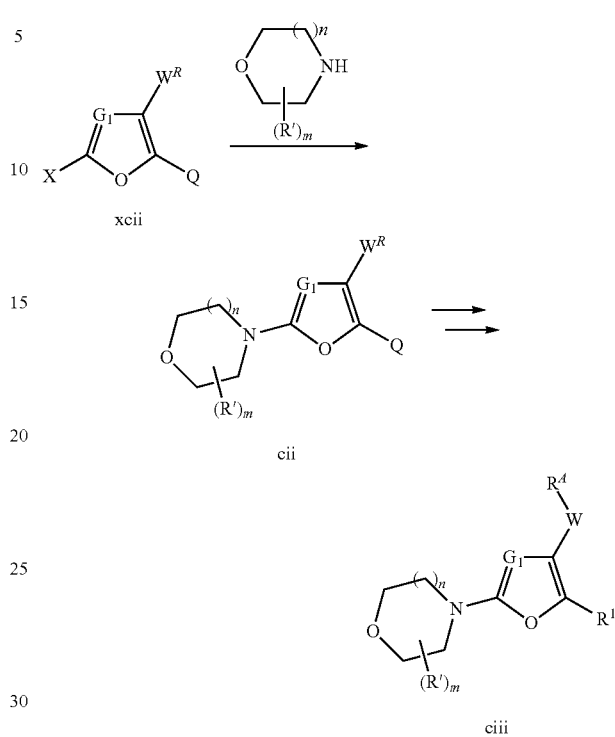

ci

Scheme 34 shows a general method for preparation of compounds of formula ci. As shown in scheme 34, 2-halooxazoles are treated with amines at elevated temperature, either neat, or in a suitable solvent, such as NMP with an appropriate base, for example $K_2CO_3$ (Method F) to afford 2-aminooxazoles c, that can be further transformed to compounds ci using generally known methods.

Scheme 35: General method for the preparation of 2-aminofuranes/oxazoles

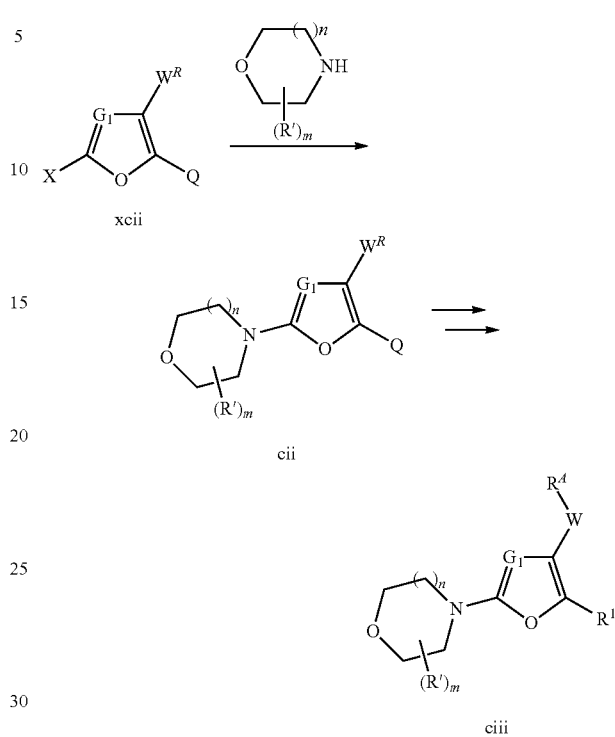

Scheme 35 shows a general method for preparation of compounds of formula ci. As shown in scheme 34, 2-halofuranes/oxazoles xcii are treated with amines using an appropriate Pd catalyst, such as $Pd_2$ $dba_3$/BINAP, with a suitable solvent/base combination, for example NaOtBu in toluene at elevated temperature or using microwave irradiation to afford amines of formula cii (Method G), that can be further transformed to compounds ciii using generally known methods.

Scheme 36: General method for coupling of halofuranes/oxazoles with vinylstannanes

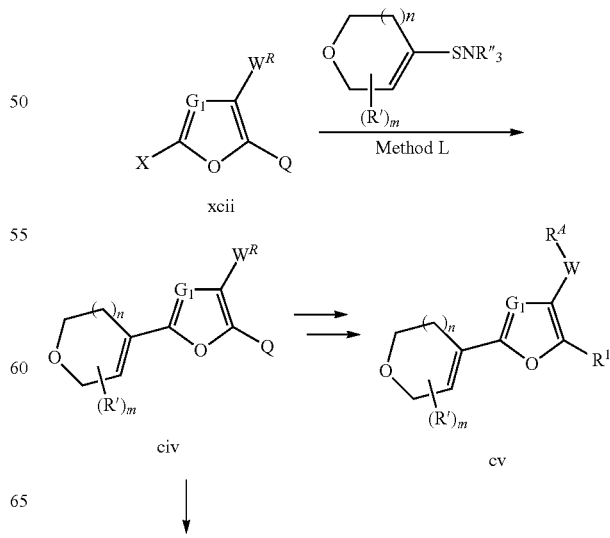

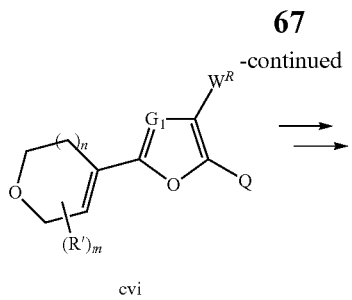

cvi

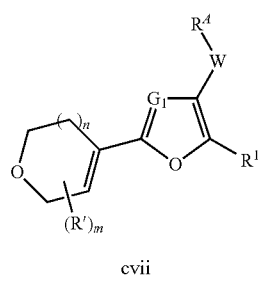

cvii

Scheme 36 shows a general method for preparation of compounds of formula cv and cvii. As shown in Scheme 36, compounds xcii can be coupled with vinylstananes under suitable conditions, for example Pd(PPh₃)₄, CuI, LiCl in dioxane under elevated temperature to give alkenes civ (Method A), that can be further transformed to compounds cv by generally known methods. Alternatively, hydrogenation of civ, for example using Pd/C as catalyst in a suitable solvent, such as ethanol can afford compounds cvi that can be further transformed to cvii by generally known methods.

Schemes 37-45 describe the procedures for the synthesis of building blocks for Hy.

Scheme 37: General method for the synthesis of imidazo[1,2-a]pyridine building blocks.

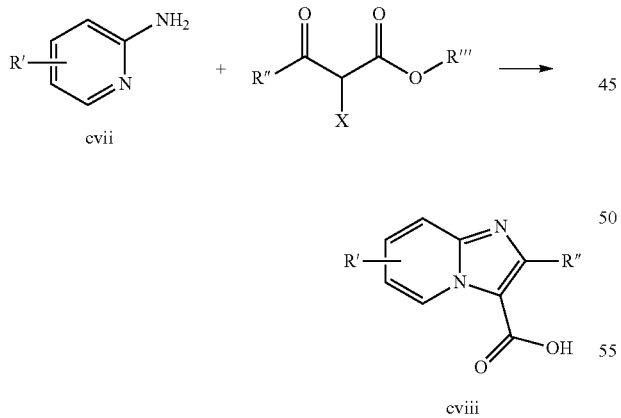

Scheme 37 above shows a general method for the synthesis of midazo[1,2-a]pyridines cviii. As shown in Scheme 37, 2-aminopyridines cvii are condensed with α-halogenated beta-ketoesters in a suitable solvent, for example ethanol at elevated temperature to afford intermediate esters, that are hydrolyzed using standard conditions, such as aqueous sodium hydroxide in THF followed by acidic workup to give acids cviii.

Scheme 38: General method for the synthesis of imidazo[1,2-b]pyridazine building blocks

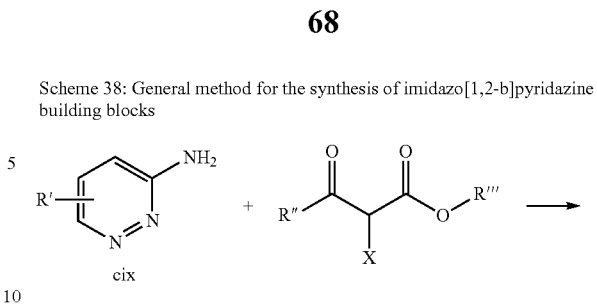

Scheme 38 above shows a general method for the synthesis of imidazo[1,2-b]pyridazines cx. As shown in Scheme 38, 2-aminopyridazines cix are condensed with α-halogenated beta-ketoesters in a suitable solvent, for example ethanol at elevated temperature to afford intermediate esters, that are hydrolyzed using standard conditions, such as aqueous sodium hydroxide in THF followed by acidic workup to give acids cx (Method CG).

Scheme 39: General method for the synthesis of imidazo[2,1-b][1,3]thiazole building blocks

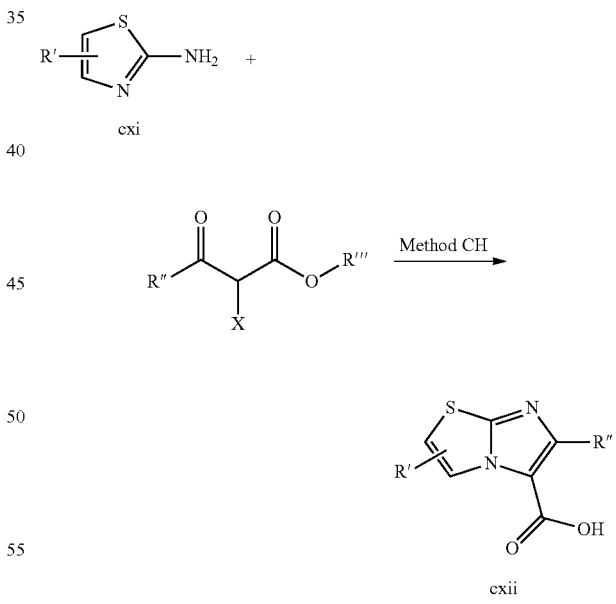

Scheme 39 above shows a general method for the synthesis of imidazo[2,1-b][1,3]thiazoles cxii.

As shown in Scheme 39, 2-aminothiazoles cxi are condensed with α-halogenated β-ketoesters in a suitable solvent, for example ethanol at elevated temperature to afford intermediate esters, that are hydrolyzed using standard conditions, such as aqueous sodium hydroxide in THF followed by acidic workup to give acids cxii.

Scheme 40: General method for the synthesis of pyrazolo[1,5-a]pyridine building blocks

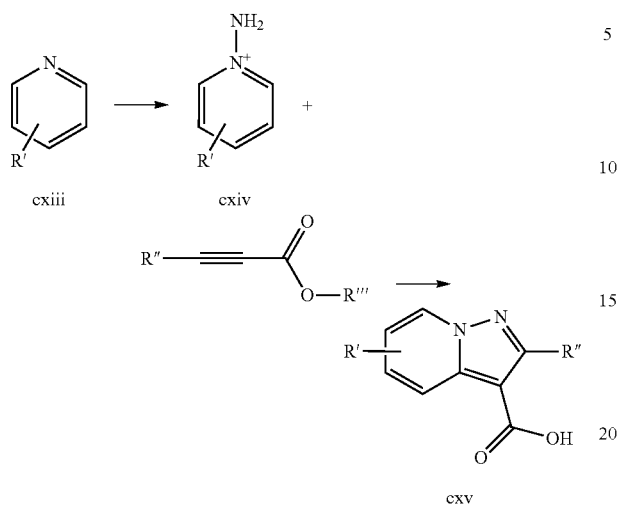

Scheme 40 above shows a general method for the synthesis of pyrazolo[1,5-a]pyridines cxv. As shown in Scheme 40, pyridines cxiii are N-aminated with a suitable agent, such as O-(mesitylsulfonyl)hydroxylamine using appropriate conditions, for example toluene or ethyl acetate as solvent. Resulting N-aminopyridinium salts cxiv are then condensed with alkynylcarboxylic acid esters with a suitable base, such as potassium carbonate in a suitable solvent, for example DMF to afford intermediate esters, that are hydrolyzed using standard conditions, such as aqueous sodium hydroxide in THF followed by acidic workup to give acids cxv.

Scheme 41: General method for the synthesis of pyrazolo[5,1-b][1,3]thiazole building blocks

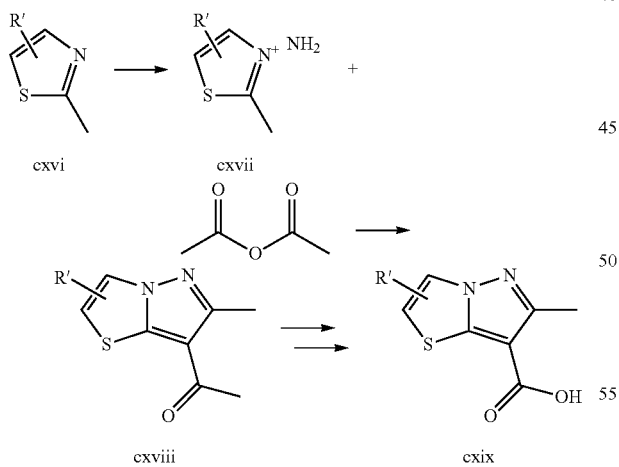

Scheme 41 above shows a general method for the synthesis of pyrazolo[5,1-b][1,3]thiazoles cxix.
As shown in Scheme 41, 2-methylthiazoles cxvi are N-aminated with a suitable agent, such as O-(mesitylsulfonyl)hydroxylamine using appropriate conditions, for example toluene or ethyl acetate as solvent. Resulting N-aminothiazolium salts cxvii are then condensed with acetic anhydride and potassium acetate at elevated temperature to afford methyl ketone intermediate cxviii, which can be converted to carboxylic acid cxix moiety by well known functional transformation of methyl keton to carboxylic acid.

Scheme 42: Alternative method for the synthesis of pyrazolo[5,1-b][1,3]thiazole derivatives

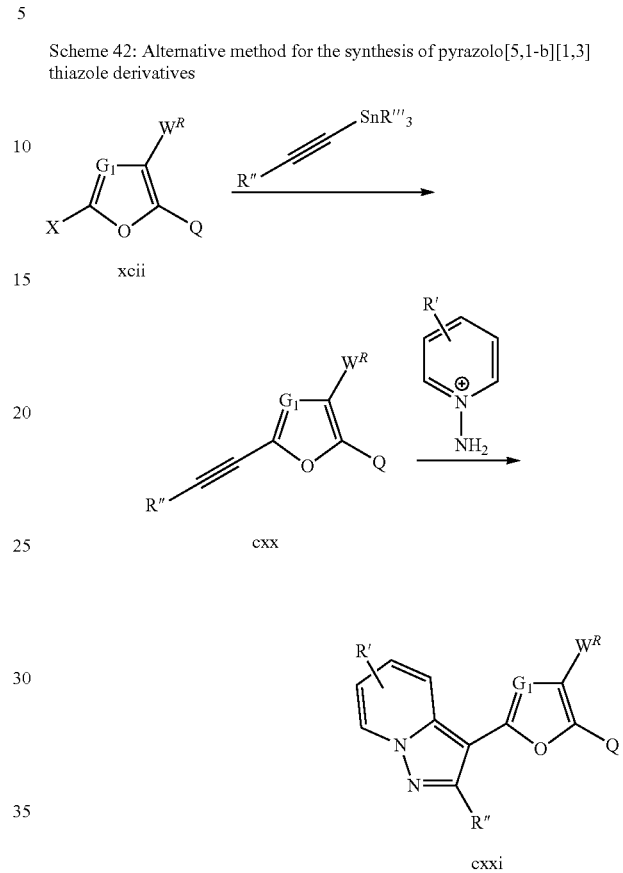

Scheme 42 above shows an alternative method for the synthesis of pyrazolopyridines cxxi. As shown in Scheme 42, halides xcii are treated with alkynyl stannanes in the presence of a suitable catalysts, such as Pd(PPh$_3$)$_4$, CuI, with LiCl in an appropriate solvent, like dioxane at elevated temperature to give alkynes of formula cxx (Method A). Alkynes cxx are then coupled with N-aminopyridinium salts with a base, like potassium carbonate in a suitable solvent, for example DMF to afford compounds of formula cxxi.

Scheme 43: Alternative method for the synthesis of imidazo[1,2-a]pyridine building blocks.

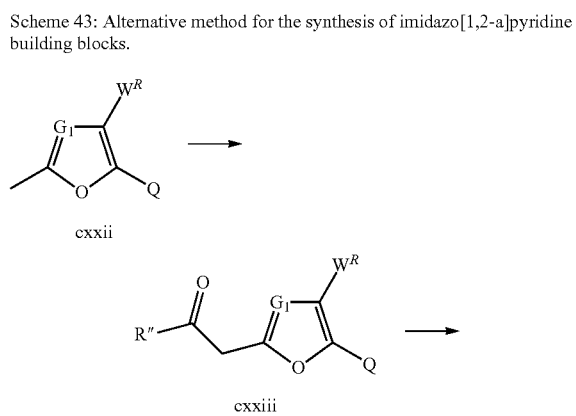

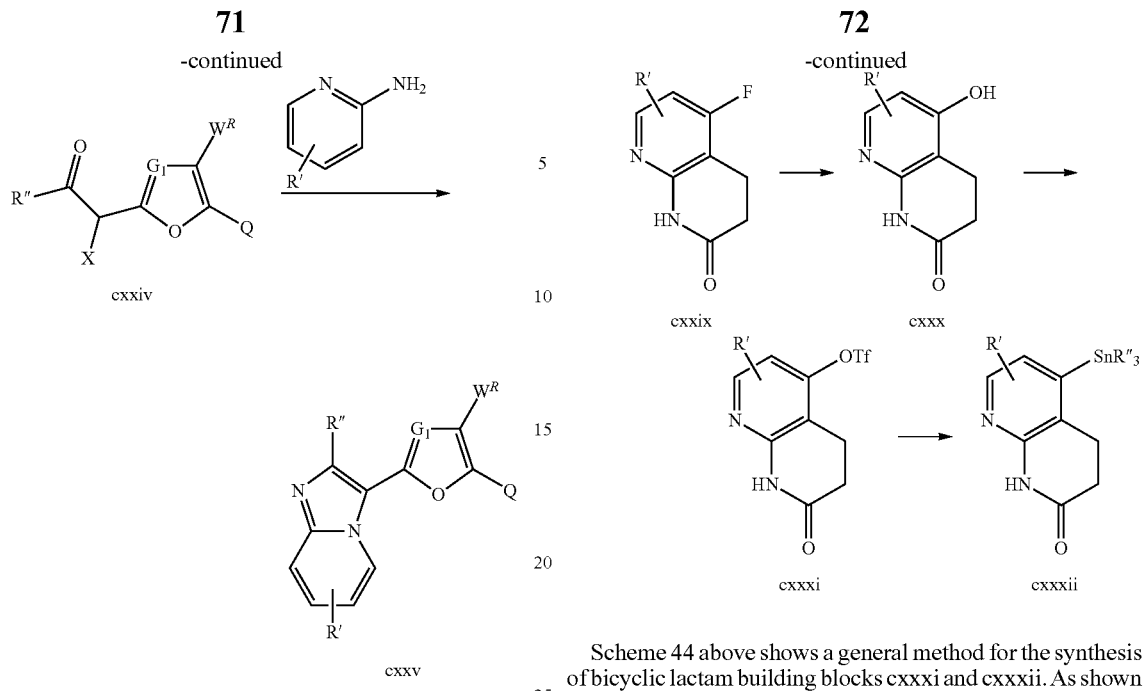

Scheme 43 above shows an alternative method for the synthesis of imidazolopyridines cxxv. As shown in Scheme 43, 2-methylthiazoles cxxii are deprotonated with a suitable reagent, such as n-BuLi and subsequently treated with Weinreb amides in a suitable solvent, such as THF to give ketones cxxiii (Method L). Halogenation of ketones is achieved using standard conditions, for example NBS in DCM and the resulting haloketones cxxiv are then treated with aminopyridines in a suitable solvent, for example ethanol at elevated temperature to give compounds of formula cxxv.

Scheme 44: General method for the synthesis of bicyclic lactam building blocks

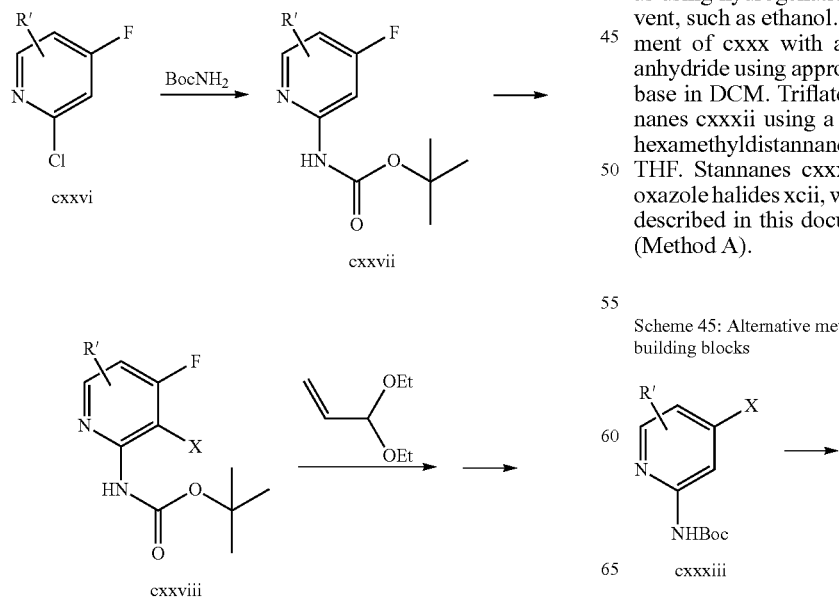

Scheme 44 above shows a general method for the synthesis of bicyclic lactam building blocks cxxxi and cxxxii. As shown in Scheme 44, substituted 2-chloro-4-fluoropyridines can be amidated, for example with $BocNH_2$, $Pd_2 dba_3$ and a suitable ligand, such as X-Phos in the presence of a base, for example cesium carbonate in an appropriate solvent, like dioxane to afford Boc-protected 2-aminopyridines cxxvii (Method H). Compounds cxxvii can be deprotonated, for example using n-BuLi/TMEDA in THF at low temperature and then quenched with a molecule of halogen, such as iodine in THF to give halogenated compounds cxxviii. Compounds cxxviii can be coupled with diethoxypropene using a suitable Pd catalyst, such as Di-mu-chlorobis[5-hydroxy-2-[1-(hydroxy-imino-kappaN)ethyl]phenyl-kappaC]palladium(II) dimer with an appropriate base, like N,N-diisopropylethylamine in a suitable solvent, for example DMF-water mixture (Method M) to afford lactams of formula cxxix. Transformation of fluoro cxxix into hydroxyl analogs cxxx can be carried out using a standard procedure, for example treatment with benzyl alcohol in the presence of a base, such as sodium hydride at elevated temperature and subsequent debenzylation, such as using hydrogenation with Pd/C catalyst in a suitable solvent, such as ethanol. Triflates cxxxi can be formed by treatment of cxxx with a suitable reagent, for example triflic anhydride using appropriate conditions, such as pyridine as a base in DCM. Triflates cxxxi can be transformed into stannanes cxxxii using a suitable method, such as heating with hexamethyldistannane, $Pd(PPh_3)_4$ in a suitable solvent, like THF. Stannanes cxxxii can be then coupled with furane/oxazole halides xcii, which can be prepared by the procedures described in this document using standard Stille conditions (Method A).

Scheme 45: Alternative method for the synthesis of bicyclic lactam building blocks

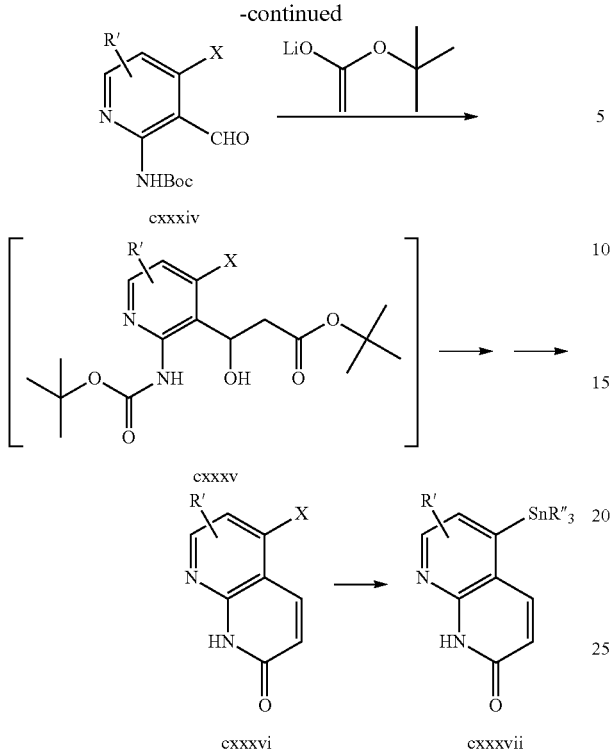

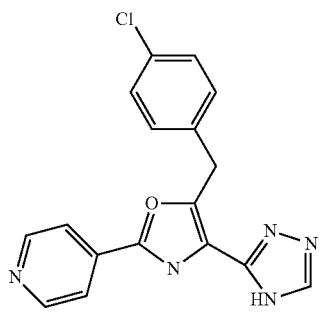

Scheme 45 above shows an alternative method for the synthesis of bicyclic lactam building blocks cxxxvii. As shown in Scheme 45, compounds cxxxiii can be deprotonated with a suitable reagent, such as n-BuLi in THF at low temperature and then treated with DMF to produce carbaldehydes cxxxiv. Aldehyde group in cxxxiv can be then treated with enolate generated from t-Butylacetate and LDA in a suitable solvent, such as THF at low temperature to form intermediate β-hydroxyesters cxxxv that can be cyclized to lactams cxxxvi using an acid, such as HCl in water at elevated temperature. Halides cxxxvi can be transformed to stannanes cxxxvi, for example using hexamethyldistannane, Pd(PPh$_3$)$_4$ in a suitable solvent, like THF. Stannanes cxxxv can be then coupled with thiophene/thiazole halides xcii, which can be prepared by the procedures described in this document using standard Stille conditions to afford compounds cxxxvii (Method A).

EXAMPLES

Table 1 below depicts certain compounds represented by compounds of general formula IA and IB.

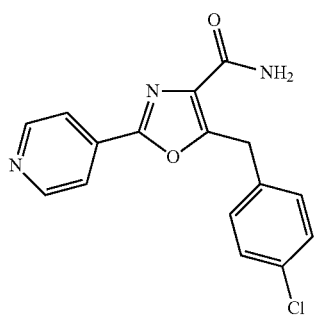

Definitions
AcOH acetic acid
ACN acetonitrile
ATP adenosine triphosphate
br broad
BCA bicinchoninic acid
BSA bovine serum albumin
BOC tert-butoxycarbonyl
BuLi butyllithium
m-CPBA m-chloroperbenzoic acid
d doublet
dd doublet of doublets
DCE dichloroethane
DCM dichloromethane
DDQ 2,3-dichloro-5,6-dicyano-1,4-benzoquinone
DIPEA diisopropylethyl amine
DMAP N,N-dimethylaminopyridine
DME 1,2-Dimethoxyethane
DMEM Dulbecco's Modified Eagle's Medium
DMF N,N-dimethylformamide
DMF-DMA N,N-dimethylformamide dimethyl acetal
DMSO dimethylsulfoxide
DPPA diphenylphosphoryl azide
DTT dithiothreitol
dppf diphenylphosphinoferrocene
EDCI N-(3-dimethylaminopropyl)-N'-ethylcarbodiimide hydrochloride
EDTA ethylenediaminetetraacetic acid
EtOAc ethyl acetate
EtOH ethanol
FA formic acid
FBS fetal bovine serum
J coupling constant
h hours
Hz: hertz
HATU N,N,N',N'-tetramethyl-o-(7-azabenzotriazole-1-yl)uronium hexafluorophosphate
HBTU o-benzotriazol-1-yl-N,N,N',N'-tetramethyluronium hexafluorophosphate
HEPES N-(2-Hydroxyethyl)piperazine-N'-(2-ethanesulfonic acid)
HOBT 1-hydroxybenztriazole hydrate
HRMS high resolution mass spectrum
LAH lithium aluminum hydride
LCMS liquid chromatography mass spectrum
LDA lithium diisopropylamide
LiHMDS Lithium bis(trimethylsilyl)amide
m multiplet
m/z mass to charge
Me methyl
MeOH methanol
min minutes MS mass spectrum
MTT methylthiazoletetrazolium
MWI microwave irradiation
NBS N-bromosuccinimide
PBS phosphate buffered saline
PKA cAMP-dependent protein kinase
rt room temperature
s singlet
t triplet
TEA triethylamine
TFA: trifluoroacetic acid
TFFA trifluoroacetic anhydride
THF tetrahydrofuran
TMB 3,3',5,5'-Tetramethylbenzidine
TMEDA Tetramethylethylenediamine
q quartet
WST (4-[3-(4-iodophenyl)-2-(4-nitrophenyl)-2H-5-tetrazolio]-1,3-benzene disulfonate sodium salt)

Example 1

Synthesis of 5-(4-chlorobenzyl)-2-pyridin-4-yl-1,3-oxazole-4-carboxamide (Compound 1) and 4-[5-(4-chlorobenzyl)-4-(4H-1,2,4-triazol-3-yl)-1,3-oxazol-2-yl]pyridine (Compound 2)

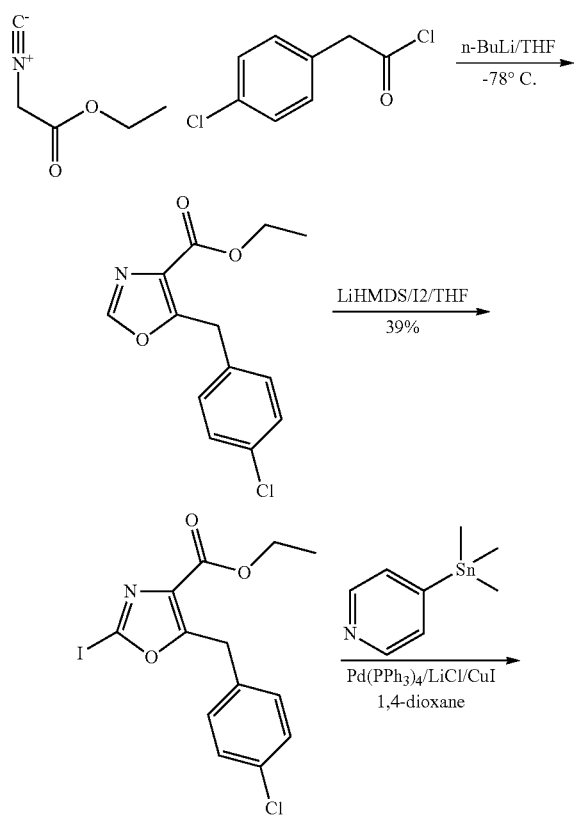

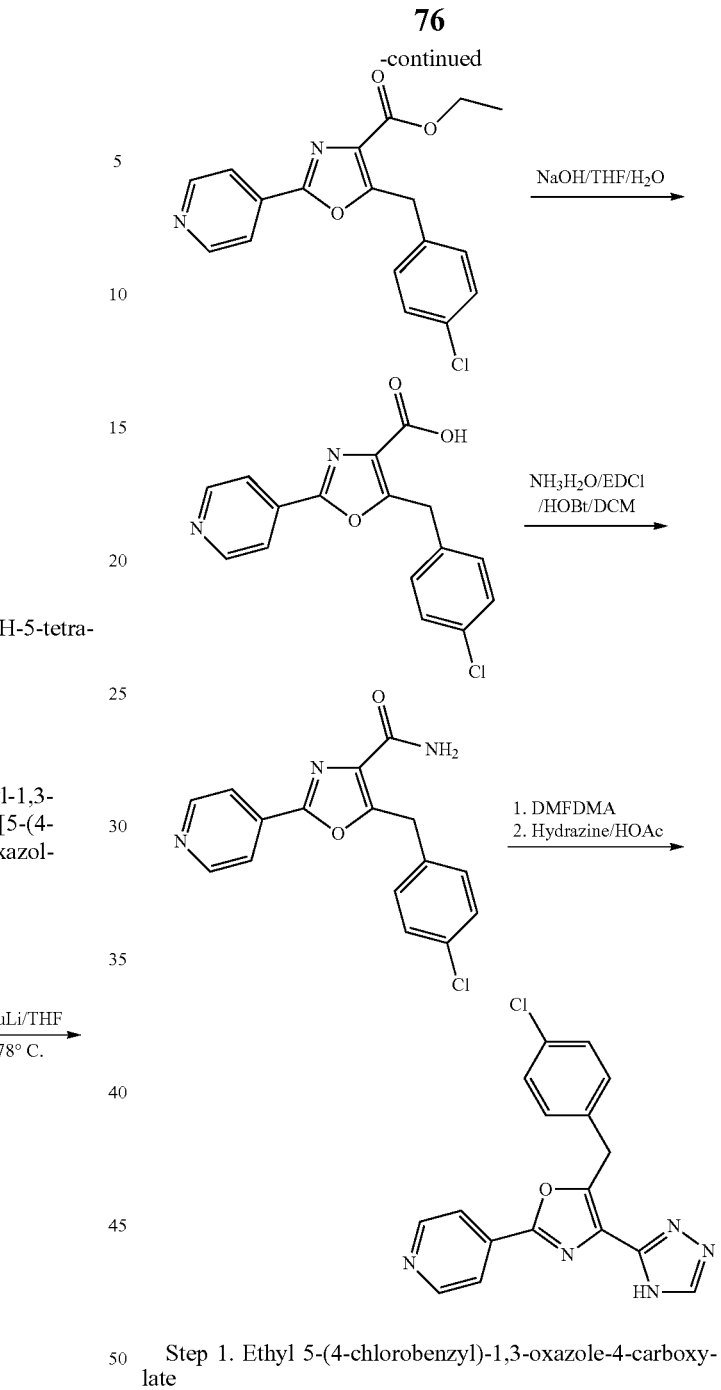

Step 1. Ethyl 5-(4-chlorobenzyl)-1,3-oxazole-4-carboxylate

To a solution of Ethyl isocyanoacetate (1.00 mL, 9.15 mmol) in Tetrahydrofuran (43 mL) at −78° C. was added 2.5 M n-Butyllithium (9.15 mmol, 9.15 mmol) in hexanes under argon. The mixture was stirred for 20 min. 4-Chlorophenylacetyl chloride (0.753 g, 3.98 mmol) in Tetrahydrofuran (11 mL, 130 mmol) was added at the same temperature. After 1 h, the temperature was raised to rt and then quenched by acetic acid (0.38 g, 6.3 mmol). The mixture was washed with saturated sodium bicarbonate and brine. The organic layer was collected and dried over sodium sulfate. After evaporation, the mixture was purified by chromatography to afford ethyl 5-(4-chlorobenzyl)-1,3-oxazole-4-carboxylate (0.83 g, 78%). LCMS: (FA) ES+ 266.3.

Step 2. Ethyl 5-(4-chlorobenzyl)-2-iodo-1,3-oxazole-4-carboxylate

To a solution of Ethyl 5-(4-chlorobenzyl)-1,3-oxazole-4-carboxylate (0.447 g, 1.68 mmol) in Tetrahydrofuran (13.64 mL) was added 1M Lithium bis(trimethylsilyl)amide (1.851 mmol, 1.851 mmol) in hexanes slowly at −78° C. under argon. The mixture was stirred at the same temperature for 30 min and iodine (0.546 g, 2.15 mmol) was added. The mixture was stirred at −78° C. for 30 min and then raised to rt. The mixture was quenched by sodium bisulfite solution and the organic layer was collected, dried and evaporated to afford a residue. Purified by chromatography Ethyl 5-(4-chlorobenzyl)-2-iodo-1,3-oxazole-4-carboxylate (0.26 g, 40%). LCMS: (FA) ES+: 392.0

Step 3. Ethyl 5-(4-chlorobenzyl)-2-pyridin-4-yl-1,3-oxazole-4-carboxylate

A mixture of Ethyl 5-(4-chlorobenzyl)-2-iodo-1,3-oxazole-4-carboxylate (261 mg, 0.666 mmol), Tetrakis(triphenylphosphine)palladium(0) (38.5 mg, 0.0333 mmol), Copper(I) iodide (38.1 mg, 0.200 mmol) and Lithium chloride (84.8 mg, 2.00 mmol) under atmosphere of argon was dissolved in 1,4-Dioxane (18 mL) and Trimethyl(4-pyridyl)tin (207 uL, 1.20 mmol) was added. The mixture was heated at 100° C. for 2 h. The mixture was evaporated and the residue was purified by chromatography to afford Ethyl 5-(4-chlorobenzyl)-2-pyridin-4-yl-1,3-oxazole-4-carboxylate (0.133 g, 58.2%). LCMS (FA) ES+ 343.2, 345.1

Step 4 and 5. 5-(4-chlorobenzyl)-2-pyridin-4-yl-1,3-oxazole-4-carboxamide

To the mixture of Ethyl 5-(4-chlorobenzyl)-2-pyridin-4-yl-1,3-oxazole-4-carboxylate (0.167 g, 0.487 mmol) in Tetrahydrofuran (10.0 mL) was added 1M Sodium hydroxide (2.92 mmol, 2.92 mmol) in water. The mixture was stirred at rt overnight. The reaction mixture was concentrated and then acidified with 1N HCl to pH 3. The precipitate was collected, dried and used in the next step directly. LCMS: (FA) ES+: 315.3, 317.0

A mixture of the above acid, N-(3-Dimethylaminopropyl)-N′-ethylcarbodiimide hydrochloride (0.187 g, 0.974 mmol) and HOBT (0.112 g, 0.731 mmol) and 25% aqueous ammonium hydroxide (0.341 g, 9.74 mmol) in DCM (20 mL) was stirred at rt overnight. The mixture was concentrated and the residue was extracted with EtOAc. The organic layer was washed with water and brine, dried and evaporated to a thick oil, which was purified by HPLC to afford 5-(4-chlorobenzyl)-2-pyridin-4-yl-1,3-oxazole-4-carboxamide (15 mg, 10%). LCMS (FA) ES+314.1, 315.9.

Step 6. 4-[5-(4-chlorobenzyl)-4-(4H-1,2,4-triazol-3-yl)-1,3-oxazol-2-yl]pyridine A mixture of 5-(4-chlorobenzyl)-2-pyridin-4-yl-1,3-oxazole-4-carboxamide (0.130 g, 0.41 mmol) and 1,1-Dimethoxy-N,N-dimethylmethanamine (3.0 mL, 22 mmol) in Toluene (25 mL) was heated under argon at 40° C. overnight. The reaction mixture was then concentrated to an oily residue. Acetic acid (20 mL, 350 mmol) and Hydrazine (1.0 mL, 30 mmol) were added to the flask and the mixture was heated 60° C. for another 1 hour. The mixture was concentrated and the residue was purified by HPLC to afford 4-[5-(4-chlorobenzyl)-4-(4H-1,2,4-triazol-3-yl)-1,3-oxazol-2-yl]pyridine (7 mg, 5. 2%). LCMS (FA) ES+338.0, 339.9. 1H NMR (400 MHz, MeOD) δ ppm 8.73-8.64 (m, 2H), 8.49-8.33 (m, 1H), 8.05-7.97 (m, 1H), 7.89-7.75 (m, 2H), 7.38 (d, J=7.16 Hz, 2H), 7.30 (d, J=6.64 Hz, 2H), 4.60 (s, 2H).

The following analytical methods were used:

LCMS sectra were run on a Phenominex Luna 5 μm C18 50×4.6 mm column on a Hewlett-Packard HP1100 using the following gradients:

Method Formic Acid (FA): Acetonitrile containing 0 to 100 percent 0.1% formic acid in water (2.5 ml/min for a 3 minute run).

Method Ammonium Acetate (AA): Acetonitrile containing 0 to 100 percent 10 mM ammonium acetate in water (2.5 ml/min for a 3 minute run).

NMR spectrum is shown by proton NMR, with tetramethylsilane as the internal standard and using 300 MHz Bruker Avance spectrometer equipped with a 5 mm QNP probe and 400 MHz Bruker Avance II spectrometer equipped with a 5 mm QNP probe for the measurement; δ values are expressed in ppm.

Formulation Example 1

Amount Per Tablet

| | |
|---|---|
| (1) Compound obtained in Example 1 | 10.0 mg |
| (2) Lactose | 60.0 mg |
| (3) Corn starch | 35.0 mg |
| (4) Gelatin | 3.0 mg |
| (5) Magnesium stearate | 2.0 mg |

A mixture of 10.0 mg of the compound obtained in Example 1, 60.0 mg of lactose and 35.0 mg of corn starch is granulated through a 1 mm-mesh sieve using 0.03 ml of a 10% by weight aqueous solution of gelatin (3.0 mg of gelatin), after which the granules are dried at 40° C. and filtered again. The granules obtained are mixed with 2.0 mg of magnesium stearate and compressed. The core tablets obtained are coated with a sugar coat comprising a suspension of sucrose, titanium dioxide, talc and gum arabic and polished with beeswax to yield sugar-coated tablets.

Formulation Example 2

Dose Per Tablet

| | |
|---|---|
| (1) Compound obtained in Example 1 | 10.0 mg |
| (2) Lactose | 70.0 mg |
| (3) Corn starch | 50.0 mg |
| (4) Soluble starch | 7.0 mg |
| (5) Magnesium stearate | 3.0 mg |

10.0 mg of the compound obtained in Example 1 and 3.0 mg of magnesium stearate are granulated using 0.07 ml of an aqueous solution of soluble starch (7.0 mg of soluble starch), after which these granules are dried and mixed with 70.0 mg of lactose and 50.0 mg of corn starch. This mixture is compressed to yield tablets.

Biological Data:

PI3K and VPS34 Enzyme Assays

Cloning, Expression, and Purification of PI3Ks and VPS34

The catalytic subunits of PI3Ks are cloned into either pDEST8(p110 alpha) or pDEST10(p110beta, p110delta, and p110gamma) as N-terminal His tagged fusion proteins using the Gateway system (Invitrogen, catalog#11804-010 for pDEST8 and 11806-015 for pDEST10). The sequences are verified before recombinant protein expression using the Baculovirus Expression System with Gateway® Technology. The accession numbers for the subunits are as follows:

p110 alpha (GB: U79143)
p110beta (GB: S67334)
p110delta (GB: U86453)
p110gamma (GB: X83368)

The regulatory subunits of PI3Ks are cloned into pDEST8 as un-tagged protein using the Gateway system (Catalog#11804-010). The sequences are verified before recombinant protein expression using the Baculovirus Expression System with Gateway® Technology. The accession numbers for the subunits are as following:

p85 alpha (GB: BC030815)
p101(GB: AB028925)

VPS34 (accession number GB:BC033004) is cloned into pDEST20-Thombin as N-terminal GST tagged fusion proteins using the Gateway system (Invitrogen, catalog#11804-013). The sequences are verified before recombinant protein expression using the Baculovirus Expression System with Gateway® Technology.

For expression of the p110 complexes, the p85 (MOI of 4) is co-infected with p110 alpha, beta, and delta respectively (1MOI) in SF9 cells and harvested at 60 hours post co-infection. P110 gamma was infected at 1 MOI and harvested at 60 hours post infection.

For purification, PI3Ks are purified by Ni-NTA Agarose (Qiagen #30250) followed by Mono Q 10/100 GL (Ge Healthcare #17-5167-01). VPS34 is purified by Glutathione Sepharose 4 Fast Flow (GE Healthcare #17-5132-03) followed by HiTrap Q (GE Healthcare #17-1153-01).

For expression VPS34 was infected at 1MOI in SF9 cells and harvested 72 hours post infection.

For purification, VPS34 is purified by Glutathione Sepharose 4 Fast Flow (GE Healthcare #17-5132-03) followed by HiTrap Q (GE Healthcare #17-1153-01).

PI3K and VPS34 Assay Conditions

1) Human PI3Kα Enzyme Assay Method 0.5 uL compounds in DMSO are added to wells of a 384 well microtitre plate (Corning 3575). At room temperature: 10 ul PI3K reaction buffer (50 mM Hepes, 5 mM DTT, 150 mM NaCl, 10 mM beta-glycerophosphate, 10 mM $MgCl_2$, 0.25 mM sodium cholate and 0.001% CHAPS, pH 7.00) containing ATP (25 uM, Promega) is added followed immediately by 10 ul PI3K reaction buffer containing di-C8 PI (4,5)P2 (3.5 uM, CellSignals) and PI3Kalpha (0.4875 nM, Millennium Protein Sciences Group) and the mixture is incubated with shaking at room temperature for 30 minutes. Then 5 ul PI3K stop mix (50 mM Hepes, 5 mM DTT, 150 mM NaCl, 0.01% Tween-20, 15 mM EDTA and 25 nM biotin-PI (3,4,5)P3 (Echelon) is added to quench the reaction followed immediately by addition of 5 ul HTRF detection mix (50 mM Hepes, 5 mM DTT, 150 mM NaCl, 0.01% Tween-20, 40 mM KF, 10 nM GST:GRP-1 PH domain (Millennium Protein Sciences Group), 15 nM Streptavidin-XL (CisBio) and 0.375 nM anti-GST antibody (CisBio) at pH 7.00). The plates are then incubated for 1 hour at room temperature with shaking and then read on a BMG PheraStar Plus reader.

2) Human PI3K beta, delta and gamma isoforms are tested using the procedure described for PI3K alpha above but with the following changes: PI3K beta (5.25 nM), PI3K delta (0.75 nM) and PI3K gamma (5 nM). All isoforms supplied by Millennium Protein Science Group.

3) VPS34 is assayed using Adapta™ Universal Kinase Assay Kit (Invitrogen).

4) Human VPS34 Enzyme Assay Method 100 nL compounds in DMSO are added to wells of a 384 well microtitre plate (Greiner 780076). At room temperature: 5 ul VPS34 reaction buffer (Invitrogen Assay Buffer Q (diluted 1 in 5 with nanopure water) plus 2 mM DTT and 2 mM MnCl2) containing ATP (20 uM, Promega) and 200 uM PI-PS substrate (Invitrogen PV5122) is added followed immediately by 5 ul VPS34 reaction buffer (as above) containing VPS34 (5 nM, Millennium Protein Sciences Group) and the mixture is incubated with shaking at room temperature for 1 hour. Then 5 ul VPS34 stop-detect mix (as per Invitrogen Adapta Assay kit (PV5009) instructions (contains kinase quench buffer, TR-FRET buffer, Adapta Eu anti-ADP antibody and Alexa Fluor 647 ADP tracer)) is added to quench the reaction. The plates are then incubated for 30 minutes at room temperature with shaking and then read on a BMG PheraStar Plus reader.

PI3K Cell Assays

1) In-Cell Western Assay

The pSer473 AKT LI-COR In-Cell Western Assay is a quantitative immunofluorescent assay that measures phosphorylation of serine 473 AKT (pSer473 AKT) in WM266.4 and SKOV3 tumor cell lines grown in cell culture.

WM266.4 cells are propagated in Minimum Essential Media (MEM) (Invitrogen) containing L-glutamine, 10% Fetal Bovine Serum, 1 mM MEM Sodium Pyruvate, and 0.1 mM MEM Non-Essential Amino Acids and SKOV3 cells are propagated in McCoy's 5A Media (modified) (Invitrogen) containing L-Glutamine and 10% Fetal Bovine Serum. Both cell lines are kept in a humidified chamber at 37° C. with 5% $CO_2$. For the pSer473 AKT LI-COR In-Cell Western Assay, $1.5 \times 10^4$ WM266.4 and $1.5 \times 10^4$ SKOV3 cells are cultured in 100 µl of media per well in tissue culture-treated black-walled, clear bottom Optilux 96-well plates (BD Biosciences) for 16-20 hours. Prior to addition of compounds, cell media is removed and replaced with 75 µl of fresh media. Test compounds in DMSO are diluted 1:100 in media. The diluted test compounds are added to the cells (25 µl per well) in 3-fold dilutions with a final concentration range of 0.0015 to 10 µM. The cells are incubated for 2 hours in a humidified chamber at 37° C. with 5% $CO_2$. Immediately following compound incubation, all liquid is removed from the wells and cells are fixed with 4% paraformaldehyde in PBS (150 µl per well) for 20 minutes at room temperature. The paraformaldehyde solution is removed from wells and the cells are permeabilized with 200 µl 0.1% Triton X-100 in PBS per well for 10 min×3 at room temperature. After removal of PBS+ 0.1% Triton X-100, 150 µl Odyssey blocking buffer (LI-COR Biosciences) is added to each well and plates are incubated at room temperature for 1.5 h. Blocking buffer is removed from the wells and primary antibodies (Phospho-AKT (Ser473) (D9E) XP™ Rabbit mAb and AKT (pan) (40D4) Mouse mAb, Cell Signaling Technology) diluted in Odyssey blocking buffer are added (50 µl per well). Plates are incubated at 4° C. overnight. The cells are washed for 20 min×3 with PBS+ 0.1% Tween-20 (200 µl per well). Secondary antibodies (IRDye 680 Goat anti-Rabbit IgG (H+L) and IRDye 800CW Goat anti-Mouse IgG (H+L), LI-COR Biosciences) are diluted in Odyssey blocking buffer and added to wells (50 µl per well) followed by a 1 h incubation at room temperature, protected from light. Cells are washed for 20 min×3 with PBS+0.1% Tween-20 (200 µl per well). Wash buffer is completely removed from wells after last wash, plates are protected from light until scanned and analyzed with the Odyssey Infrared Imaging System (LI-COR Biosciences). Both pS473 AKT and AKT are simultaneously visualized with the 680 nm fluorophore indicated by a red color and the 800 nm fluorophore indicated by a green color. Relative fluorescence units derived from the scans allow for quantitative analyses of both labeled proteins and the ratio of pS473 AKT to AKT is calculated. Concentration response curves are generated by plotting the average ratios of PI3K inhibitor-treated samples relative to DMSO-treated controls to determine percent change in expression of pS473 AKT.

2) ATPlite Viability Assay

The ATPLite™ Assay (Perkin-Elmer) measures cellular adenosine-triphosphate (ATP) through the generation of a luminescent signal formed from the ATP-dependent enzyme firefly luciferase. The luminescent signal intensity can be used as a measure of cellular proliferation, and can be used to assess the anti-proliferative effects of PI3K inhibitors.

WM266.4 cells propagated in Minimum Essential Media (MEM) (Invitrogen) containing L-Glutamine, 10% Fetal Bovine Serum, 1 mM MEM Sodium Pyruvate, and 0.1 mM MEM Non-Essential Amino Acids are cultured in 384-well tissue culture-treated Black/Clear plates (Falcon) at $1 \times 10^3$ cells per well in a volume of 75 µl in a humidified chamber at 37° C. with 5% $CO_2$ for 24 h. Test compounds (2 µl in 100% DMSO) are diluted in 95 µl of cell culture media. The diluted test compounds are added (8 µl per well) to 384-well plates. Final concentration range of 3-fold serial dilution of compounds is 0.001 to 20 µM. Plates are incubated for 72 h in a humidified chamber at 37° C. with 5% $CO_2$. One control plate without compound addition is processed at the start of the 72 h incubation as a "Time Zero" reading for quantitative evaluation of cell viability at start of assay. After 72 h, all but 25 µl of cell culture media is removed from each well, followed by the addition of 25 µl of ATPlite 1 step reagent (Perkin Elmer) to each well. Luminescence is measured on a LEADSeeker Luminescence Counter (GE Healthcare Life Sciences). Concentration response curves are generated by calculating the luminescence decrease in test compound-treated samples relative to DMSO-treated controls, and growth inhibition ($IC_{50}$) values are determined from the curves.

Vps34 Cell Assays

1) FYVE Domain Redistribution Assay

The FYVE domain redistribution assay monitors translocation of EGFP-2xFYVE from its initial location bound to (PtdIns(3)P) in early endosomes to the cytoplasm in response to test compounds. Recombinant U2OS cells stable expressing the FYVE finger from the human homologue of the hepatocyte growth factor-regulated tyrosine kinase substrate Hrs, duplicated in tanden (GenBank Acc. NM_004712) and fused to the C-terminus of enhanced green fluorescent protein (EGFP). U2OS cells are adherent epithelial cells derived from human osteosarcoma. Expression of EGFP-2X-FYVE is controlled by a standard CMV promoter and continous expression is maintained by addition of geneticin to the culture medium. Localization of the fusion protein within the cells is imaged on the Evotec Technologies OPERA Confocal Imager and Integrated Spot Signal Per Cellular Signal is quantified using Acapella software. Using this information, $IC_{50}$ values for inhibitors can be determined U2OS EGFP-2xFYVE cells are propagated in Dulbecco's Modified Eagle Media High glucose (D-MEM) (Invitrogen cat. 11995) containing 10% Fetal Bovine Serum (HyClone cat. SH30071.02) and 0.5 mg/ml Geneticin (Invitrogen) and kept in a humidified chamber at 37° C. with 5% $CO_2$. $8 \times 10^3$ cells are cultured in 100 µl of media per well in tissue culture-treated black-walled, clear bottom Optilux 96-well plates (BD Biosciences) for 16-24 hours.

Prior to addition of compounds, cell media is removed and replaced with 75 µl of fresh media. Test compounds in DMSO are diluted 1:100 in media. The diluted test compounds are added to the cells (25 µl per well) in 3-fold dilutions with a final concentration range of 0.0015 to 10 µM. The cells are incubated for 30 minutes in a humidified chamber at 37° C. with 5% $CO_2$. Immediately following compound incubation, all liquid is removed from the wells and cells are fixed with 4% paraformaldehyde in PBS (75 µl per well) for 15 minutes at room temperature. The paraformaldehyde solution is removed from wells and washed once with PBS (100 µl per well). The PBS is removed and cells are incubated with DRAQ5 Nuclear Dye (Alexis/Biostatus) (85 µl per well). The plates are covered with Flash Plate plastic adhesive foil and imaged on the Evotec Technologies OPERA Confocal Imager Opera after at least a 30 minute incubation. Concentration curves are generated by calculating the Integrated Spot Intensity Per Cellular Signal decrease in test-compound treated samples relative to DMSO-treated controls and a 100% control inhibitor.

As detailed above, compounds of the invention inhibit PI3K. In certain embodiments, compounds inhibit one or more isoforms of PI3K. In other embodiments, compounds of the invention inhibit PI3Kalpha and have an IC50>1.0 µM. For example, these compounds include 1, 2. In still other embodiments, compounds of the invention inhibit PI3K beta and have an IC50<1.0 µM but >0.1 µM. For example, these compounds include compounds 1, 2.

While we have described a number of embodiments of this invention, it is apparent that our basic examples may be altered to provide other embodiments, which utilize the compounds and methods of this invention. Therefore, it will be appreciated that the scope of this invention is to be defined by the appended claims rather than by the specific embodiments, which have been represented by way of example.

The invention claimed is:
1. A compound of formula IB:

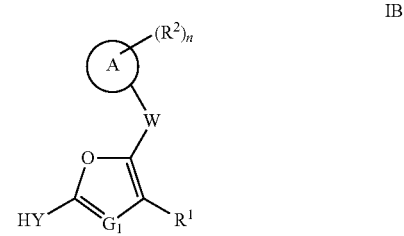

IB wherein:
$R^1$ is CY, —C(O)N($R^3$)$_2$, —C(O)O$R^3$, —C(O)(NH)OH, —C(=NH)NHOH, —C(O)N$R^3$N($R^3$)$_2$, —C(=N—NH$_2$)NH$_2$, —C(=N)N($R^3$)$_2$, wherein:
CY is

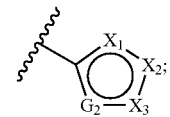

wherein:
$G_2$ is —N=, =N—, or —N($R^{3'}$), wherein:
  each occurrence of $R^3$ and $R^{3'}$ is independently hydrogen or an optionally substituted $C_{1-6}$ aliphatic, wherein:
  $X_1$, $X_2$, and $X_3$, are each independently N, N$R^{3'}$, O, S, or C$R^4$, provided that only one of $X_1$, $X_2$, or $X_3$ may be O, S, or N$R^{3'}$;
  each occurrence of $R^4$ is independently hydrogen, —CN, halogen, —$Z_3$—$R^6$, or an optionally substituted group selected from $C_{1-6}$ aliphatic, or 3-10-membered cycloaliphatic, wherein:
    $Z_3$ is selected from an optionally substituted $C_{1-3}$ alkylene chain, —O—, —N($R^{4a}$)—, —S—, —S(O)—, —S(O)$_2$—, —C(O)—, —CO$_2$—, —C(O)N$R^{4a}$—, —N($R^{4a}$)C(O)—, —N($R^{4a}$)CO$_2$—, —S(O)$_2$N$R^{4a}$—, —N($R^{4a}$)S(O)$_2$—, —OC(O)N(R$^{4a}$)—, —N(R$^{4a}$)C(O)NR$^{4a}$—, —N(R$^{4a}$)S(O)$_2$N(R$^{4a}$)—, or —OC(O)—;

R$^{4a}$ is hydrogen or an optionally substituted C$_{1-4}$ aliphatic, and

R$^6$ is hydrogen or an optionally substituted group selected from C$_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

or wherein two adjacent occurrences of R$^{3'}$ or R$^4$, taken together with the atom to which they are bound, form an optionally substituted fused group selected from 5-6-membered aryl, or 5-6-membered heteroaryl having 1-5 heteroatoms independently selected from nitrogen, oxygen, or sulfur;

Ring A is a group selected from 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of R$^2$ is independently —R$^{12a}$, -T$_2$-R$^{12d}$, or —V$_2$-T$_2$-R$^{12d}$, and:

each occurrence of R$^{12a}$ is independently halogen, —CN, —NO$_2$, —R$^{12c}$, —N(R$^{12b}$)$_2$, —OR$^{12b}$, —SR$^{12c}$, —S(O)$_2$R$^{12c}$, —C(O)R$^{12b}$, —C(O)OR$^{12b}$, —C(O)N(R$^{12b}$)$_2$, —S(O)$_2$N(R$^{12b}$)$_2$, —OC(O)N(R$^{12b}$)$_2$, —N(R$^{12e}$)C(O)R$^{12b}$, —N(R$^{12e}$)SO$_2$R$^{12c}$, —N(R$^{12e}$)C(O)OR$^{12b}$, —N(R$^{12e}$)C(O)N(R$^{12b}$)$_2$, or —N(R$^{12e}$)SO$_2$N(R$^{12b}$)$_2$, or two occurrences of R$^{12b}$, taken together with a nitrogen atom to which they are bound, form an optionally substituted 4-7-membered heterocyclyl ring having 0-1 additional heteroatoms selected from nitrogen, oxygen, or sulfur;

each occurrence of R$^{12b}$ is independently hydrogen or an optionally substituted group selected from C$_1$-C$_6$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of R$^{12c}$ is independently an optionally substituted group selected from C$_1$-C$_6$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of R$^{12d}$ is independently hydrogen or an optionally substituted from 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of R$^{12e}$ is independently hydrogen or an optionally substituted C$_{1-6}$ aliphatic group;

each occurrence of V$_2$ is independently —N(R$^{12e}$)—, —O—, —S—, —S(O)—, —S(O)$_2$—, —C(O)—, —C(O)O—, —C(O)N(R$^{12e}$)—, —S(O)$_2$N(R$^{12e}$)—, —OC(O)N(R$^{12e}$)—, —N(R$^{12e}$)C(O)—, —N(R$^{12e}$)SO$_2$—, —N(R$^{12e}$)C(O)O—, —N(R$^{12e}$)C(O)N(R$^{12e}$)—, —N(R$^{12e}$)SO$_2$N(R$^{12e}$)—, —OC(O)—, or —C(O)N(R$^{12e}$)—O—; and T$_2$ is an optionally substituted C$_1$-C$_6$ alkylene chain wherein the alkylene chain optionally is interrupted by —N(R$^{13}$)—, —O—, —S—, —S(O)—, —S(O)$_2$—, —C(O)—, —C(O)O—, —C(O)N(R$^{13}$)—, —S(O)$_2$N(R$^{13}$)—, —OC(O)N(R$^{13}$)—, —N(R$^{13}$)C(O)—, —N(R$^{13}$)SO$_2$—, —N(R$^{13}$)C(O)O—, —N(R$^{13}$)C(O)N(R$^{13}$)—, —N(R$^{13}$)S(O)$_2$N(R$^{13}$)—, —OC(O)—, or —C(O)N(R$^{13}$)—O— or wherein T$_3$ or a portion thereof optionally forms part of an optionally substituted 3-7 membered cycloaliphatic or heterocyclyl ring, wherein R$^{13}$ is hydrogen or an optionally substituted C$_{1-4}$aliphatic group;

n is 0 to 4;

W is selected from —C(R$^7$)$_2$—, —C(=C(R$^7$)$_2$)—, —C(R$^7$)$_2$O—, —C(R$^7$)$_2$NR$^{7a}$—, —O—, —N(R$^{7b}$)—, —S—, —S(O)—, —S(O)$_2$—, —C(O)—, —C(O)NR$^{7a}$—, or —N(R$^{7a}$)C(O)—, wherein:

each occurrence of R$^7$ is independently hydrogen, or an optionally substituted group selected from C$_{1-6}$ aliphatic, 6-10-membered aryl, 5-10-membered heteroaryl having 1-5 heteroatoms independently selected from nitrogen, oxygen, or sulfur, —N(R$^{7b}$)$_2$, —OR$^{7a}$, —SR$^{7a}$, halo, or —CN;

each occurrence of R$^{7a}$ is independently hydrogen or optionally substituted C$_{1-6}$ aliphatic;

each occurrence of R$^{7b}$ is independently hydrogen, optionally substituted C$_{1-6}$ aliphatic, —C(O)R$^{7a}$, or —S(O)$_2$R$^{7a}$; or wherein any two occurrences of R$^7$, R$^{7a}$, or R$^{7b}$ taken together with the atom to which they are bound, form an optionally substituted group selected from a 3-6-membered cycloaliphatic ring, 6-10-membered aryl, 3-6-membered heterocyclyl having 1-5 heteroatoms independently selected from nitrogen, oxygen, or sulfur, or 5-10-membered heteroaryl having 1-5 heteroatoms independently selected from nitrogen, oxygen, or sulfur;

or wherein any two occurrences of R$^{7a}$ and R$^2$, or R$^{7b}$ and R$^2$ taken together with the nitrogen atom to which they are bound, form an optionally substituted group selected from 3-6-membered heterocyclyl having 1-5 heteroatoms independently selected from nitrogen, oxygen, or sulfur, or 5-10-membered heteroaryl having 1-5 heteroatoms independently selected from nitrogen, oxygen, or sulfur;

G$_1$ is N or —CR$^8$, wherein R$^8$ is H, —CN, halogen, -Z-R$^9$, C$_{1-6}$ aliphatic, or 3-10-membered cycloaliphatic, wherein:

Z is selected from an optionally substituted C$_{1-3}$ alkylene chain, —O—, —N(R$^{8a}$)—, —S—, —S(O)—, S(O)$_2$—, —C(O)—, —CO$_2$—, —C(O)NR$^{8a}$—, —N(R$^{8a}$)C(O)—, —N(R$^{8a}$)CO$_2$—, —S(O)$_2$NR$^{8a}$—, —N(R$^{8a}$)S(O)$_2$—, —OC(O)N(R$^{8a}$)—, —N(R$^{8a}$)C(O)NR$^{8a}$—, —N(R$^{8a}$)S(O)$_2$N(R$^{8a}$)—, or —OC(O)—;

R$^{8a}$ is hydrogen or an optionally substituted C$_{1-4}$ aliphatic, and

R$^9$ is hydrogen or an optionally substituted group selected from C$_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur; and HY is

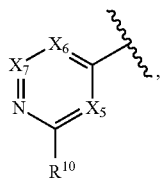

wherein each occurrence of $X_5$, $X_6$ and $X_7$ is —$CR^{10}$;
wherein $R^{10}$ is $R^{10b}$, —$V_1$—$R^{10c}$, -$T_1$-$R^{10b}$, or —$V_1$-$T_1$-$R^{10b}$ wherein:

$V_1$ is —$NR^{11}$—, —$NR^{11}$—C(O)—, —$NR^{11}$—C(S)—, —$NR^{11}$—C($NR^{11}$)—, —$NR^{11}$C(O)$OR^{10a}$—, —$NR^{11}$C(O)$NR^{11}$—, —$NR^{11}$C(O)$SR^{10a}$—, —$NR^{11}$C(S)$OR^{10a}$—, —$NR^{11}$C(S)$NR^{11}$—, —$NR^{11}$C(S)$SR^{10a}$—, —$NR^{11}$C($NR^{11}$)$OR^{10a}$—, —$NR^{11}$C($NR^{11}$)$NR^{11}$—, —$NR^{11}$S(O)$_2$—, —$NR^{11}$S(O)$_2$$NR^{11}$—, —C(O)—, —$CO_2$—, —C(O)$NR^{11}$—, —C(O)$NR^{11}$O—, —$SO_2$—, or —$SO_2$$NR^{11}$—;

each occurrence of $R^{10a}$ is independently hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

$T_1$ is an optionally substituted $C_1$-$C_6$alkylene chain wherein the alkylene chain optionally is interrupted by —N($R^{11}$)—, —O—, —S—, —S(O)—, —S(O)$_2$—, —C(O)—, —C(O)O—, —C(O)N($R^{11}$)—, —S(O)$_2$N($R^{11}$)—, —OC(O)N($R^{11}$)—, —N($R^{11}$)C(O)—, —N($R^{11}$)$SO_2$—, —N($R^{11a}$)C(O)O—, —$NR^{10a}$ C(O)N($R^{10a}$)—, —N($R^{10a}$)S(O)$_2$N($R^{10a}$)—, —OC(O)—, or —C(O)N($R^{11}$)—O— or wherein $T_1$ forms part of an optionally substituted 3-7 membered cycloaliphatic or heterocyclyl ring;

each occurrence of $R^{10b}$ is independently hydrogen, halogen, —CN, —$NO_2$, —N($R^{11}$)$_2$, —$OR^{10a}$, —$SR^{10a}$, —S(O)$_2$$R^{10a}$, —C(O)$R^{10a}$, —C(O)$OR^{10a}$, —C(O)N($R^{11}$)$_2$, —S(O)$_2$N($R^{11}$)$_2$, —OC(O)N($R^{11}$)$_2$, —N($R^{11}$)C(O)$R^{10a}$, —N($R^{11}$)$SO_2$$R^{10a}$, —N($R^{11}$)C(O)$OR^{10a}$, —N($R^{11}$)C(O)N($R^{11}$)$_2$, or —N($R^{11}$)$SO_2$N($R^{11}$)$_2$, or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{10c}$ is independently hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur, or $R^{10a}$ and $R^{10c}$ taken together with a nitrogen atom to which they are bound form an optionally substituted 4-7-membered heterocyclyl ring having 0-1 additional heteroatoms independently selected from nitrogen, oxygen, or sulfur;

each occurrence of $R^{11}$ is independently hydrogen, —C(O)$R^{11a}$, —$CO_2$$R^{11a}$, —C(O)N($R^{11a}$)$_2$, —C(O)N($R^{11a}$)—$OR^{11a}$, —$SO_2$$R^{11a}$, —$SO_2$N($R^{11a}$)$_2$, or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

wherein each occurrence of $R^{11a}$ is independently hydrogen or an optionally substituted group selected from $C_{1-6}$aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur.

2. The compound of claim 1, wherein each occurrence of $R^{10}$ is independently selected from —CN, —$OR^{10a}$, —N($R^{11}$)$_2$, halogen, $C_{1-4}$alkyl, —N($R^{11}$)COR$^{10a}$, or wherein two occurrences of $R^{10}$, taken together with the atoms to which they are bound form an optionally substituted group selected from a fused 5- or 6-membered cycloaliphatic, 4-10-membered heterocyclyl, 6-10-membered aryl or 5-10-membered heteroaryl ring, wherein the heterocyclyl and heteroaryl rings have 1-3 heteroatoms independently selected from nitrogen, oxygen, or sulfur.

3. The compound of claim 1, wherein $R^1$ is CY, and CY is

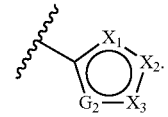

4. The compound of claim 3, wherein $X_1$ is N, $G_2$ is —N($R^3$)—, and $X_2$ and $X_3$ are CH.

5. The compound of claim 3, wherein $X_1$ and $X_2$ are N, $G_2$ is —N($R^3$)—, and $X_3$ is CH.

6. The compound of claim 3, wherein $X_3$ is N, $G_2$ is —N($R^3$)—, and $X_1$ and $X_2$ are CH.

7. The compound of claim 3, wherein $X_1$ is N, $X_2$ is CH, $X_3$ is —N($R^3$)— and $G_2$ is =N—.

8. The compound of claim 1, wherein Ring A is an optionally substituted 6-10-membered aryl or 5-10-membered heteroaryl having 1-5 heteroatoms independently selected from nitrogen, oxygen, or sulfur; and n is 0 to 3.

9. The compound of claim 8, wherein Ring A is a phenyl group optionally substituted with 1-3 independent occurrences of halogen, $C_{1-3}$ alkyl, —CN, $C_{1-3}$haloalkyl, —$OC_{1-3}$ alkyl, —$OC_{1-3}$ haloalkyl, —NHC(O)$C_{1-3}$ alkyl, —NHC(O)NHC$_{1-3}$ alkyl, NHS(O)$_2$$C_{1-3}$ alkyl, or —C(O)H; and n is 0 to 3.

10. The compound of claim 9, wherein Ring A is a phenyl group, $R^2$ is halogen and n is 1 to 2.

11. The compound of claim 1, wherein W is —C($R^7$)$_2$—, wherein one occurrence of $R^7$ is hydrogen and the other occurrence of $R^7$ is selected from hydrogen, optionally substituted $C_{1-4}$ aliphatic, $-N(R^{7b})_2$, $-OR^{7a}$, $-SR^{7a}$, halo, or $-CN$; and wherein each occurrence of $R^{7a}$ is independently hydrogen or optionally substituted $C_{1-6}$ aliphatic;

each occurrence of $R^{7b}$ is independently hydrogen, optionally substituted $C_{1-6}$ aliphatic, $-C(O)R^{7a}$, or $-S(O)_2R^{7a}$; or wherein any two occurrences of $R^7$, $R^{7a}$, or $R^{7b}$ taken together with the atom to which they are bound, form an optionally substituted group selected from a 3-6-membered cycloaliphatic ring, 6-10-membered aryl, 3-6-membered heterocyclyl having 1-5 heteroatoms independently selected from nitrogen, oxygen, or sulfur, or 5-10-membered heteroaryl having 1-5 heteroatoms independently selected from nitrogen, oxygen, or sulfur; or any two occurrences of $R^{7a}$ and $R^2$, or $R^{7b}$ and $R^2$ taken together with the nitrogen atom to which they are bound, form an optionally substituted group selected from 3-6-membered heterocyclyl having 1-5 heteroatoms independently selected from nitrogen, oxygen, or sulfur, or 5-10-membered heteroaryl having 1-5 heteroatoms independently selected from nitrogen, oxygen, or sulfur.

12. The compound of claim 1, wherein W is $-C(H)(N(R^{7b})_2)-$, $-CH_2-$, $-C(H)(OR^{7a})-$, $-NR^{7b}-$, or $-N(R^{7a})C(O)-$, wherein each occurrence of $R^{7a}$ is independently hydrogen or optionally substituted $C_{1-6}$ aliphatic; and each occurrence of $R^{7b}$ is independently hydrogen or optionally substituted $C_{1-6}$ aliphatic.

13. A composition comprising a compound of claim 1, and a pharmaceutically acceptable carrier.

* * * * *